United States Patent
Krichevsky

(10) Patent No.: US 9,951,331 B2
(45) Date of Patent: Apr. 24, 2018

(54) TARGETING MICRORNA-26A/B FOR THE TREATMENT OF NEURODEGENERATIVE DISEASE

(71) Applicant: The Brigham and Women's Hospital, Inc., Boston, MA (US)

(72) Inventor: Anna M. Krichevsky, Brookline, MA (US)

(73) Assignee: The Brigham and Women's Hospital, Inc., Boston, MA (US)

(*) Notice: Subject to any disclaimer, the term of this patent is extended or adjusted under 35 U.S.C. 154(b) by 0 days.

(21) Appl. No.: 14/917,065

(22) PCT Filed: Sep. 10, 2014

(86) PCT No.: PCT/US2014/054923
§ 371 (c)(1),
(2) Date: Mar. 7, 2016

(87) PCT Pub. No.: WO2015/038593
PCT Pub. Date: Mar. 19, 2015

(65) Prior Publication Data
US 2016/0272968 A1   Sep. 22, 2016

Related U.S. Application Data

(60) Provisional application No. 61/875,728, filed on Sep. 10, 2013.

(51) Int. Cl.
| C12N 15/113 | (2010.01) |
|---|---|
| A61K 31/7105 | (2006.01) |
| A61K 31/712 | (2006.01) |
| A61K 31/7125 | (2006.01) |
| A61K 45/06 | (2006.01) |

(52) U.S. Cl.
CPC ........ *C12N 15/113* (2013.01); *A61K 31/7105* (2013.01); *A61K 45/06* (2013.01); *C12N 2310/113* (2013.01); *C12N 2310/141* (2013.01); *C12N 2310/315* (2013.01); *C12N 2310/321* (2013.01); *C12N 2310/322* (2013.01); *C12N 2310/3231* (2013.01); *C12N 2320/31* (2013.01)

(58) Field of Classification Search
None
See application file for complete search history.

(56) References Cited

U.S. PATENT DOCUMENTS

| 2003/0148980 A1 | 8/2003 | Metelev et al. |
| 2006/0039890 A1 | 2/2006 | Renshaw et al. |
| 2009/0298916 A1 | 12/2009 | Kauppinen et al. |
| 2013/0210901 A1 | 8/2013 | Soreq et al. |

FOREIGN PATENT DOCUMENTS

| WO | 2010/040112 | 4/2010 |
| WO | 2012/105826 | 8/2012 |
| WO | 2012/122447 | 9/2012 |

OTHER PUBLICATIONS

Plitman et al (European Neuropsychopharmacology (2014) 24, 1591-1605).*
Wang et al (Apoptosis (2010) 15:1382-1402).*
Travessa et al (Mov Disord. 2016; 31 (suppl 2)).*
Crook et al (Journal of Huntington's Disease 2 (2013) 405-436).*
Cummings et al (Alzheimer's Research & Therapy, 2014, 6:37, 7 pages).*
Zhang et al (J Control Release. Dec. 28, 2013;172(3):962-74).*
Majdi et al (Neurol. Sci. Jun. 27, 2016, 7 pages, [Epub ahead of print]).*
Fagan (2016) retrieved from the web at http://www.alzforum.org/news/conference-coverage/first-phase-3-trial-tau-drug-lmtm-did-not-work-period, on Apr. 11, 2017.*
Andorfer et al., "Cell-cycle reentry and cell death in transgenic mice expressing nonmutant human tau isoforms," J. Neurosci., Jun. 2005, 25(22):5446-5454.
Andrusiak et al., "The retinoblastoma protein is essential for survival of postmitotic neurons," J. Neurosci., Oct. 2012, 32(42):14809-14814.
Arendt et al., "Cortical distribution of neurofibrillary tangles in Alzheimer's disease matches the pattern of neurons that retain their capacity of plastic remodelling in the adult brain," Neuroscience, Apr. 1998, 83(4):991-1002.
Bommer et al., "p53-Mediated Activation of miRNA34 Candidate Tumor-Suppressor Genes," Curr Biol., Aug. 2007, 17:1298-1307.
Bonda et al., "Evidence for the progression through S-phase in the ectopic cell cycle re-entry of neurons in Alzheimer disease," Aging, Apr. 2009, 1(4):382-388.
Bonda et al., "Pathological implications of cell cycle re-entry in Alzheimer disease," Expert Rev. Mol. Med., Jun. 2010, 12:e19.
Busser et al., "Ectopic cell cycle proteins predict the sites of neuronal cell death in Alzheimer's disease brain," J. Neurosci., Apr. 1998, 18(8):2801-2807.
Butterfield and Pocernich, "The Glutamatergic System and Alzheimer's Disease," CNS Drugs, 2003, 17(9):641-52.
Byrnes et al., "Cell cycle activation contributes to post-mitotic cell death and secondary damage after spinal cord injury," Brain, Nov. 2007, 130:2977-2992.
Caudle and Zhang, "Glutamate, excitotoxicity, and programmed cell death in Parkinson disease," Exp. Neural., Dec. 2009, 220(2):230-3.
Chau et al., "MicroRNA-21 promotes fibrosis of the kidney by silencing metabolic pathways," Science Translational Medicine, Feb. 2012, 4(121): 121ra18.
Cogswell et al., "Identification of miRNA changes in Alzheimer's disease brain and CSF yields putative biomarkers and insights into 5 disease pathways," J. Alzheimers Dis., May 2008, 14(1):27-41.

(Continued)

*Primary Examiner* — Richard A Schnizer
(74) *Attorney, Agent, or Firm* — Fish & Richardson P.C.

(57) ABSTRACT

Methods for treating a neurodegenerative disorder associated with aggregation of tau protein in the brain of a subject, comprising administering to the subject a therapeutically effective amount of one or more inhibitory nucleic acids targeting microRNA-26a, microRNA-26b, or both microRNA-26a and 26b.

23 Claims, 19 Drawing Sheets

(56) References Cited

OTHER PUBLICATIONS de las Cuevas et al., "Ca2+/calmodulin-dependent modulation of cell cycle elements pRb and p27kipl involved in the enhanced proliferation of lymphoblasts from patients with Alzheimer dementia," Neurobiol. Dis., 2003, 13(3):254-263.
Dill et al., "Intronic miR-26b controls neuronal differentiation by repressing its host transcript, ctdsp2," Genes Dev., Jan. 2012, 26(1):25-30.
Dong et al., "Molecular mechanisms of excitotoxicity and their relevance to pathogenesis of neurodegenerative diseases," Acta. Pharmacologica. Sinica., Apr. 2009, 30:379-387.
Donnelly et al., "RNA Toxicity from the ALS/FTD C9ORF72 Expansion Is Mitigated by Antisense Intervention," Neuron, Oct. 2013, 80(2):415-28.
Fabani et al., "Efficient inhibition of miR-155 function in vivo by peptide nucleic acids," Nucleic Acids Research, Jul. 2010, 38(13): 4466-4475.
Farooqui et al., "Neurochemical Aspects of Excitotoxicity: Chapter 8, Glutamate Receptors and Neurological Disorders" (Springer Science & Business Media, 2007).
Fernandez-Nogales et al., "Huntington's disease is a four-repeat tauopathy with tau nuclear rods," Nature Medicine, Aug. 2014, 20: 881-885.
Fu et al., "Cdk5 Phosphorylates a Component of the HDAC Complex and Regulates Histone Acetylation during Neuronal Cell Death," Neurosignals, 2013, 21:55-60.
Futatsugi et al., "Cyclin-dependent kinase regulates E2F transcription factor through phosphorylation of Rb protein in neurons," Cell Cycle, Apr. 2012, 11(8):1603-1610.
Galderisi et al., "Cell cycle regulation and neural differentiation" Oncogene, Aug. 2003, 22(33):5208-5219.
Gallagher and Schapira, "Etiopathogenesis and treatment of Parkinson's disease," Curr. Top Med. Chem., 2009, 9(10):860-8.
Giovanni et al., "E2F1 mediates death of B-amyloid-treated cortical neurons in a manner independent of p53 and dependent on Bax and caspase 3," J. Biol. Chem., Apr. 2000, 275(16):11553-11560.
Greene et al., "Cell cycle molecules and vertebrate neuron death: E2F at the hub," Cell Death Differ., Jan. 2004, 11(1):49-60.
Hamdane et al., "p25/Cdk5-mediated retinoblastoma phosphorylation is an early event in neuronal cell death," J. Cell. Sci., Mar. 2005, 118:1291-1298.
Hammond, "microRNA detection comes of age," Nat. Methods, Jan. 2006, 3(1):12-13.
Hebert et al., "Loss of microRNA cluster miR-29a/b-1 in sporadic Alzheimer's disease correlates with increased BACE1/beta-secretase expression," PNAS, Apr. 2008, 105(17):6415-6420.
Hebert et al., "MicroRNA regulation of Alzheimer's Amyloid precursor protein expression," Neurobiol. Dis., Mar. 2009, 33(3):422-428.
Hoozemans et al., "Maximal COX-2 and ppRb expression in neurons occurs during early Braak stages prior to the maximal activation of astrocytes and microglia in Alzheimer's disease," J. Neuroinflammation, Nov. 2005, 2:27.
Hou et al., "The transcription factor E2F1 modulates apoptosis of neurons," J. Neurochem., Jul. 2000, 75(1):91-100.
Huang et al., "The Aβ peptide of Alzheimer's disease directly produces hydrogen peroxide through metal ion reduction" Biochemistry, May 1999, 38(24): 7609-7616.
Huse et al., "The PTEN-regulating microRNA miR-26a is amplified in high-grade glioma and facilitates gliomagenesis in vivo," Genes Dev., Jun. 2009, 23(11):1327-1337.
Hwang and Mendell, "MicroRNAs in cell proliferation, cell death, and tumorigenesis," Br. J. Cancer., Mar. 2006, 94(6):776-780.
Illenberger et al., "The endogenous and cell cycle-dependent phosphorylation of tau protein in living cells: implications for Alzheimer's disease," Mol. Biol. Cell., Jun. 1998, 9(6):1495-1512.

International Preliminary Report on Patentability in International Application No. PCT/US2014/054923, dated Mar. 15, 2016, 10 pages.
Janicki and Monteiro, "Presenilin overexpression arrests cells in the G 1 phase of the cell cycle. Arrest potentiated by the Alzheimer's disease PS2(N141I)mutant," Am. J. Pathol., Jul. 1999, 155(1):135-144.
Janssen et al., "Treatment of HCV infection by targeting microRNA," New England Journal of Medicine, May 2013, 368(18): 1685-94.
Jaworski et al., "AAV-tau mediates pyramidal neurodegeneration by cell-cycle reentry without neurofibrillary tangle fomlation in wild-type mice," PLoS One, Oct. 2009, 4(10):e7280.
Jordan-Sciutto et al., "Expression patterns of retinoblastoma protein in Parkinson disease," J. Neuropathol. Exp. Neurol., Jan. 2003, 62(1):68-74.
Kaul et al., "Region-specific tauopathy and synucleinopathy in brain of the alpha-synuclein overexpressing mouse model of Parkinson's disease," BMC Neuroscience, Aug. 2011, 12:79.
Keeney et al., "Cell cycle proteins in brain in mild cognitive impairment: insights into progression to Alzheimer disease," Neurotox. Res., Oct. 2012, 22(3):220-230.
Kim et al., "Integrative genome analysis reveals an oncomir/oncogene cluster regulating glioblastoma survivorship," PNAS, Feb. 2010, 107(5):2183-2188.
Kishida and Klann, "Sources and targets of reactive oxygen species in synaptic plasticity and memory," Antioxidants and Redox Signaling, Feb. 2007, 9(2): 233-244.
Kota et al., "Therapeutic microRNA delivery suppresses tumorigenesis in a murine hoer cancer model," Cell, Jun. 2009, 137(6):1005-1017.
Koval et al., "Method for widespread microRNA-155 inhibition prolongs survival in ALS-model mice," Human Molecular Genetics, Oct. 2013, 22(2): 4127-4135.
Krichevsky and Kosik, "Neuronal RNA granules: a link between RNA localization and stimulation-dependent translation," Neuron., Nov. 2001, 32:683-696.
Krutzfeldt et al., "Silencing of microRNAs in vivo with antagomirs", Nature, Dec. 2005, 438 (7068): 685-689.
Kulshreshtha et al., "Regulation of microRNA expression: the hypoxic component," Cell Cycle, Jun. 2007, 6(12):1426-1431.
Lau and de Strooper, "Dysregulated microRNAs in neurodegenerative disorders." Semin. Cell Dev. Biol., Sep. 2010, 21(7):768-773.
Lee and Leugers, "Tau and Tauopathies," Prog. Mol. Biol. Transl. Sci., 2012, 107:263-93.
Lee and Tsai, "Cdk5: one of the links between senile plaques and neurofibrillary tangles'?" J. Alzheimers. Dis., Apr. 2003, 5(2):127-137.
Lee et al., "Neurodegenerative tauopathies," Annu. Rev. Neurosci., 2001, 24:1121-59.
Lei et al., "Tau protein: relevance to Parkinson's disease," Int J Biochem Cell Biol, Nov. 2010; 42(11): 1775-8.
Liu et al., "The microRNA miR-34 modulates ageing and neurodegeneration in *Drosophila*". Nature, Feb. 2012, 482:519-523.
Lopes et al., "Activation of cell cycle proteins in transgenic mice in response to neuronal loss but not amyloid-beta and tau pathology," J. Alzheimers Dis., 2009, 16(3):541-549.
Lopes et al., "Cdk5 acts as a mediator of neuronal cell cycle re-entry triggered by amyloid-beta and prion peptides," Cell Cycle, Jan. 2009, 8(1):97-104.
Lu et al., "MiR-26a inhibits cell growth and tumorigenesis of nasopharyngeal carcinoma through repression of EZH2," Cancer Res., Jan. 2011, 71(1):225-233.
Ludolph et al., "Tauopathies with parkinsonism: clinical spectrum, neuropathologic basis, biological markers, and treatment options," Eur J. Neurol., Mar. 2009, 16(3): 297-309.
Maegdefessel et al., "Inhibition of microRNA-29b reduces murine abdominal aortic aneurysm development," Journal of Clinical Investigation, Feb. 2012, 122(2): 497-506.
Manning and Dyson, "pRB, a tumor suppressor with a stabilizing presence," Trends Cell. Biol., Aug. 2011, 21:433-441.

(56) References Cited

OTHER PUBLICATIONS

Mazanetz and Fischer, "Untangling tau hyperphosphorylation in drug design for neurodegenerative diseases," Nat. Rev. Drug Discov., Jun. 2007, 6(6):464-479.
McShea et al., "Neuronal cell cycle reentry mediates Alzheimer disease-type changes," Biochim. Biophys. Acta., Apr. 2007, 1772(4):467-472.
Mehta et al., "Excitotoxicity: bridge to various triggers in neurodegenerative disorders," Eur. J. Pharmacol., Jan. 2013, 698:6-18.
Milton, NG. "Role of hydrogen peroxide in the aetiology of Alzheimer's disease: implications for treatment," Drugs Aging, 2004, 21(2): 81-100.
Moh et al., "Cell cycle deregulation in the neurons of Alzheimer's disease," Results Probl. Cell Differ., 2011, 53:565-576.
Moon et al., "Inhibition of microRNA-181 reduces forebrain ischemia-induced neuronal loss," Journal of Cerebral Blood Flow & Metabolism, Dec. 2013, 33:1976-1982.
Munoz et al., "The cyclopentenone 15-deoxy-delta(12,14)-prostaglandin J2 inhibits G 1/S transition and retinoblastoma protein phosphorylation in immortalized lymphocytes from Alzheimer's disease patients," Exp. Neural., 2005, 195(2):508-517.
Nagy et al., "Cell cycle markers in the hippocampus in Alzheimer's disease," Acta. Neuropathol., Jul. 1997, 94(1):6-15.
Neve and McPhie, "The cell cycle as a therapeutic target for Alzheimer's disease," Pharmacol. Ther., Jul. 2006, 111(1):99-113.
Park et al., "Conditional neuronal simian virus T antigen expression induces Alzheimer-like tau and amyloid pathology in mice," Park J. Neurosci., Mar. 2007, 27(11):2969-2978.
Park et al., "Involvement of retinoblastoma family members and E2F/DP complexes in the death of neurons evoked by DNA damage," J. Neurosci., May 1, 2000, 20(9):3104-3114.
Pencheva et al., "Convergent multi-miRNA targeting of ApoE drives LRP1/LRP8-dependent melanoma metastasis and angiogenesis," Cell, Nov. 2012, 151(5): 1068-1082.
Preuss et al., "Cell cycle-dependent phosphorylation and microtubule binding of tau protein stably transfected into Chinese hamster ovary cells," Mol. Biol. Cell., Aug. 11, 1995, 6(10):1397-1410.
Provost, "Interpretation and applicability of microRNA data to the context of Alzheimer's and age-related diseases," Aging, Mar. 2010, 2(3):166-169.
Ranganathan et al., "Hypeiphosphorylation of the retinoblastoma gene product and altered subcellular distribution of E2F-1 during Alzheimer's disease and amyotrophic lateral sclerosis," J. Alzheimers Dis., Aug. 2001, 3(4):377-385.
Rashidian et al., "Multiple cyclin-dependent kinases signals are critical mediators of ischemia/hypoxic neuronal death in vitro and in vivo," PNAS, Jul. 22, 2005, 102(39):14080-14085.
Rizzo et al., "Diffusion-weighted brain imaging study of patients with clinical diagnosis of corticobasal degeneration, progressive supranuclear palsy and Parkinson's disease," Brain, Oct. 2008, 131:2690-700.
Satoh, "Molecular network of microRNA targets in Alzheimer's disease brains," Exp. Neural., Jun. 2012, 235(2):436-446.
Schindowski et al., "Neurogenesis and cell cycle-reactivated neuronal death during pathogenic tau aggregation," Genes Brain Behav., Feb. 2008, 1:92-100.
Schwartz et al., "Cell cycle activation in postmitotic neurons is essential for DNA repair." Cell Cycle, Feb. 1, 2007, 6:318-329.
Sellers et al., "A potent transrepression domain in the retinoblastoma protein induces a cell cycle arrest when bound to E2F sites," PNAS, Aug. 16, 1995, 92(25):11544-11548.
Seward et al., "Amyloid-beta Signals Through Tau to Drive Ectopic Neuronal Cell Cycle Re-entry in Alzheimer's Disease," J. Cell. Sci., Mar. 2013.
Sheaff et al., "Cyclin E-CDK2 is a regulator of p27Kip1," Genes Dev., Apr. 11, 1997, 11:1464-1478.
Smith et al., "Cell cycle-related protein expression in vascular dementia and Alzheimer's disease," Neurosci. Lett., Aug. 1999, 271(1):45-48.
Smith et al., "Induction of DNA replication in adult rat neurons by deregulation 20 of the retinoblastoma/E2F G1 cell cycle pathway," Cell. Growth Differ., Dec. 2000, 11(12):625-633.
Smith et al., "MicroRNA-132 loss is associated with tau exon inclusion in progressive supranuclear palsy," Hum. Mol. Genet., Aug. 1, 2011, 20:4016-4024.
Stone et al., "The cell cycle regulator phosphoiylated retinoblastoma protein is associated with tau pathology in several tauopathies," J. Neuropathol. Exp. Neural., Jul. 2011, 70(7):578-587.
Swerdlow, "Alzheimer's disease pathologic cascades: who comes first, what drives what," Neurotox. Res., Oct. 2012, 22(3):182-194.
Thakur et al., "Retinoblastoma protein phosphorylation at multiple sites is associated with neurofibrillary pathology in Alzheimer disease," Int. J. Clin. Exp. Pathol., Jan. 2008, 1(2):134-146.
Vilardo et al., "MicroRNA-101 regulates amyloid precursor protein expression in hippocampal Neurons," J. Biol. Chem., Feb. 9, 2010, 285(24):18344-18351.
Vincent et al., "Aberrant expression of mitotic cdc2/cyclin B1 kinase in degenerating neurons of Alzheimer's disease brain," J. Neurosci., May 15, 1997, 17(10):3588-3598.
Vlach et al., "Phosphorylation-dependent degradation of the cyclin-dependent kinase inhibitor," EMBO J., Sep. 1997, 16:5334-5344.
Wang et al., "Patterns of microRNA expression in normal and early Alzheimer's disease human temporal cortex: white matter versus gray matter," Acta. Neuropathol., Feb. 2011, 121(2):193-205.
Wills et al., "Elevated tauopathy and alpha-synuclein pathology in postmortem Parkinson's disease brains with and without dementia," Exp. Neurol.,Sep. 2010, 225(1): 210-218.
Wong et al., "De-repression of FOXO3a death axis by microRNA-132 and -212 causes neuronal apoptosis in Alzheimer's disease," Hum. Mol. Genet., Apr. 11, 2013, 22:3077-3092.
Yang et al., "DNA replication precedes neuronal cell death in Alzheimer's disease," J. Neurosci.,Apr. 15, 2001, 21(8):2661-2668.
Ye and Blain, "S phase entry causes homocysteine-induced death while ataxia telangiectasia and Rad3 related protein functions anti-apoptotically to protect neurons," Brain, 2010, 133:2295-2312.
Yoshida et al., "CSN5 specifically interacts with CDK2 and controls senescence in a cytoplasmic cyclin E-mediated manner," Sci. Rep., Jan. 11, 2013, 3:1054.
Yoshiyama et al., "Frontotemporal dementia and tauopathy," Current Neurology and Neuroscience Reports, Sep. 2001, 1(5): 413-421.
Yurov et al., "The DNA replication stress hypothesis of Alzheimer's disease," Scientific World Journal, Dec. 18, 2011, 11:2602-2612.
Zhang and Herrup, "Cdk5 and the non-catalytic arrest of the neuronal cell cycle," Cell Cycle, Nov. 15, 2008, 7(22):3487-3490.
Zhang et al., "LNA-mediated anti-miR-155 silencing in low-grade B-cell lymphomas," Blood, Aug. 2012; 120(8): 1678-1686.
Zhang et al., "Cdk5 nuclear localization is p27-dependent in nerve cells: implications for cell cycle suppression and caspase-35 activation." J Biol Chem Feb. 26, 2010 285(18): 14052-14061.
Zhu et al., "MicroRNA-26a/b and their host genes cooperate to inhibit the G 1/S transition by activating the pRb protein," Nucleic Acids Res., Dec. 30, 2011, 40(10):4615-4625.
Zovoilis et al., "microRNA-34c is a novel target to treat dementias," EMBO J., Sep. 2011, 30(20):4299-4308.
Zhu et al., "MicroRNA-195 downregulates Alzheimer's disease amyloid-beta production by targeting BACE1," Brain Res. Bull., 2012, 88(6):596-601.
International Search Report and Written Opinion mailed Jan. 21, 2015 in international application no. PCT/US2014/054923, 14 pgs.
Iqbal et al., "Tau in Alzheimer Disease and Related Tauopathies," Curr Alzheimer Res, 7(8): 656-664 (Dec. 2010).

* cited by examiner

| Age | Gender | PMI (hrs) | Diagnosis | Sample | Cases (n) |
|---|---|---|---|---|---|
| 76.5 ± 5.5 | 5M/3F | 22.4 ± 3.2 | NDAR | Temporal cortex | 8 |
| 79.5 ± 6.7 | 3M/7F | 20.1 ± 7.0 | BraakIII | Temporal cortex | 10 |
| 81.0 ± 6.2 | 5M/5F | 18.1 ± 8.3 | BraakVI | Temporal cortex | 10 |

*PMI: Post Mortem Interval*
*NDAR: No Diagnostic Abnormality Recognized*
*All data are mean ± standard deviation*

FIG. 1A

| miRNA | fold change | pvalues |
|---|---|---|
| let7b | 1.146 | 0.302 |
| let7c | 1.536 | 0.018 |
| let7d | 1.911 | 0.209 |
| Let7i | 3.156 | 0.004 |
| miR-103 | 0.747 | 0.053 |
| miR-124a | 0.377 | 0.111 |
| miR-125a | 0.934 | 0.313 |
| miR-125b | 2.06 | 0.027 |
| miR-132 | 0.641 | 0.004 |
| miR-134 | 1.57 | 0.025 |
| miR-181a | 0.56 | 0.085 |
| miR-26a | 2.041 | 0.023 |
| miR-26b | 2.483 | 0.006 |
| mir-27a | 1.729 | 0.001 |
| miR-27b | 1.849 | 0.004 |
| miR-29a | 1.35 | 0.229 |
| miR-29c | 2.488 | 0.004 |
| miR-204 | 1.153 | 0.485 |
| miR-30a-5p | 1.819 | 0.005 |
| miR-7 | 2.238 | 0.051 |
| miR-9 | 0.947 | 0.451 |

FIG. 1B (SEQ ID NO:1)

(SEQ ID NO:2)

(SEQ ID NO:10)

SEQUENCE LISTING

```
<160> NUMBER OF SEQ ID NOS: 23

<210> SEQ ID NO 1
<211> LENGTH: 77
<212> TYPE: RNA
<213> ORGANISM: Homo sapiens

<400> SEQUENCE: 1
guggccucgu ucaaguaauc caggauaggc ugugcagguc ccaaugggcc uauucuuggu     60
uacuugcacg gggacgc                                                    77

<210> SEQ ID NO 2
<211> LENGTH: 84
<212> TYPE: RNA
<213> ORGANISM: Homo sapiens

<400> SEQUENCE: 2
ggcuguggcu ggauucaagu aauccaggau aggcuguuuc caucugugag gccuauucuu     60
gauuacuugu uucuggaggc agcu                                            84

<210> SEQ ID NO 3
<211> LENGTH: 22
<212> TYPE: RNA
<213> ORGANISM: Homo sapiens
```

```
<400> SEQUENCE: 3
uucaaguaau ccaggauagg cu                                              22

<210> SEQ ID NO 4
<211> LENGTH: 6
<212> TYPE: RNA
<213> ORGANISM: Artificial Sequence
<220> FEATURE:
<223> OTHER INFORMATION: seed sequence of human miR-26a

<400> SEQUENCE: 4 ucaagu                                                                 6

<210> SEQ ID NO 5
<211> LENGTH: 6
<212> TYPE: DNA
<213> ORGANISM: Artificial Sequence
<220> FEATURE:
<223> OTHER INFORMATION: sequence complementary to seed sequence

<400> SEQUENCE: 5 acttga                                                                 6

<210> SEQ ID NO 6
<211> LENGTH: 9
<212> TYPE: DNA
<213> ORGANISM: Artificial Sequence
<220> FEATURE:
<223> OTHER INFORMATION: sequence complementary to seed sequence

<400> SEQUENCE: 6 attacttga                                                              9

<210> SEQ ID NO 7
<211> LENGTH: 8
<212> TYPE: DNA
<213> ORGANISM: Artificial Sequence
<220> FEATURE:
<223> OTHER INFORMATION: sequence complementary to seed sequence

<400> SEQUENCE: 7 ttacttga                                                               8

<210> SEQ ID NO 8
<211> LENGTH: 7
<212> TYPE: DNA
<213> ORGANISM: Artificial Sequence
<220> FEATURE:
<223> OTHER INFORMATION: sequence complementary to seed sequence

<400> SEQUENCE: 8 tacttga                                                                7

<210> SEQ ID NO 9
<211> LENGTH: 22
<212> TYPE: RNA
<213> ORGANISM: Homo sapiens

<400> SEQUENCE: 9
ccuauucuug guuacuugca cg                                              22

<210> SEQ ID NO 10
<211> LENGTH: 77
<212> TYPE: RNA
<213> ORGANISM: Homo sapiens
```

```
<400> SEQUENCE: 10
ccgggaccca guucaaguaa uucaggauag guugugugcu guccagccug uucuccauua    60
cuuggcucgg ggaccgg                                                   77

<210> SEQ ID NO 11
<211> LENGTH: 21
<212> TYPE: RNA
<213> ORGANISM: Homo sapiens

<400> SEQUENCE: 11
uucaaguaau ucaggauagg u                                              21

<210> SEQ ID NO 12
<211> LENGTH: 22
<212> TYPE: RNA
<213> ORGANISM: Homo sapiens

<400> SEQUENCE: 12
ccuguucucc auuacuuggc uc                                             22

<210> SEQ ID NO 13
<211> LENGTH: 21
<212> TYPE: RNA
<213> ORGANISM: Artificial Sequence
<220> FEATURE:
<223> OTHER INFORMATION: seed sequence of human miR-26a

<400> SEQUENCE: 13
uggauaggac uuaaugaacu u                                              21

<210> SEQ ID NO 14
<211> LENGTH: 23
<212> TYPE: RNA
<213> ORGANISM: Homo sapiens

<400> SEQUENCE: 14
aaaguaccca ucuaguacuu gaa                                            23

<210> SEQ ID NO 15
<211> LENGTH: 23
<212> TYPE: RNA
<213> ORGANISM: P. troglodytes

<400> SEQUENCE: 15
aaaguaccca ucuaguacuu gaa                                            23

<210> SEQ ID NO 16
<211> LENGTH: 23
<212> TYPE: RNA
<213> ORGANISM: M. mulatta

<400> SEQUENCE: 16
aaaguacuca ucuaguacuu gaa                                            23

<210> SEQ ID NO 17
<211> LENGTH: 22
<212> TYPE: RNA
<213> ORGANISM: Mus musculus

<400> SEQUENCE: 17
aaguacccau guaguacuug aa                                             22
```

```
<210> SEQ ID NO 18
<211> LENGTH: 22
<212> TYPE: RNA
<213> ORGANISM: Rattus norvegicus

<400> SEQUENCE: 18
agguacccau guaguacuug aa                                              22

<210> SEQ ID NO 19
<211> LENGTH: 21
<212> TYPE: RNA
<213> ORGANISM: Homo sapiens

<400> SEQUENCE: 19
gucuuccaug uaucuuuga a                                                21

<210> SEQ ID NO 20
<211> LENGTH: 21
<212> TYPE: RNA
<213> ORGANISM: P. troglodytes

<400> SEQUENCE: 20
gucuuccaug uaucuuuga a                                                21

<210> SEQ ID NO 21
<211> LENGTH: 21
<212> TYPE: RNA
<213> ORGANISM: M. mulatta

<400> SEQUENCE: 21
gucuuccaug uaucuuuga a                                                21

<210> SEQ ID NO 22
<211> LENGTH: 19
<212> TYPE: RNA
<213> ORGANISM: Mus musculus

<400> SEQUENCE: 22
ucuuccaggg ucuuuugaa                                                  19

<210> SEQ ID NO 23
<211> LENGTH: 20
<212> TYPE: RNA
<213> ORGANISM: Rattus norvegicus

<400> SEQUENCE: 23
gucuuccagg gucuuuugaa                                                 20
```

TARGETING MICRORNA-26A/B FOR THE TREATMENT OF NEURODEGENERATIVE DISEASE

CLAIM OF PRIORITY

This application is a U.S. National Phase Application under 35 U.S.C. § 371 of International Patent Application No. PCT/US2014/054923, filed on Sep. 10, 2014, which claims the benefit of U.S. Provisional Application Ser. No. 61/875,728, filed on Sep. 10, 2013. The entire contents of the foregoing are incorporated herein by reference.

TECHNICAL FIELD

The present invention describes methods for treating a neurodegenerative disorder associated with aggregation of tau protein in the brain of a subject, using inhibitory nucleic acids targeting microRNA-26a, microRNA-26b, or both microRNA-26a and 26b.

BACKGROUND

There are 5.3 million Americans living with Alzheimer's disease (AD), the major neurodegenerative disease of aging, and the number of people affected by the disease is predicted to double within twenty years.

AD is a multifactorial disease characterized by Aβ deposition, tau hyperphosphorylation, oxidative stress, cholinergic deficits, progressive synaptic loss, and neurodegeneration. How all these typical characteristics of AD relate to each other is not clear. One of the earliest neuronal abnormalities in mild cognitive impairment (MCI) and AD is dysregulation of the cell cycle in postmitotic neurons, cells that are not normally cycling (Nagy et al., 1997; Vincent et al., 1997; Yang et al., 2001; Neve and McPhie, 2006; McShea et al., 2007; Bonda et al., 2010). Neuronal cell cycle regulatory failure presented by aberrant cell cycle entry (CCE) and often leading to cell death may be a significant component of AD pathogenesis. Accumulating evidence suggests that CCE in neurons may precede tau and amyloid pathology, and that there is a link between CCE and tau-hyperphosphorylation (Andorfer et al., 2005; Park et al., 2007; Jaworski et al., 2009). A number of studies indicates that almost all neurons that exhibit tau pathology are also positive for various markers of cell cycle (Busser et al., 1998; Keeney et al., 2012; Seward et al., 2013).

Despite significant progress in the field, medical science still has little to offer. Therefore, there is a critical need in new molecular targets, concepts, and approaches to treat this devastating disease.

SUMMARY

A number of microRNAs (miRNAs) are disregulated at early and/or late stages of AD and other neurodegenerative disorders. Some of them may represent important molecular regulators that drive or enhance disease progression.

As described herein, specific miRNAs, i.e., miR-26b, of miR-132 and miR-212, are correlated with AD and disease progression. Levels of miR-26b rise at early stages of AD (Braak III, which usually corresponds to MCI) and remain elevated in the defined pathological areas of human AD brains during the disease progression. We demonstrate that overexpression of this miRNA in cultured post-mitotic neurons leads to CCE. We validate tumor suppressor Retinoblastoma 1 (Rb1) as a principal target that mediates miR-26b-induced CCE in neurons. Furthermore, both overexpression of miR-26b and inhibition of Rb1 cause activation of Cdk5 and increase tau phosphorylation at AD-relevant epitopes, followed by apoptosis and neurodegeneration in culture. As described herein, miR-26b up-regulation, observed in AD, perturbs signalling pathways associated with neuronal cell cycle and thereby causes pleiotropic phenotypes associated with the disease. Thus miR-26b has an important function in the pathophysiology of AD.

Thus, in a first aspect, the invention provides methods for treating a neurodegenerative disorder associated with aggregation of tau protein in the brain of a subject and/or glutamate excitotoxicity. The methods include administering to the subject a therapeutically effective amount of one or more inhibitory nucleic acids targeting microRNA-26a, microRNA-26b, or both microRNA-26a and 26b.

In additional aspects, the invention features the use of an inhibitory nucleic acid targeting microRNA-26a, microRNA-26b, or both microRNA-26a and 26b for treating a neurodegenerative disorder associated with aggregation of tau protein and/or glutamate excitotoxicity in the brain of a subject, as well as the use of an inhibitory nucleic acid targeting microRNA-26a, microRNA-26b, or both microRNA-26a and 26b in the manufacture of a medicament for treating a neurodegenerative disorder associated with aggregation of tau protein and/or glutamate excitotoxicity in the brain of a subject.

In some embodiments, the inhibitory nucleic acid comprises the sequence ACTTGA (SEQ ID NO:5).

In some embodiments, the inhibitory nucleic acid is an antagomiR.

In some embodiments, the inhibitory nucleic acid comprises one or more locked nucleotides.

In some embodiments, the inhibitory nucleic acid is a gapmer or mixmer.

In some embodiments, the inhibitory nucleic acid does not comprise three or more consecutive guanosine nucleotides.

In some embodiments, the inhibitory nucleic acid does not comprise four or more consecutive guanosine nucleotides.

In some embodiments, the inhibitory nucleic acid is 8 to 21 nucleotides in length.

In some embodiments, at least one nucleotide of the inhibitory nucleic acid is a nucleotide analogue.

In some embodiments, at least one nucleotide of the inhibitory nucleic acid comprises a 2' O-methyl.

In some embodiments, each nucleotide of the inhibitory nucleic acid comprises a 2' O-methyl.

In some embodiments, the inhibitory nucleic acid comprises at least one ribonucleotide, at least one deoxyribonucleotide, or at least one bridged nucleotide.

In some embodiments, the bridged nucleotide is a LNA nucleotide, a cEt nucleotide or a ENA modified nucleotide.

In some embodiments, each nucleotide of the oligonucleotide is a LNA nucleotide.

In some embodiments, one or more of the nucleotides of the inhibitory nucleic acid comprise 2'-fluoro-deoxyribonucleotides.

In some embodiments, one or more of the nucleotides of the inhibitory nucleic acid comprise 2'-O-methyl nucleotides.

In some embodiments, one or more of the nucleotides of the inhibitory nucleic acid comprise ENA nucleotide analogues.

In some embodiments, one or more of the nucleotides of the inhibitory nucleic acid comprise LNA nucleotides.

In some embodiments, the nucleotides of the inhibitory nucleic acid comprise phosphorothioate internucleotide linkages between at least two nucleotides.

In some embodiments, the nucleotides of the inhibitory nucleic acid comprise phosphorothioate internucleotide linkages between all nucleotides.

In some embodiments, the neurodegenerative disorder is Alzheimer's disease, Parkinson's disease, Huntington's disease, and frontotemporal dementia (FTD).

In some embodiments, the subject is human.

In some embodiments, the method further includes administering to the subject one or more antidepressants; anxiolytics; or antipsychotic medications.

As used herein, "RNA" refers to a molecule comprising at least one or more ribonucleotide residues. A "ribonucleotide" is a nucleotide with a hydroxyl group at the 2' position of a beta-D-ribofuranose moiety. The term RNA, as used herein, includes double-stranded RNA, single-stranded RNA, isolated RNA, such as partially purified RNA, essentially pure RNA, synthetic RNA, recombinantly-produced RNA, as well as altered RNA that differs from naturally-occurring RNA by the addition, deletion, substitution and/or alteration of one or more nucleotides. Nucleotides of the RNA molecules can also comprise non-standard nucleotides, such as non-naturally occurring nucleotides or chemically synthesized nucleotides or deoxynucleotides.

A "mature microRNA" (mature miRNA) typically refers to a single-stranded RNA molecules of about 21-23 nucleotides in length, which regulates gene expression. miRNAs are encoded by genes from whose DNA they are transcribed, but miRNAs are not translated into protein; instead each primary transcript (pri-miRNA) is processed into a short stem-loop structure (precursor microRNA) before undergoing further processing into a functional mature miRNA. Mature miRNA molecules are partially complementary to one or more messenger RNA (mRNA) molecules, and their main function is to down-regulate gene expression. As used throughout, the term "microRNA" or "miRNA" includes both mature microRNA and precursor microRNA.

By the term "neurodegenerative disorder" is meant a neurological disorder characterized by a progressive loss of neuronal function and structure, and neuron death. Non-limiting examples of neurodegenerative disorders include Parkinson's disease (PD), Alzheimer's disease (AD), Huntington's disease (HD), brain stroke, brain tumors, cardiac ischemia, age-related macular degeneration (AMD), retinitis pigmentosa (RP), and multiple sclerosis (MS). Methods for diagnosing a neurodegenerative disorder are described herein. Additional methods for diagnosing a neurodegenerative disorder are known in the art.

By the term "inhibitory RNA" is meant a nucleic acid molecule that contains a sequence that is complementary to a target nucleic acid (e.g., a target microRNA-26a/b. Non-limiting examples of inhibitory RNAs include interfering RNA, shRNA, siRNA, ribozymes, antagomiRs, and antisense oligonucleotides. Methods of making inhibitory RNAs are described herein. Additional methods of making inhibitory RNAs are known in the art.

As used herein, "an interfering RNA" refers to any double stranded or single stranded RNA sequence, capable—either directly or indirectly (i.e., upon conversion)—of inhibiting or down regulating gene expression by mediating RNA interference. Interfering RNA includes but is not limited to small interfering RNA ("siRNA") and small hairpin RNA ("shRNA"). "RNA interference" refers to the selective degradation of a sequence-compatible messenger RNA transcript.

As used herein "an shRNA" (small hairpin RNA) refers to an RNA molecule comprising an antisense region, a loop portion and a sense region, wherein the sense region has complementary nucleotides that base pair with the antisense region to form a duplex stem. Following post-transcriptional processing, the small hairpin RNA is converted into a small interfering RNA by a cleavage event mediated by the enzyme Dicer, which is a member of the RNase III family.

A "small interfering RNA" or "siRNA" as used herein refers to any small RNA molecule capable of inhibiting or down regulating gene expression by mediating RNA interference in a sequence specific manner. The small RNA can be, for example, about 18 to 21 nucleotides long.

As used herein, an "antagomiR" refers to a small synthetic RNA having complementarity to a specific microRNA target, optionally with either mispairing at the cleavage site or one or more base modifications to inhibit cleavage.

As used herein, the phrase "post-transcriptional processing" refers to mRNA processing that occurs after transcription and is mediated, for example, by the enzymes Dicer and/or Drosha.

By the phrase "risk of developing disease" is meant the relative probability that a subject will develop a neurodegenerative disorder in the future as compared to a control subject or population (e.g., a healthy subject or population).

By the phrase "rate of disease progression" is meant one or more of the rate of onset of symptoms of a neurodegenerative disorder in a subject, the rate of the increasing intensity (worsening) of symptoms of a neurodegenerative disorder in a subject, the frequency of one or more symptoms of a neurodegenerative disorder in a subject, the duration of one or more symptoms of a neurodegenerative disorder in a subject, or the longevity of subject. For example, an increased rate of disease progression can include one or more of: an increased rate of onset of symptoms of a neurodegenerative disorder in a subject, an increased frequency of one or more symptoms of a neurodegenerative disorder in a subject, an increase in the duration of one or more symptoms of a neurodegenerative disorder in a subject, or a decrease in the longevity of a subject. Methods of predicting the rate of disease progression in a subject having a neurodegenerative disorder are described herein.

The term "treating" includes reducing the number of symptoms or reducing the severity, duration, or frequency of one or more symptoms of disease (e.g., a neurodegenerative disease) in a subject. The term treating can also include reducing the risk of developing a neurodegenerative disorder in a subject, delaying the onset of symptoms of a neurodegenerative disorder in a subject, or increasing the longevity of a subject having a neurodegenerative disorder.

Other definitions appear in context throughout this disclosure. Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 1A-C. MiR-26b expression is up-regulated in AD. (A) A table summarizes information about the samples used in this study. (B) Multiplex miRNA expression analyses was performed on samples from temporal cortex of Braak III (n=6) and control brains (n=6). (C) Expression of miR-26b (upper panel) and miR-26a (lower panel) was tested in control, Braak III and Braak VI (n=8 to 10 per condition) specimens by singleplex qRT-PCR, and relative levels calculated as $2^{-deltaCt}$. Uniformly expressed miR-99a was used for normalization. Data represent mean±SEM with Mann Whitney test.

Western blot analysis of post-mitotic neurons 5 days after siRNA-Rb1 transfection shows an increase of tau phosphorylation at Ser404 and Ser202/Thr205. Actin serves as a loading control. (Student's t-test, two-tailed, *p<0.05, n=2). (B) Immunoprecipitation with anti-p35/25 primary antibody followed by western blot analysis for Cdk5 reveals an accumulation of Cdk5 associated with p35/p25 in post-mitotic neurons transfected with either miR-26b or siRb1 (Student's t-test, two-tailed, *p<0.05 and p<0.001, n=3). (C) Immunoprecipitation for Cdk5 followed by in vitro phosphorylation of its substrate peptides Histone H1, Tau, and Rb1, and Western blot analysis with specified phospho-antibodies indicate increased Cdk5 activity in neurons transfected with pre-miR-26b (Student's t test, two-tailed, *p<0.0005, *p<0.01, n=4).

FIGS. 8A-D: Overexpression of miR-26b or siRNA-mediated knockdown of Rb1 have similar effects in mature cortical neurons transfected at DIV14. (A). Representative western blot analysis (left) and quantification of four independent experiments demonstrate that overexpression of miR-26b increases expression of CCNE1 and phosphorylation of Rb1 at Ser780, and tau at Ser404, whereas p27 is down-regulated (2-way ANOVA, *p<0.05, **p<0.005, n=4). (B) Western blot analysis showing increased cleavage of caspase 3 five days post-transfection with pre-miR-26b (Student's t-test, two-tailed, *p<0.05, n=2). (C) Western blot analysis demonstrating that mature cortical neurons transfected with two siRNAs cognate to Rb1 have increased expression of CCNE1 and phosphorylation of Rb1 at Ser780, and tau at Ser404, whereas p27 is down-regulated. (D) A model of the proposed miR-26b-induced effects on neuronal cell cycle initiation, tau phosphorylation, Cdk5 activity, and apoptosis.

Figure 9:
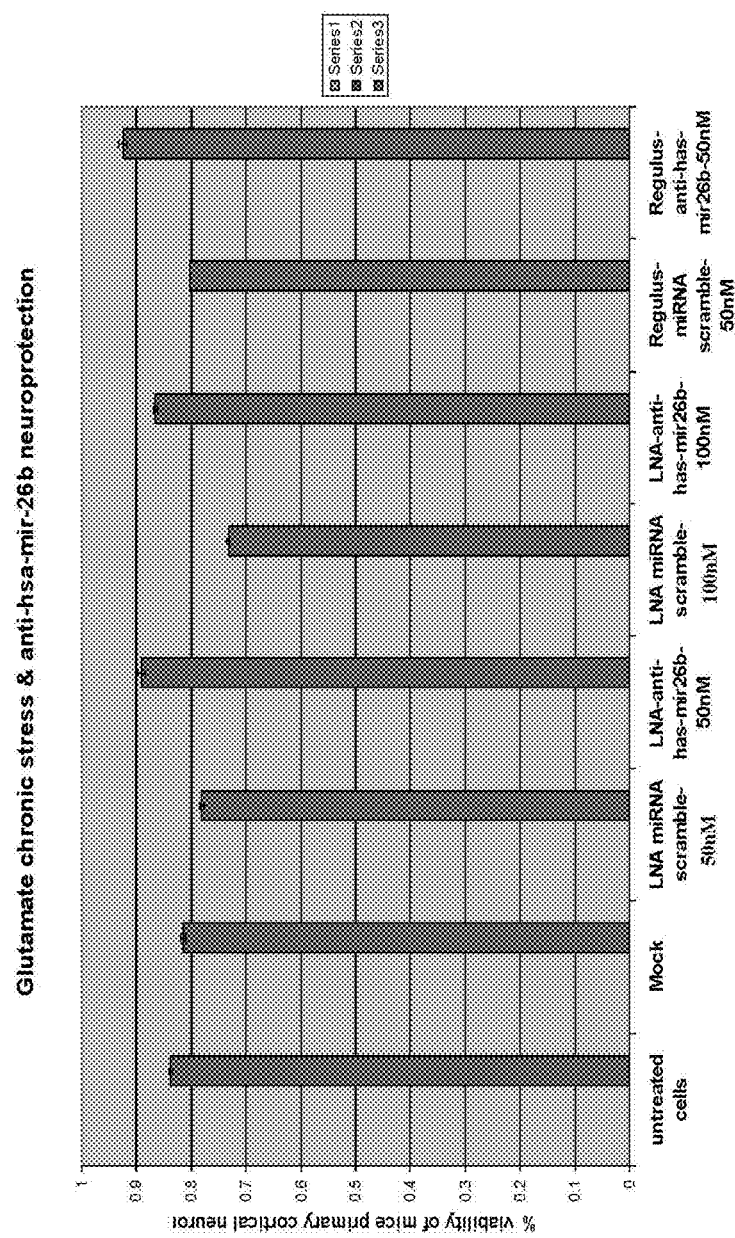

FIG. 9: MiR-26b is neuroprotective in primary cortical and hippocampal neurons. The effects of miR26b on neuron survival were validated in mouse neurons using miRNA inhibitors of different 2'-O-MOE chemistry as indicated. 1, Viability of untreated neurons. P<0.01 for all corresponding pairs control/anti-miR-26.

Figure 10A:
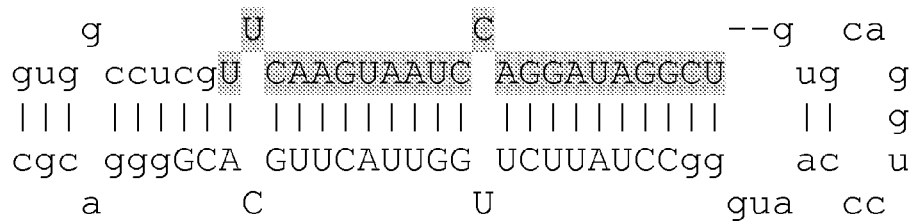
Figure 10B:
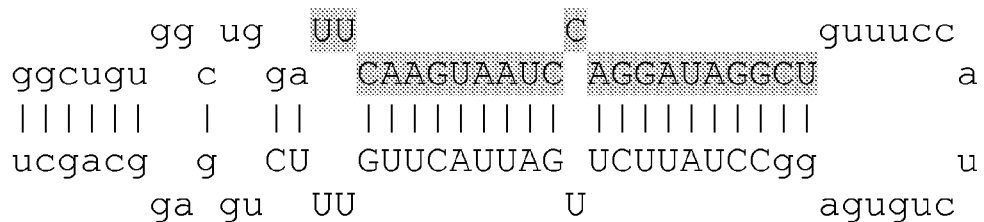
Figure 10C:
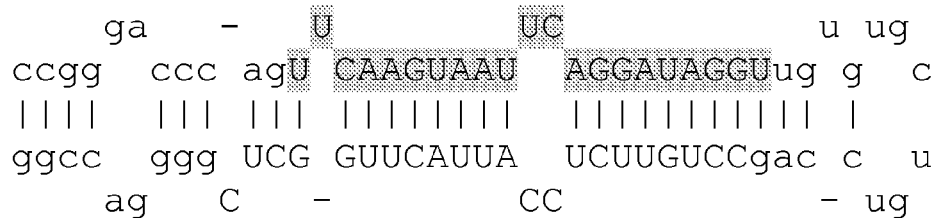

FIGS. 10A-C. Sequences of human miR-26a-1 (10A), miR-26a-2 (10B) and miR-26b (10C) showing hairpin structure of the pre-miR-26a/b; mature sequences are highlighted in grey.

DETAILED DESCRIPTION microRNA (miRNA), a class of small non-coding transcripts, regulates gene expression in various physiological and pathological conditions. miRNAs are important players in various cancers, acting as oncogenes and tumor suppressors (Hammond 2006, Hwang and Mendell 2006). In the mammalian nervous system, miRNA is known to play important roles in development, metabolism, and neural plasticity. Studies have shown that dysregulation of miRNA may play a role in several neurodegenerative diseases (Lau and de Strooper 2010, Provost 2010, Zovoilis et al. 2011) and some key AD proteins are predicted or validated as miRNA targets (Hebert et al. 2008, Hebert et al. 2009, Vilardo et al. 2010, Zhu et al. 2012); however, to date no evidence of miRNA-mediated regulation of AD progression has been demonstrated.

miR-26a/b has been associated with the regulation of cell cycle and apoptosis in cancer cells, acting in different cellular contexts either as a growth-promoting or as a growth-suppressive miRNA (Huse et al., 2009; Kota et al., 2009; Kim et al., 2010; Lu et al., 2011; Zhu et al., 2012a). As demonstrated herein, miR-26b is upregulated in temporal cortex in AD, starting from early prodromal stages, and in postmitotic rodent and human neurons it may induce aberrant CCE, increase tau-phosphorylation, and lead to apoptotic cell death.

It is documented in AD brains that neurons of the hippocampus and cerebral cortex demonstrate appearance of cell cycle markers and partial or full DNA replication. For example a number of cyclins and CDKs, typical for proliferative cells, appear in postmitotic neurons at early stages of AD (Arendt et al., 1998; Smith et al., 1999). Conversely, many cell cycle inhibitors, including p27kip1, are down-regulated in AD (Janicki and Monteiro, 1999). Reports of cell cycle markers preceding other hallmarks of AD (Aβ plaques and NFTs) suggest aberrant CCE in postmitotic neurons may be a causative factor or have a key role in the pathogenesis of the disease (Lopes et al., 2009; Bonda et al., 2010; Swerdlow, 2012). While many vulnerable neurons in AD enter S-phase of the cell cycle, exhibit DNA replication and sometimes binucleation events, M-phase is not entered (Bonda et al., 2009; Moh et al., 2011; Yurov et al., 2011). It is generally accepted that neurons entering the cell cycle are ultimately destined for death; better understanding of how aberrant CCE in postmitotic neurons contributes to AD progression and how it relates to other hallmarks of the disease is vital to help decipher the pathogenesis of AD.

Figure 6A:
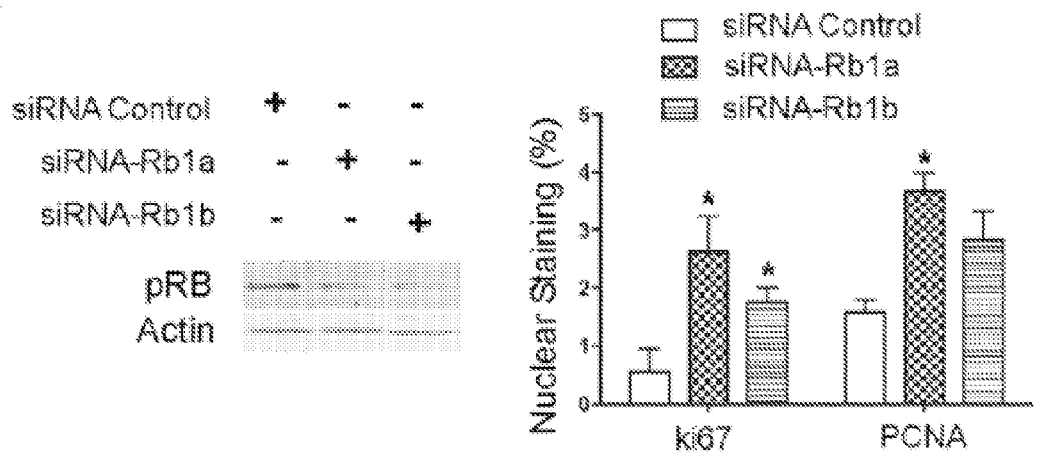
FIGS. 6A-E. Retinoblastoma down-regulation in primary cortical neurons by RNAi leads to induction of cell cycle and apoptosis, and mimics the miR-26b overexpression phenotype. (A) Western blot analysis shows that two different siRNAs for Rb1 (siRNA-Rb1a and siRNA-Rb1b) efficiently reduce pRb1 expression E72 hr post-transfection (left panel). Transfections of neuron cultures with these siRNAs lead to increased nuclear staining for both Ki67 and PCNA (right panel). Histograms depict the percentage of Tuj1$^+$ neurons with the corresponding nuclear staining, counted 5 days post-transfection (Student's t-test, two-tailed, *p<0.05, n=300 neurons). (B) Western blot analysis demonstrates an increase in the expression of cell cycle markers CCNE1, ppRb1 (S807/811) and a decrease in the expression of the cell cycle inhibitor p27 five days post-transfection with siRb1. (C) Histograms depict the percentage of TUNEL positive Tuj1$^+$ neurons 5 days post-transfection (Student's t-test, two-tailed, *p<0.0001, n=300/3). Western blot analysis (right panel) shows up-regulation of cleaved caspase-3 after transfection with siRb1. (D) Cell viability assay demonstrates reduced viability of post-mitotic neurons transfected with two siRNAs cognate to Rb1, 5 days post-transfection (Student's t-test, two-tailed, p<0.001 and ***p<0.0001, n=3). (E) Western blot analysis (left) of γH2A.X 5 d after transfections of pre-miR-Control, pre-miR-26b, siRNA-Rb1a, or siRNA-Rb1b. Quantification of relative γH2A.X levels shows a significant increase in experimentally transfected neurons as compared with pre-miR control transfected (Student's t test, two-tailed, *p<0.05, n=4).
Figure 6B:
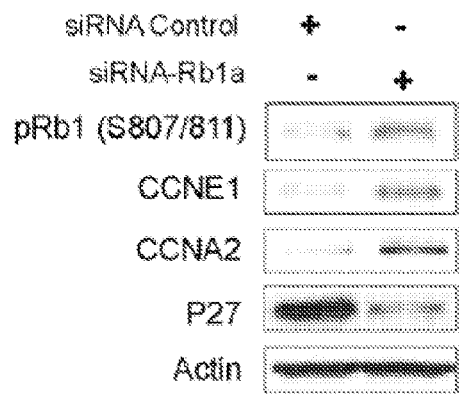

Findings presented herein show that elevation of miR-26b in AD neurons induces cell cycle, directly targets Rb1 and PTEN (among other target genes), and causes activation of Cdk5, leading to tau-phosphorylation followed by apoptosis. Rb1, a key tumor suppressor protein, regulates cell proliferation by controlling progression through the restriction point within the G1-phase of the cell cycle. Hypophosphorylated Rb1 binds and inhibits the transcription factor E2F, which is required for transcription of S-phase genes, while phosphorylation by CDKs inhibits Rb1-E2F binding and thereby allows cell cycle progression. In neurons, Rb1 is expressed at high levels, likely contributing to the postmitotic state of these cells. Remarkably, miR-26b regulates Rb1 directly by binding to Rb1 mRNA and inhibiting its expression and, consequently, indirectly by functional inactivation through its phosphorylation. Similarly, Rb1 down-regulation by siRNA also leads to Rb1 phosphorylation (FIG. 6). Rb1 reduction may lead to phosphorylation of the remaining Rb1 protein by increasing Cdk5 kinase activity (FIG. 7B,C). Activated transcription of established E2F targets such as cyclin E and Cdk2 can also lead to elevation of Cdk2-cyclin E that phosphorylates Rb1, and thereby further drive progression into S-phase (Yoshida et al., 2013).

Figure 5A:
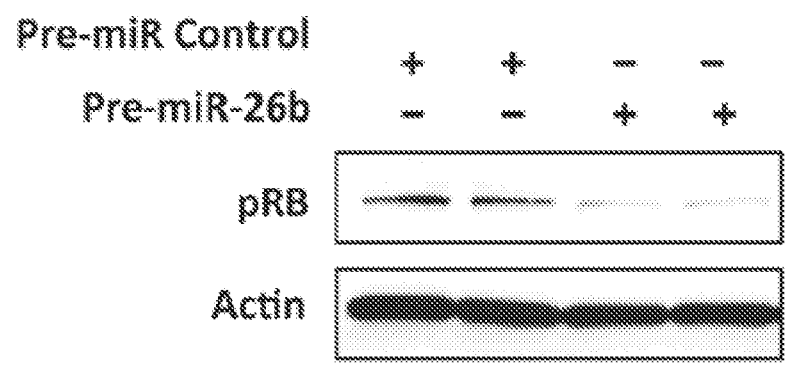
FIGS. 5A-D. Retinoblastoma is a direct target of miR-26b. (A) Western blot analysis shows that miR-26b overexpression down-regulates Rb1 protein in cortical neurons 72-hr post-transfection. (Student's t-test, two-tailed *p<0.0001, n=3). (B) Predicted conserved miR-26b binding sites within the Rb1 3'UTR are shown (top). The nucleotides mutated in the Rb1 3'UTR for the luciferase reporter assays are underlined. Relative luciferase reporter activity of wild-type (wt) or mutant (m) psiCHECK-2-Rb1 3'UTR constructs co-transfected with a precursor pre-miRNA control or pre-miR-26b (50 nM) in cultures primary neurons (bottom). Overexpression of miR-26b led to a significant decrease in the relative activity of a WT but not mutated at site 1 construct, as compared to cells transfected with the pre-miR control (Student's t-test, two-tailed p<0.001 and ***p<0.0001, n=3; error bars represent S.E.M from 3 independent transfections). (C) qRT-PCR analysis of E2F transcriptional targets associated with cell cycle (CCNE1, CCNE2, and PCNA, left panel) and apoptosis (Caspase 8, Apaf1, Map3K14, Map3K5, Caspase3 and Bim, right panel). The quantification reflects expression changes observed 5 days after transfection with pre-miR-26b relative to control. GAPDH served as a normalization housekeeping gene. (Student's t-test, two-tailed, *p<0.05, **p<0.001, n=3). (D) E2F1 downregulation abolishes key effects of miR-26b overexpression. Western blot analysis of neurons cotransfected with siRNA-E2F1 and either pre-miR-26b or pre-miR control demonstrates a decrease in CCNE1 and cleaved caspase 3 and an increase in p27 in neurons cotransfected with siRNA-E2F1 and pre-miR-26b 5 d post-transfection.
Figure 5B:
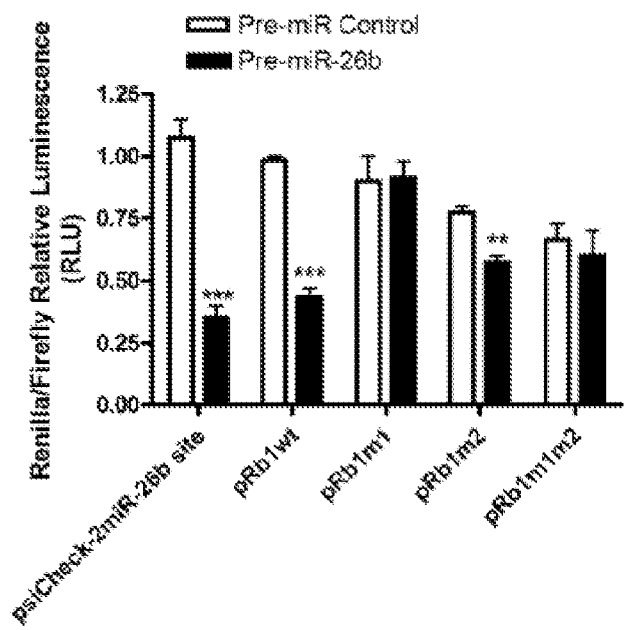
Figure 5C:
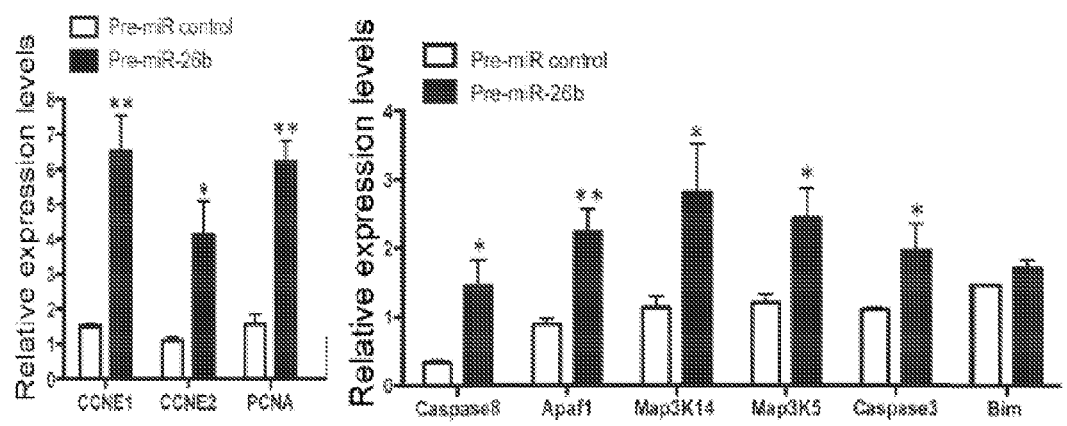
Figure 5D:
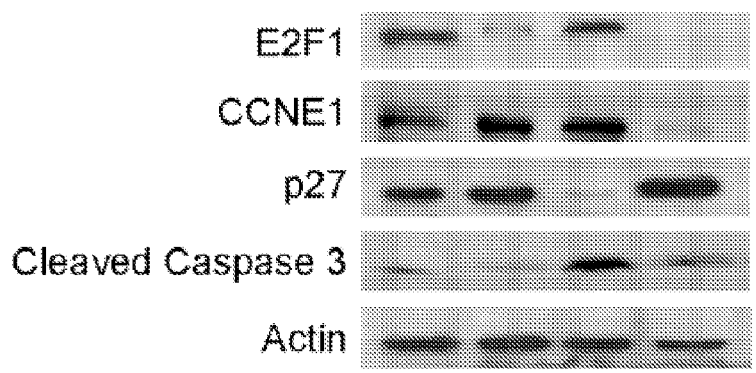

Although, in addition to Rb1, miR-26b may regulate other transcripts, Rb1 appears as the major target in postmitotic neurons as its downregulation by siRNA recapitulated pleiotropic effects (including CCE and apoptosis) induced by miR-26b (FIG. 6). Downregulated Rb1 expression and activity resulted in elevated transcription of E2F target genes, including both S-phase and pro-apoptotic genes, which may provide a direct link between miR-26b-induced CCE and apoptosis. Furthermore, E2F1 silencing abolishes at least some of the key miR-26b-induced effects in neurons (FIG. 5D). Previous studies support the idea of Rb1/E2F pathway coupling CCE and apoptosis, which is often observed in neurons under stress and in neurodegenerative disorders. For example, E2F overexpression in cortical neurons is sufficient to induce apoptosis (Hou et al., 2000), whereas lack of E2F confers protection from death induced by β-amyloid (Giovanni et al., 2000). Overexpression of constitutively active Rb1 protects neurons from death by camptothecin (Park et al., 2000) and after hypoxic insult (Rashidian et al., 2005). Finally, Rb1 conditional knock-out in mice results in a neurodegeneration of adult forebrain neurons, suggesting postmitotic terminally differentiated neurons require Rb1 for continuous cell cycle repression and survival (Andrusiak et al., 2012).

Altered Rb1/E2F expression and activity have been observed in AD. Several studies reported increased phospho-Rb1 immunoreactivity in neurons during the early stages of AD (Jordan-Sciutto et al., 2003; Hoozemans et al., 2005; Thakur et al., 2008). An analysis of the transcriptome of brains with different levels of AD severity established a ~1300 gene signature associated with the disease progression. Notably, more than half of the identified genes (656) were putative E2F transcriptional targets (Gómez Ravetti et al., 2010), further implicating E2F-driven transcription in AD progression.

Effects of miR-26b overexpression in neurons were seen in the strong upregulation of the E2F target CCNE1, and the corresponding downregulation of CCNE1-CDK2 substrate cell cycle inhibitor p27kip1 (FIG. 2). Zhang et al. (2010) identified p27 as a component of nuclear complex blocking neuronal cell cycle. This complex consisting of p27, Cdk5, and p35, binds to E2F1 and prevents its transcriptional activity. P27 is crucial for nuclear retention of this complex; in conditions of p27 deficiency, Cdk5 is not retained in the nucleus and cannot further suppress E2F-driven transcription, thus eliminating cell cycle suppression. Indeed, in miR-26b overexpressing neurons, p27 reduction was accompanied by the corresponding nuclear export of Cdk5 (FIG. 3). Notably, not only cellular localization of Cdk5 changed but also its enzymatic activity significantly increased, as indicated by the amount of Cdk5 coimmunoprecipitated with its activator p25/p35 and the increased phosphorylation of substrates Rb1, tau, and histone H1 (FIG. 7). Importantly, Cdk5 is one of the key tau kinases involved in pathological tau hyperphosphorylation in AD. Indeed, we observed a significant miR-26b-induced increase in tau-phosphorylation at several residues that are Cdk5 epitopes, characteristic for both early and late NFTs, respectively.

In cycling neural and non-neural cells, tau-phosphorylation at AD-related epitopes is cell cycle dependent: it is low in interphase and reaches its peak in mitosis (Preuss et al., 1995; Illenberger et al., 1998). Previous work describes a link between CCE and tau-phosphorylation (Schindowski et al., 2008; Keeney et al., 2012). As shown herein, miR-26b elevation leads to both CCE and tau-phosphorylation in neurons. A similarity between the pattern of tau-phosphorylation in dividing neural cells and neurons degenerating in AD suggests aging neurons respond to inappropriate signals by attempts to enter cell cycle and regenerate, and increased phosphorylation of tau may represent a part of this mechanism.

Frequent coincidents between CCE and hyperphosphorylated tau/NFT in the same neurons have been reported. For example, in AD and other tauopathies, almost all NFT-positive neurons are also positive for PCNA (Busser et al., 1998) or other cell cycle markers (Bonda et al., 2009). In normally aged brain, AD, and several other tauopathies, phosphorylated Rb1 is detected mostly in neurons that exhibit tau pathology and NFTs (Thakur et al., 2008; Stone et al., 2011). Collectively, these data suggest a spatiotemporal, and perhaps also causative link between CCE and tau-phosphorylation, which is most likely mediated through Cdk5: when it is nuclear it blocks the cell cycle, whereas when exported to the cytosol it does not repress the cell cycle and CCE is induced. It also becomes more enzymatically active as a tau kinase, leading to tau hyperphosphorylation. If this is true, stimuli that induce neuronal CCE by removing the Cdk5 nuclear block might also lead to tau hyperphosphorylation. There are studies that support this, e.g., ectopic cell cycle activation by SV40 oncogene in postmitotic neurons in mice display a neurodegenerative phenotype associated by tau pathology and NFT-like profiles (Park et al., 2007). The aberrant CCE accompanied by tau pathology and changes in neuronal cytoskeleton ultimately lead to apoptosis and neurodegeneration.

Figure 8A:
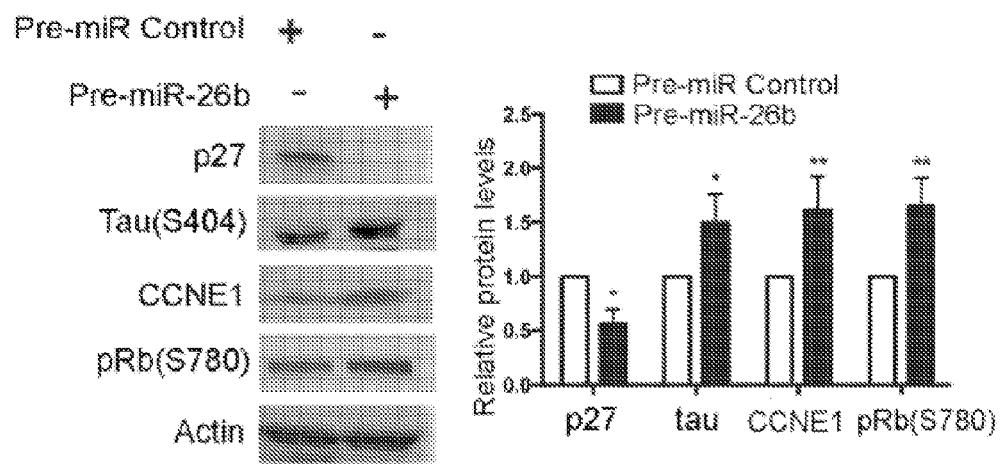
Figure 8B:
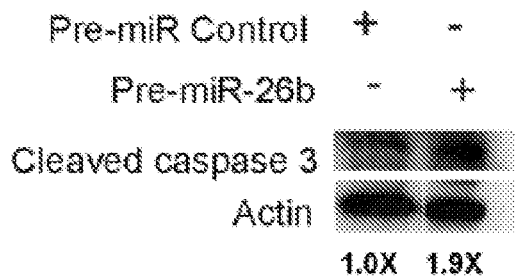
Figure 8C:
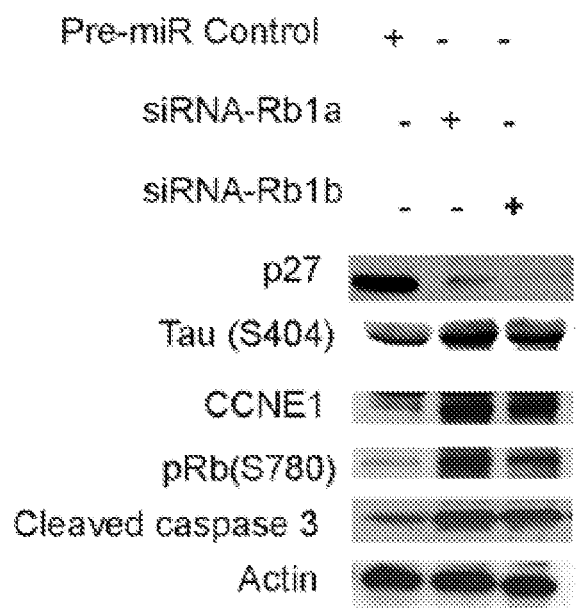
Figure 8D:
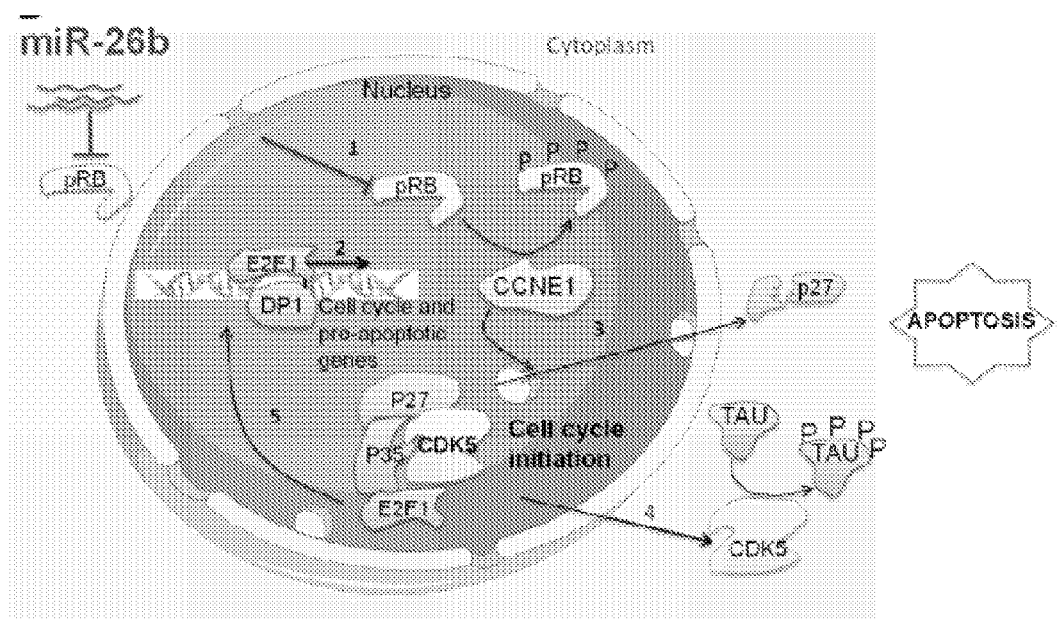

Based on the present data and previous studies outlined above, and without wishing to be bound by theory, the following model of miR-26b function in AD pathogenesis is proposed. miR-26b is upregulated in neurons at early stages of AD/MCI by a yet unknown mechanism. miR-26b directly binds and reduces expression of Rb1, which in turn leads to de-repression of E2F1 and activates transcription of both cell cycle and pro-apoptotic gene targets. Significant increase in CCNE1 may lead to CCNE1/Cdk2-dependent phosphorylation and degradation of p27kip1 (Sheaff et al., 1997; Vlach et al., 1997) followed by the remodeling/dissociation of nuclear p27/Cdk5 complex that normally inhibits cell cycle in neurons. Failure of this block leads to further progression into cell cycle and is accompanied by Cdk5 nuclear export and its increased kinase activity (FIG. 8D). This, in turn, leads to increased phosphorylation of tau and Rb1, thereby further perpetuating cell cycle, inducing expression of pro-apoptotic genes, and altering microtubule dynamics. Collectively, these profound miR-26b-induced alterations in neuronal metabolism ultimately cause death of postmitotic neurons, at least in vitro. Since numerous Rb1/E2F target genes (both drivers of cell cycle drivers and apoptosis) are induced by miR-26b, the precise molecular mechanism remains to be further investigated. The present data suggest miR-26b-induced neuron death, which happens as a consequence of aberrant CCE, induction of pro-apoptotic genes, and tau-hyperphosphorylation, might represent part of the process underlying the pathogenesis of AD and other neurodegenerative diseases. Thus, inhibition of miR-26 is a novel strategy for neuroprotection.

Methods of Treatment

The methods described herein can include the administration of inhibitory nucleic acids that hybridize specifically to miR-26a/b to treat a neurologic or neurodegenerative disease, e.g., Parkinson's disease (PD), Alzheimer's disease (AD), Huntington's disease (HD), brain stroke, brain tumors, cardiac ischemia, age-related macular degeneration (AMD), retinitis pigmentosa (RP), and multiple sclerosis (MS). In some embodiments the neurodegenerative disease is a tauopathy, e.g., a disease associated with the pathological aggregation of tau protein in the human brain (see, e.g., Rizzo et al., Brain 131 (Pt 10): 2690-700 (2008), or a disease associated with glutamate excitotoxicity. Exemplary tauopathies include Alzheimer's disease (AD), frontotemporal dementia (FTD), posttraumatic stress disorders (PTSD), dementia pugilistica, chronic traumatic encephalopathy (CTE), sporadic corticobasal degeneration, progressive supranuclear palsy, and Pick's disease, as well as hereditary frontotemporal dementia and parkinsonism linked to chromosome 17 (FTDP-17); see, e.g., Lee et al., Annu Rev Neurosci. 2001; 24:1121-59; and Lee and Leugers, Prog Mol Biol Transl Sci. 2012; 107:263-93. Diseases associated with glutamate excitotoxicity include AD, Parkinson's disease (PD), Huntington's disease (HD), Amyotrophic Lateral Sclerosis (ALS), and FTD; see, e.g., Farooqui et al., Neurochemical Aspects of Excitotoxicity: Chapter 8, "Glutamate Receptors and Neurological Disorders" (Springer Science & Business Media, 2007); Dong et al., Acta Pharmacologica Sinica 30:379-387 (2009); Butterfield and Pocernich, CNS Drugs. 2003; 17(9):641-52; Donnelly et al., Neuron. 2013 Oct. 16; 80(2):415-28; Gallagher and Schapira et al., Curr Top Med Chem. 2009; 9(10):860-8; Caudle and Zhang, Exp Neurol. 2009 December; 220(2):230-3; Mehta et al., Eur J Pharmacol. 2013 Jan. 5; 698(1-3):6-18. In some embodiments the disease is not ALS.

In some embodiments, the methods include introducing into the cell an oligo that specifically binds, or is complementary, to miR-26a/b. A nucleic acid that "specifically" binds primarily to the target, i.e., to miR-26a/b but not to other non-target RNAs. The specificity of the nucleic acid interaction thus refers to its function (e.g., inhibiting miR-26a/b) rather than its hybridization capacity. Oligos may exhibit nonspecific binding to other sites in the genome or other mRNAs, without interfering with binding of other regulatory proteins and without causing degradation of the non-specifically-bound RNA. Thus this nonspecific binding does not significantly affect function of other non-target RNAs and results in no significant adverse effects. These methods can be used to treat a subject, e.g., a subject with cancer, by administering to the subject a composition (e.g., as described herein) comprising an oligo that binds to a miR-26a/b. Examples of oligos and target sequences are provided herein.

As used herein, treating includes "prophylactic treatment" which means reducing the incidence of or preventing (or reducing risk of) a sign or symptom of a disease in a patient at risk for the disease, and "therapeutic treatment", which means reducing signs or symptoms of a disease, reducing progression of a disease, reducing severity of a disease, in a patient diagnosed with the disease.

In some embodiments, the methods described herein include administering a composition, e.g., a sterile composition, comprising an inhibitory nucleic acid that is complementary to miR-26a/b as described herein Inhibitory nucleic acids for use in practicing the methods described herein are described below.

Inhibitory nucleic acids have been employed as therapeutic moieties in the treatment of disease states in animals, including humans Inhibitory nucleic acids can be useful therapeutic modalities that can be configured to be useful in treatment regimens for the treatment of cells, tissues and animals, especially humans.

For therapeutics, an animal, preferably a human, having a neurodegenerative disorder, suspected of having a neurodegenerative disorder, or at increased risk of developing a neurodegenerative disorder (e.g., by virtue of family history, genetic testing, or presence of other identified risk factor), is treated by administering an inhibitory nucleic acid in accordance with this disclosure. For example, in one non-limiting embodiment, the methods comprise the step of administering to the animal in need of treatment a therapeutically effective amount of an inhibitory nucleic acid as described herein.

Inhibitory Nucleic Acids

In some embodiments, the methods described herein include the administration of a therapeutically effective amount of an inhibitory nucleic acid that targets miR-26a and/or 26b. Although miR-26b is often been referred to herein, in some embodiments, the methods described herein include targeting miR-26a as an alternative to or in addition to miR-26b. The shorthand miR-26a/b is used to refer to targeting either or both of miR-26a and/or miR-26b. In some embodiments, it will be desirable to target only miR-26b, using an antagomiR that blocks only miR-26b.

In general, a sequence of miR-26a/b from the same species as the subject to be treated is used as the target sequence. For example, when treating human subjects, human miR-26a/b is used. In the methods described herein, any of the following can be used as mir-261/b target sequences (e.g., inhibitory nucleic acids can target pri-miR-26a/b or pre-miR-26a/b sequences outside of the mature miR-26a/b).

The sequence of the human miR-26a-1 stem-loop (Chromosome 3; see FIG. 10A) is as follows:

```
                                        (SEQ ID NO: 1)
1-GUGGCCUCGUUCAAGUAAUCCAGGAUAGGCUGUGCAGGU
CCCAAUGGGCCUAUUCUUGGUUACUUGCACGGGGACGC-71
```

The sequence of the human miR-26a-2 stem-loop (Chromosome 12; see FIG. 10B) is as follows:

```
                                        (SEQ ID NO: 2)
1-GGCUGUGGCUGGAUUCAAGUAAUCCAGGAUAGGCUGUU
UCCAUCUGUGAGGCCUAUUCUUGAUUACUUGUUUCUGGAG
GCAGCU-84
```

The mature sequence of human miR-26a (also known as hsa-miR-26a-5p) is as follows (numbering relative to mature miR-26a-1 stem-loop):

```
                                        (SEQ ID NO: 3)
       10-UUCAAGUAAUCCAGGAUAGGCU-31
```

The seed sequence of human miR-26a is as follows:

```
                                        (SEQ ID NO: 4)
                 1-UCAAGU-6
```

The mature sequence of human miR-26a-1* (also known as hsa-miR-26a-1-3-p) is as follows:

```
                                        (SEQ ID NO: 9)
       49-CCUAUUCUUGGUUACUUGCACG-70
```

The sequences of the mature miR-26a (also known as hsa-miR-26a-5p) and miR-26-a1* (also known as hsa-miR-26a-1-3-p) are shown in upper case on FIGS. 10A-10B.

Sequences for miR-26a from other species are known in the art.

The sequence of the human miR-26b stem loop (Chromosome 2; see FIG. 10C) is as follows:

```
                                        (SEQ ID NO: 10)
1-CCGGGACCCAGUUCAAGUAAUUCAGGAUAGGUUGUG
UGCUGUCCAGCCUGUUCUCCAUUACUUGGCUCGGGGAC
CGG-77
```

The mature sequence of human miR-26b (also known as hsa-miR-26b-5p) is as follows (numbering relative to mature miR-26b-1 stem-loop):

```
                                        (SEQ ID NO: 11)
       12-UUCAAGUAAUUCAGGAUAGGU-32
```

The seed sequence of human miR-26b is as follows:

```
                                        (SEQ ID NO: 4)
                 1-UCAAGU-6
```

The mature sequence of human miR-26b* (also known as hsa-miR-26b-3p) is as follows:

47-CCUGUUCUCCAUUACUUGGCUC-68 (SEQ ID NO: 12)

The sequences of the mature miR-26b (also known as hsa-miR-26b-5p) and miR-26b* (also known as hsa-miR-26b-3p) are shown in upper case on FIG. 10C.

Sequences for miR-26b from other species are known in the art.

In some embodiments, the inhibitory nucleic acid is a competitive antagomiR that blocks the ability of miR-26a and/or 26b to bind to the 3'-UTR of target genes, e.g., Rb and/or PTEN.

Inhibitory nucleic acids useful in the present methods and compositions include antisense oligonucleotides, ribozymes, external guide sequence (EGS) oligonucleotides, siRNA compounds, single- or double-stranded RNA interference (RNAi) compounds such as siRNA compounds, modified bases/locked nucleic acids (LNAs), antagomiRs, peptide nucleic acids (PNAs), and other oligomeric compounds or oligonucleotide mimetics which hybridize to at least a portion of the target nucleic acid (i.e., miR-26a, e.g., all or part of any of SEQ ID NOs:1-4 or 9, or miR-26b, e.g., all or part of SEQ ID NOs: 10-12) and modulate its function. In some embodiments, the inhibitory nucleic acids include antisense RNA, antisense DNA, chimeric antisense oligonucleotides, antisense oligonucleotides comprising modified linkages, interference RNA (RNAi), short interfering RNA (siRNA); a micro, interfering RNA (miRNA); a small, temporal RNA (stRNA); or a short, hairpin RNA (shRNA); small RNA-induced gene activation (RNAa); small activating RNAs (saRNAs), or combinations thereof. See, e.g., WO 2010/040112.

In some embodiments, the inhibitory nucleic acids are 5, 6, 7, 8, 9, or 10, e.g., 10 to 50, 13 to 50, or 13 to 30 or more, nucleotides in length. One having ordinary skill in the art will appreciate that this embodies oligonucleotides having antisense portions of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, or any range therewithin. In some embodiments, the oligonucleotides are 7, 8, 9, 10, 11, 12, 13, 14, or 15 nucleotides in length. In some embodiments, the antisense or oligonucleotide compounds of the invention are 12 or 13 to 30 nucleotides in length. One having ordinary skill in the art will appreciate that this embodies inhibitory nucleic acids having antisense portions of 12, 13, 14, 15, 16, 17, 18, 19, 20, 21, 22, 23, 24, 25, 26, 27, 28, 29 or 30 nucleotides in length, or any range therewithin.

In some embodiments, the inhibitory nucleic acids are designed to target a specific region of miR-26a/b. For example, a specific functional region can be targeted, e.g., a region comprising a seed sequence or a region complementary to a target nucleic acid on which the miR-26a or miR-26b acts. For example, the inhibitory nucleic acid can be designed to target nucleotides 2-7 of the mature miR-26a/b, e.g., complementary to UCAAGU (SEQ ID NO:4), e.g., comprise or have the sequence ACTTGA (SEQ ID NO:5). In some embodiments, the inhibitory nucleic acid comprises or has the sequence ATTACTTGA (SEQ ID NO:6); TTACTTGA (SEQ ID NO:7); or TACTTGA (SEQ ID NO:8). See, e.g. US 2009/0298916.

Alternatively or in addition, highly conserved regions can be targeted, e.g., regions identified by aligning sequences from disparate species such as primate (e.g., human) and rodent (e.g., mouse) and looking for regions with high degrees of identity. Percent identity can be determined routinely using basic local alignment search tools (BLAST programs) (Altschul et al., J. Mol. Biol., 1990, 215, 403-410; Zhang and Madden, Genome Res., 1997, 7, 649-656), e.g., using the default parameters.

In some embodiments, the inhibitory nucleic acids are chimeric oligonucleotides that contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA or RNA:RNA hybrids. Chimeric inhibitory nucleic acids of the invention may be formed as composite structures of two or more oligonucleotides, modified oligonucleotides, oligonucleosides and/or oligonucleotide mimetics as described above. Such compounds have also been referred to in the art as hybrids, mixmers (LNAs containing a limited number of LNA monomers in combination with other types of monomers, typically DNA but also RNA or 20-OMe-RNA monomers), or gapmers (oligonucleotides composed of modified segments flanking a central DNA (or phosphorothioate DNA) segment that is resistant to RNase H activity). Representative United States patents that teach the preparation of such hybrid structures comprise, but are not limited to, U.S. Pat. Nos. 5,013,830; 5,149,797; 5, 220,007; 5,256,775; 5,366,878; 5,403,711; 5,491,133; 5,565,350; 5,623,065; 5,652,355; 5,652,356; and 5,700,922, each of which is herein incorporated by reference. See also Kauppinen et al., Drug. Disc. Today: Tech. 2(3):287-290 (2005). In some embodiments, the inhibitory nucleic acids have regions that are double-stranded, see, e.g., Vermuelen et al., RNA. 13(5): 723-30 (2007).

In some embodiments, the inhibitory nucleic acid comprises at least one nucleotide modified at the 2' position of the sugar, most preferably a 2'-O-alkyl, 2'-O-alkyl-O-alkyl or 2'-fluoro-modified nucleotide. In other preferred embodiments, RNA modifications include 2'-fluoro, 2'-amino and 2' O-methyl modifications on the ribose of pyrimidines, abasic residues or an inverted base at the 3' end of the RNA. Such modifications are routinely incorporated into oligonucleotides and these oligonucleotides have been shown to have a higher Tm (i.e., higher target binding affinity) than; 2'-deoxyoligonucleotides against a given target.

A number of nucleotide and nucleoside modifications have been shown to make the oligonucleotide into which they are incorporated more resistant to nuclease digestion than the native oligodeoxynucleotide; these modified oligos survive intact for a longer time than unmodified oligonucleotides. Specific examples of modified oligonucleotides include those comprising modified backbones, for example, phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioate backbones and those with heteroatom backbones, particularly $CH_2$—NH—O—$CH_2$, CH, ~N($CH_3$)~O~$CH_2$ (known as a methylene(methylimino) or MMI backbone], $CH_2$—O—N($CH_3$)—$CH_2$, $CH_2$—N($CH_3$)—N($CH_3$)—$CH_2$ and O—N($CH_3$)—$CH_2$—$CH_2$ backbones, wherein the native phosphodiester backbone is represented as O—P—O—CH); amide backbones (see De Mesmaeker et al. Ace. Chem. Res. 1995, 28:366-374); morpholino backbone structures (see Summerton and Weller, U.S. Pat. No. 5,034,506); peptide nucleic acid (PNA) backbone (wherein the phosphodiester backbone of the oligonucleotide is replaced with a polyamide backbone, the nucleotides being bound directly or indirectly to the aza nitrogen atoms of the polyamide backbone, see Nielsen et al., Science 1991, 254, 1497). Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2; see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455, 233; 5,466,677; 5,476,925; 5,519,126; 5,536,821; 5,541,306; 5,550,111; 5,563, 253; 5,571,799; 5,587,361; and 5,625,050.

Morpholino-based oligomeric compounds are described in Dwaine A. Braasch and David R. Corey, Biochemistry, 2002, 41(14), 4503-4510); Genesis, volume 30, issue 3, 2001; Heasman, J., Dev. Biol., 2002, 243, 209-214; Nasevicius et al., Nat. Genet., 2000, 26, 216-220; Lacerra et al., Proc. Natl. Acad. Sci., 2000, 97, 9591-9596; and U.S. Pat. No. 5,034,506, issued Jul. 23, 1991.

Cyclohexenyl nucleic acid oligonucleotide mimetics are described in Wang et al., J. Am. Chem. Soc., 2000, 122, 8595-8602.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts; see U.S. Pat. Nos. 5,034,506; 5,166,315; 5,185,444; 5,214,134; 5,216,141; 5,235,033; 5,264, 562; 5, 264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

One or more substituted sugar moieties can also be included, e.g., one of the following at the 2' position: OH, SH, SCH$_3$, F, OCN, OCH$_3$ OCH$_3$, OCH$_3$ O(CH$_2$)n CH$_3$, O(CH$_2$)n NH$_2$ or O(CH$_2$)n CH$_3$ where n is from 1 to about 10; Ci to C10 lower alkyl, alkoxyalkoxy, substituted lower alkyl, alkaryl or aralkyl; Cl; Br; CN; CF$_3$; OCF$_3$; O-, S-, or N-alkyl; O-, S-, or N-alkenyl; SOCH$_3$; SO$_2$CH$_3$; ONO$_2$; NO$_2$; N$_3$; NH$_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-methoxyethoxy (2'-0-CH$_2$CH$_2$OCH$_3$, also known as 2'-O-(2-methoxyethyl)) (Martin et al, Helv. Chim. Acta, 1995, 78, 486). Other preferred modifications include 2'-methoxy (2'-0-CH$_3$), 2'-propoxy (2'-OCH$_2$ CH$_2$CH$_3$) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Inhibitory nucleic acids can also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleobases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine and 2,6-diaminopurine. Kornberg, A., DNA Replication, W. H. Freeman & Co., San Francisco, 1980, pp 75-77; Gebeyehu, G., et al. Nucl. Acids Res. 1987, 15:4513). A "universal" base known in the art, e.g., inosine, can also be included. 5-Me-C substitutions have been shown to increase nucleic acid duplex stability by 0.6-1.2<0>C. (Sanghvi, Y. S., in Crooke, S. T. and Lebleu, B., eds., Antisense Research and Applications, CRC Press, Boca Raton, 1993, pp. 276-278) and are presently preferred base substitutions.

It is not necessary for all positions in a given oligonucleotide to be uniformly modified, and in fact more than one of the aforementioned modifications may be incorporated in a single oligonucleotide or even at within a single nucleoside within an oligonucleotide.

In some embodiments, both a sugar and an internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, for example, an aminoethylglycine backbone. The nucleobases are retained and are bound directly or indirectly to aza nitrogen atoms of the amide portion of the backbone. Representative United States patents that teach the preparation of PNA compounds comprise, but are not limited to, U.S. Pat. Nos. 5,539,082; 5,714,331; and 5,719,262, each of which is herein incorporated by reference. Further teaching of PNA compounds can be found in Nielsen et al, Science, 1991, 254, 1497-1500.

Inhibitory nucleic acids can also include one or more nucleobase (often referred to in the art simply as "base") modifications or substitutions. As used herein, "unmodified" or "natural" nucleobases comprise the purine bases adenine (A) and guanine (G), and the pyrimidine bases thymine (T), cytosine (C) and uracil (U). Modified nucleobases comprise other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine and 3-deazaguanine and 3-deazaadenine.

Further, nucleobases comprise those disclosed in U.S. Pat. No. 3,687,808, those disclosed in 'The Concise Encyclopedia of Polymer Science And Engineering', pages 858-859, Kroschwitz, J. I., ed. John Wiley & Sons, 1990, those disclosed by Englisch et al., Angewandle Chemie, International Edition', 1991, 30, page 613, and those disclosed by Sanghvi, Y. S., Chapter 15, Antisense Research and Applications', pages 289-302, Crooke, S. T. and Lebleu, B. ea., CRC Press, 1993. Certain of these nucleobases are particularly useful for increasing the binding affinity of the oligomeric compounds of the invention. These include 5-substituted pyrimidines, 6-azapyrimidines and N-2, N-6 and 0-6 substituted purines, comprising 2-aminopropyladenine, 5-propynyluracil and 5-propynylcytosine. 5-methylcytosine substitutions have been shown to increase nucleic acid duplex stability by 0.6-1.2<0>C (Sanghvi, Y. S., Crooke, S. T. and Lebleu, B., eds, 'Antisense Research and Applications', CRC Press, Boca Raton, 1993, pp. 276-278) and are presently preferred base substitutions, even more particularly when combined with 2'-O-methoxyethyl sugar modifications. Modified nucleobases are described in U.S. Pat. No. 3,687,808, as well as U.S. Pat. Nos. 4,845,205; 5,130, 302; 5,134,066; 5,175, 273; 5, 367,066; 5,432,272; 5,457, 187; 5,459,255; 5,484,908; 5,502,177; 5,525,711; 5,552, 540; 5,587,469; 5,596,091; 5,614,617; 5,750,692, and 5,681,941, each of which is herein incorporated by reference.

In some embodiments, the inhibitory nucleic acids are chemically linked to one or more moieties or conjugates that enhance the activity, cellular distribution, or cellular uptake of the oligonucleotide. Such moieties comprise but are not limited to, lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al, Ann N. Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Mancharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-t oxy-cholesterol moiety (Crooke et al., J. Pharmacol. Exp. Ther., 1996, 277, 923-937). See also U.S. Pat. Nos. 4,828,979; 4,948,882; 5,218,105; 5,525,465; 5,541,313; 5,545,730; 5,552, 538; 5,578,717, 5,580,731; 5,580,731; 5,591,584; 5,109,124; 5,118,802; 5,138,045; 5,414,077; 5,486, 603; 5,512,439; 5,578,718; 5,608,046; 4,587,044; 4,605,735; 4,667,025; 4,762, 779; 4,789,737; 4,824,941; 4,835,263; 4,876,335; 4,904,582; 4,958,013; 5,082, 830; 5,112,963; 5,214,136; 5,082,830; 5,112,963; 5,214,136; 5, 245,022; 5,254,469; 5,258,506; 5,262,536; 5,272,250; 5,292,873; 5,317,098; 5,371,241, 5,391, 723; 5,416,203, 5,451,463; 5,510,475; 5,512,667; 5,514,785; 5, 565,552; 5,567,810; 5,574,142; 5,585,481; 5,587,371; 5,595,726; 5,597,696; 5,599,923; 5,599, 928 and 5,688,941, each of which is herein incorporated by reference.

These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxy cholesterol moiety. See, e.g., U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

The inhibitory nucleic acids useful in the present methods are sufficiently complementary to all or part of miR-26a/b, i.e., hybridize sufficiently well and with sufficient specificity, to give the desired effect. "Complementary" refers to the capacity for pairing, through hydrogen bonding, between two sequences comprising naturally or non-naturally occurring bases or analogs thereof. For example, if a base at one position of an inhibitory nucleic acid is capable of hydrogen bonding with a base at the corresponding position of a miR-26a/b sequence, then the bases are considered to be complementary to each other at that position. 100% complementarity is not required.

In the context of this invention, hybridization means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. Complementary, as used herein, refers to the capacity for precise pairing between two nucleotides. The inhibitory nucleic acids and the miR-26a/b are complementary to each other when a sufficient number of corresponding positions in each molecule are occupied by nucleotides that can hydrogen bond with each other. Thus, "specifically hybridizable" and "complementary" are terms which are used to indicate a sufficient degree of complementarity or precise pairing such that stable and specific binding occurs between the inhibitory nucleic acid and the miR-26a/b target sequence. For example, if a base at one position of an inhibitory nucleic acid is capable of hydrogen bonding with a base at the corresponding position of a miR-26a/b molecule, then the bases are considered to be complementary to each other at that position.

Although in some embodiments, 100% complementarity is desirable, it is understood in the art that a complementary nucleic acid sequence need not be 100% complementary to that of its target nucleic acid to be specifically hybridisable. A complementary nucleic acid sequence for purposes of the present methods is specifically hybridisable when binding of the sequence to the target miR-26a/b molecule interferes with the normal function of the target miR-26a/b to cause a loss of activity, and there is a sufficient degree of complementarity to avoid non-specific binding of the sequence to non-target miR-26a/b sequences under conditions in which specific binding is desired, e.g., under physiological conditions in the case of in vivo assays or therapeutic treatment, and in the case of in vitro assays, under conditions in which the assays are performed under suitable conditions of stringency. For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., *Molecular Cloning: A Laboratory Manual*, Cold Spring Harbor Laboratory Press, New York.

In general, the inhibitory nucleic acids useful in the methods described herein have at least 80% sequence complementarity to a target region within the target nucleic acid, e.g., 90%, 95%, or 100% sequence complementarity to the target region within miR-26a/b (e.g., a target region comprising the seed sequence as described herein). For example, an antisense compound in which 18 of 20 nucleobases of the antisense oligonucleotide are complementary, and would therefore specifically hybridize, to a target region would represent 90 percent complementarity. Percent complementarity of an inhibitory nucleic acid with a region of a target nucleic acid can be determined routinely using basic local alignment search tools (BLAST programs) (Altschul et al., J. Mol. Biol., 1990, 215, 403-410; Zhang and Madden, Genome Res., 1997, 7, 649-656). Antisense and other compounds of the invention that hybridize to a miR-26a/b target sequence are identified through routine experimentation. In general the inhibitory nucleic acids must retain specificity for their target, i.e., must not directly bind to, or directly significantly affect expression levels of, transcripts other than the intended target.

For further disclosure regarding inhibitory nucleic acids, please see US2010/0317718 (antisense oligos); US2010/0249052 (double-stranded ribonucleic acid (dsRNA)); US2009/0181914 and US2010/0234451 (LNAs); US2007/0191294 (siRNA analogues); US2008/0249039 (modified siRNA); and WO2010/129746 and WO2010/040112 (inhibitory nucleic acids).

Antisense

In some embodiments, the inhibitory nucleic acids are antisense oligonucleotides. Antisense oligonucleotides are typically designed to block expression of a DNA or RNA target by binding to the target and halting expression at the level of transcription, translation, or splicing. Antisense oligonucleotides of the present invention are complementary nucleic acid sequences designed to hybridize under stringent conditions to a miR-26a/b target sequence. Thus, oligonucleotides are chosen that are sufficiently complementary to the target, i.e., that hybridize sufficiently well and with sufficient specificity, to give the desired effect.

Modified Bases/Locked Nucleic Acids (LNAs)

In some embodiments, the inhibitory nucleic acids used in the methods described herein comprise one or more modified bonds or bases. Modified bases include phosphorothioate, methylphosphonate, peptide nucleic acids, or locked nucleic acid (LNA) molecules. Preferably, the modified nucleotides are locked nucleic acid molecules, including [alpha]-L-LNAs. LNAs comprise ribonucleic acid analogues wherein the ribose ring is "locked" by a methylene bridge between the 2'-oxygen and the 4'-carbon—i.e., oligonucleotides containing at least one LNA monomer, that is, one 2'-O,4'-C-methylene-β-D-ribofuranosyl nucleotide. LNA bases form standard Watson-Crick base pairs but the locked configuration increases the rate and stability of the basepairing reaction (Jepsen et al., Oligonucleotides, 14, 130-146 (2004)). LNAs also have increased affinity to base pair with RNA as compared to DNA. These properties render LNAs especially useful as probes for fluorescence in situ hybridization (FISH) and comparative genomic hybridization, as knockdown tools for miRNAs, and as antisense oligonucleotides to target mRNAs or other RNAs.

The LNA molecules can include molecules comprising 10-30, e.g., 12-24, e.g., 12, 13, 14, 15, 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a miR-26a/b target sequence. The LNA molecules can be chemically synthesized using methods known in the art.

The LNA molecules can be designed using any method known in the art; a number of algorithms are known, and are commercially available (e.g., on the internet, for example at exiqon.com). See, e.g., You et al., Nuc. Acids. Res. 34:e60 (2006); McTigue et al., Biochemistry 43:5388-405 (2004); and Levin et al., Nuc. Acids. Res. 34:e142 (2006). For example, "gene walk" methods, similar to those used to design antisense oligos, can be used to optimize the inhibitory activity of the LNA (or any other inhibitory nucleic acid described herein); for example, a series of oligonucleotides of 7- or 10-30 nucleotides spanning the length of a target miR-26a/b sequence can be prepared, followed by testing for activity. Optionally, gaps, e.g., of 5-10 nucleotides or more, can be left between the LNAs to reduce the number of oligonucleotides synthesized and tested. GC content is preferably between about 30-60%. General guidelines for designing LNAs are known in the art; for example, LNA sequences will bind very tightly to other LNA sequences, so it is preferable to avoid significant complementarity within an LNA. Contiguous runs of three or more Gs or Cs, or more than four LNA residues, should be avoided where possible (for example, it may not be possible with very short (e.g., about 9-10 nt) oligonucleotides). In some embodiments, the LNAs are xylo-LNAs.

For additional information regarding LNAs see U.S. Pat. Nos. 6,268,490; 6,734,291; 6,770,748; 6,794,499; 7,034,133; 7,053,207; 7,060,809; 7,084,125; and 7,572,582; and U.S. Pre-Grant Pub. Nos. 20100267018; 20100261175; and 20100035968; Koshkin et al. Tetrahedron 54, 3607-3630 (1998); Obika et al. Tetrahedron Lett. 39, 5401-5404 (1998); Jepsen et al., Oligonucleotides 14:130-146 (2004); Kauppinen et al., Drug Disc. Today 2(3):287-290 (2005); and Ponting et al., Cell 136(4):629-641 (2009), and references cited therein.

In some embodiments of the methods described herein, the inhibitory nucleic acid is or comprises ACTTGA (SEQ ID NO:5) wherein all of the nucleic acids are locked and the backbone is a phosphorothioate backbone.

Antagomirs

In some embodiments, the antisense is an antagomiR. Antagomirs are chemically modified antisense oligonucleotides that target a miR-26a/b target sequence. For example, an antagomiR for use in the methods described herein can include a nucleotide sequence sufficiently complementary to hybridize to a miR-26a/b target sequence of about 12 to 25 nucleotides, preferably about 15 to 23 nucleotides.

In general, antagomiRs include a cholesterol moiety, e.g., at the 3'-end. In some embodiments, antagomiRs have various modifications for RNase protection and pharmacologic properties such as enhanced tissue and cellular uptake. For example, In addition to the modifications discussed above for antisense oligos, an antagomiR can have one or more of complete or partial 2'-O-methylation of sugar and/or a phosphorothioate backbone. Phosphorothioate modifications provide protection against RNase activity and their lipophilicity contributes to enhanced tissue uptake. In some embodiments, the antagomiR can include six phosphorothioate backbone modifications; two phosphorothioates are located at the 5'-end and four at the 3'-end. See, e.g., Krutzfeldt et al., Nature 438, 685-689 (2005); Czech, N Engl J Med 2006; 354:1194-1195 (2006); Robertson et al., Silence. 1:10 (2010); Marquez and McCaffrey, Hum Gene Ther. 19(1):27-38 (2008); van Rooij et al., Circ Res. 103 (9):919-928 (2008); and Liu et al., Int. J. Mol. Sci. 9:978-999 (2008). Antagomirs useful in the present methods can also be modified with respect to their length or otherwise the number of nucleotides making up the antagomiR. The antagomiRs must retain specificity for their target, i.e., must not directly bind to, or directly significantly affect expression levels of, transcripts other than the intended target.

In some embodiments, the inhibitory nucleic acid is locked and includes a cholesterol moiety (e.g., a locked antagomiR).

siRNA/shRNA

In some embodiments, the nucleic acid sequence that is complementary to miR-26a/b can be an interfering RNA, including but not limited to a small interfering RNA ("siRNA") or a small hairpin RNA ("shRNA"). Methods for constructing interfering RNAs are well known in the art. For example, the interfering RNA can be assembled from two separate oligonucleotides, where one strand is the sense strand and the other is the antisense strand, wherein the antisense and sense strands are self-complementary (i.e., each strand comprises nucleotide sequence that is complementary to nucleotide sequence in the other strand; such as where the antisense strand and sense strand form a duplex or double stranded structure); the antisense strand comprises nucleotide sequence that is complementary to a nucleotide sequence in a target nucleic acid molecule or a portion thereof (i.e., an undesired gene) and the sense strand comprises nucleotide sequence corresponding to the target nucleic acid sequence or a portion thereof. Alternatively, interfering RNA is assembled from a single oligonucleotide, where the self-complementary sense and antisense regions are linked by means of nucleic acid based or non-nucleic acid-based linker(s). The interfering RNA can be a polynucleotide with a duplex, asymmetric duplex, hairpin or asymmetric hairpin secondary structure, having self-complementary sense and antisense regions, wherein the antisense region comprises a nucleotide sequence that is complementary to nucleotide sequence in a separate target nucleic acid molecule or a portion thereof and the sense region having nucleotide sequence corresponding to the target nucleic acid sequence or a portion thereof. The interfering can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siRNA molecule capable of mediating RNA interference.

In some embodiments, the interfering RNA coding region encodes a self-complementary RNA molecule having a sense region, an antisense region and a loop region. Such an RNA molecule when expressed desirably forms a "hairpin" structure, and is referred to herein as an "shRNA." The loop region is generally between about 2 and about 10 nucleotides in length. In some embodiments, the loop region is from about 6 to about 9 nucleotides in length. In some embodiments, the sense region and the antisense region are between about 15 and about 20 nucleotides in length. Following post-transcriptional processing, the small hairpin RNA is converted into a siRNA by a cleavage event mediated by the enzyme Dicer, which is a member of the RNase III family. The siRNA is then capable of inhibiting the expression of a gene with which it shares homology. For details, see Brummelkamp et al., Science 296:550-553, (2002); Lee et al, Nature Biotechnol., 20, 500-505, (2002); Miyagishi and Taira, Nature Biotechnol 20:497-500, (2002); Paddison et al. Genes & Dev. 16:948-958, (2002); Paul, Nature Biotechnol, 20, 505-508, (2002); Sui, Proc. Natl. Acad. Sd. USA, 99(6), 5515-5520, (2002); Yu et al. Proc Natl Acad Sci USA 99:6047-6052, (2002).

The target RNA cleavage reaction guided by siRNAs is highly sequence specific. In general, siRNA containing a nucleotide sequences identical to a portion of the target nucleic acid are preferred for inhibition. However, 100% sequence identity between the siRNA and the target gene is not required to practice the present invention. Thus the invention has the advantage of being able to tolerate sequence variations that might be expected due to genetic mutation, strain polymorphism, or evolutionary divergence. For example, siRNA sequences with insertions, deletions, and single point mutations relative to the target sequence have also been found to be effective for inhibition. Alternatively, siRNA sequences with nucleotide analog substitutions or insertions can be effective for inhibition. In general the siRNAs must retain specificity for their target, i.e., must not directly bind to, or directly significantly affect expression levels of, transcripts other than the intended target.

Ribozymes

Trans-cleaving enzymatic nucleic acid molecules can also be used; they have shown promise as therapeutic agents for human disease (Usman & McSwiggen, 1995 Ann Rep. Med. Chem. 30, 285-294; Christoffersen and Man, 1995 J. Med. Chem. 38, 2023-2037). Enzymatic nucleic acid molecules can be designed to cleave miR-26a/b within the background of cellular RNA. Such a cleavage event renders the miR-26a/b non-functional.

In general, enzymatic nucleic acids with RNA cleaving activity act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

Several approaches such as in vitro selection (evolution) strategies (Orgel, 1979, Proc. R. Soc. London, B 205, 435) have been used to evolve new nucleic acid catalysts capable of catalyzing a variety of reactions, such as cleavage and ligation of phosphodiester linkages and amide linkages, (Joyce, 1989, Gene, 82, 83-87; Beaudry et al., 1992, Science 257, 635-641; Joyce, 1992, Scientific American 267, 90-97; Breaker et al, 1994, TIBTECH 12, 268; Bartel et al, 1993, Science 261:1411-1418; Szostak, 1993, TIBS 17, 89-93; Kumar et al, 1995, FASEB J., 9, 1183; Breaker, 1996, Curr. Op. Biotech., 1, 442)

Making and Using Inhibitory Nucleic Acids

The nucleic acid sequences used to practice the methods described herein, whether RNA, cDNA, genomic DNA, vectors, viruses or hybrids thereof, can be isolated from a variety of sources, genetically engineered, amplified, and/or expressed/generated recombinantly. Recombinant nucleic acid sequences can be individually isolated or cloned and tested for a desired activity. Any recombinant expression system can be used, including e.g. in vitro, bacterial, fungal, mammalian, yeast, insect or plant cell expression systems.

Inhibitory nucleic acids can be inserted into delivery vectors and expressed from transcription units within the vectors. The recombinant vectors can be DNA plasmids or viral vectors. Generation of the vector construct can be accomplished using any suitable genetic engineering techniques well known in the art, including, without limitation, the standard techniques of PCR, oligonucleotide synthesis, restriction endonuclease digestion, ligation, transformation, plasmid purification, and DNA sequencing, for example as described in Sambrook et al. Molecular Cloning: A Laboratory Manual. (1989)), Coffin et al. (Retroviruses. (1997)) and "RNA Viruses: A Practical Approach" (Alan J. Cann, Ed., Oxford University Press, (2000)). As will be apparent to one of ordinary skill in the art, a variety of suitable vectors are available for transferring nucleic acids of the invention into cells. The selection of an appropriate vector to deliver nucleic acids and optimization of the conditions for insertion of the selected expression vector into the cell, are within the scope of one of ordinary skill in the art without the need for undue experimentation. Viral vectors comprise a nucleotide sequence having sequences for the production of recombinant virus in a packaging cell. Viral vectors expressing nucleic acids of the invention can be constructed based on viral backbones including, but not limited to, a retrovirus, lentivirus, adenovirus, adeno-associated virus, pox virus or alphavirus. The recombinant vectors capable of expressing the nucleic acids of the invention can be delivered as described herein, and persist in target cells (e.g., stable transformants).

Inhibitory nucleic acid sequences useful in the present methods can also be synthesized in vitro by well-known chemical synthesis techniques, as described in, e.g., Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066.

Inhibitory nucleic acids useful in the methods described herein can be stabilized against nucleolytic degradation such as by the incorporation of a modification, e.g., a nucleotide modification. For example, nucleic acid sequences of the invention includes a phosphorothioate at least the first, second, or third internucleotide linkage at the 5' or 3' end of the nucleotide sequence. As another example, the nucleic acid sequence can include a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA). As another example, the nucleic acid sequence can include at least one 2'-O-methyl-modified nucleotide, and in some embodiments, all of the nucleotides include a 2'-O-methyl modification. In some embodiments, the nucleic acids are "locked," i.e., comprise nucleic acid analogues in which the ribose ring is "locked" by a methylene bridge connecting the 2'-O atom and the 4'-C atom (see, e.g., Kaupinnen et al., Drug Disc. Today 2(3):287-290 (2005); Koshkin et al., J. Am. Chem. Soc., 120(50):13252-13253 (1998)). For additional modifications see US 2010/0004320, US 2009/0298916, and US 2009/0143326.

Techniques for the manipulation of nucleic acids used to practice this invention, such as, e.g., subcloning, labeling probes (e.g., random-primer labeling using Klenow polymerase, nick translation, amplification), sequencing, hybridization and the like are well described in the scientific and patent literature, see, e.g., Sambrook et al., *Molecular Cloning; A Laboratory Manual* 3d ed. (2001); *Current Protocols in Molecular Biology*, Ausubel et al., eds. (John Wiley & Sons, Inc., New York 2010); Kriegler, *Gene Transfer and Expression: A Laboratory Manual* (1990); *Laboratory Techniques In Biochemistry And Molecular Biology: Hybridization With Nucleic Acid Probes, Part I. Theory and Nucleic Acid Preparation*, Tijssen, ed. Elsevier, N.Y. (1993).

Pharmaceutical Compositions

The methods described herein can include the administration of pharmaceutical compositions and formulations comprising inhibitory nucleic acid sequences designed to target miR-26a/b.

In some embodiments, the compositions are formulated with a pharmaceutically acceptable carrier. The pharmaceutical compositions can be formulated to be administered parenterally, topically, orally or by local administration, such as by aerosol or transdermally. The pharmaceutical compositions can be formulated in any way and can be administered in a variety of unit dosage forms depending upon the condition or disease and the degree of illness, the general medical condition of each patient, the resulting preferred method of administration and the like. Details on techniques for formulation and administration of pharmaceuticals are well described in the scientific and patent literature, see, e.g., *Remington: The Science and Practice of Pharmacy*, 21st ed., 2005.

The inhibitory nucleic acids can be administered alone or as a component of a pharmaceutical formulation (composition). The compounds may be formulated for administration, in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of the compositions of the invention include those suitable for intradermal, inhalation, oral/nasal, topical, parenteral, rectal, and/or intravaginal administration. The formulations may conveniently be presented in unit dosage form and may be prepared by any methods well known in the art of pharmacy. The amount of active ingredient (e.g., nucleic acid sequences of this invention) which can be combined with a carrier material to produce a single dosage form will vary depending upon the host being treated, the particular mode of administration, e.g., intradermal or inhalation. The amount of active ingredient which can be combined with a carrier material to produce a single dosage form will generally be that amount of the compound which produces a therapeutic effect, e.g., an antigen specific T cell or humoral response.

Pharmaceutical formulations of this invention can be prepared according to any method known to the art for the manufacture of pharmaceuticals. Such drugs can contain sweetening agents, flavoring agents, coloring agents and preserving agents. A formulation can be admixtured with nontoxic pharmaceutically acceptable excipients which are suitable for manufacture. Formulations may comprise one or more diluents, emulsifiers, preservatives, buffers, excipients, etc. and may be provided in such forms as liquids, powders, emulsions, lyophilized powders, sprays, creams, lotions, controlled release formulations, tablets, pills, gels, on patches, in implants, etc.

Pharmaceutical formulations for oral administration can be formulated using pharmaceutically acceptable carriers well known in the art in appropriate and suitable dosages. Such carriers enable the pharmaceuticals to be formulated in unit dosage forms as tablets, pills, powder, dragees, capsules, liquids, lozenges, gels, syrups, slurries, suspensions, etc., suitable for ingestion by the patient. Pharmaceutical preparations for oral use can be formulated as a solid excipient, optionally grinding a resulting mixture, and processing the mixture of granules, after adding suitable additional compounds, if desired, to obtain tablets or dragee cores. Suitable solid excipients are carbohydrate or protein fillers include, e.g., sugars, including lactose, sucrose, mannitol, or sorbitol; starch from corn, wheat, rice, potato, or other plants; cellulose such as methyl cellulose, hydroxypropylmethyl-cellulose, or sodium carboxy-methylcellulose; and gums including arabic and tragacanth; and proteins, e.g., gelatin and collagen. Disintegrating or solubilizing agents may be added, such as the cross-linked polyvinyl pyrrolidone, agar, alginic acid, or a salt thereof, such as sodium alginate. Push-fit capsules can contain active agents mixed with a filler or binders such as lactose or starches, lubricants such as talc or magnesium stearate, and, optionally, stabilizers. In soft capsules, the active agents can be dissolved or suspended in suitable liquids, such as fatty oils, liquid paraffin, or liquid polyethylene glycol with or without stabilizers.

Aqueous suspensions can contain an active agent (e.g., nucleic acid sequences of the invention) in admixture with excipients suitable for the manufacture of aqueous suspensions, e.g., for aqueous intradermal injections. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

In some embodiments, oil-based pharmaceuticals are used for administration of nucleic acid sequences of the invention. Oil-based suspensions can be formulated by suspending an active agent in a vegetable oil, such as arachis oil, olive oil, sesame oil or coconut oil, or in a mineral oil such as liquid paraffin; or a mixture of these. See e.g., U.S. Pat. No. 5,716,928 describing using essential oils or essential oil components for increasing bioavailability and reducing inter- and intra-individual variability of orally administered hydrophobic pharmaceutical compounds (see also U.S. Pat. No. 5,858,401). The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto (1997) J. Pharmacol. Exp. Ther. 281:93-102.

Pharmaceutical formulations can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent. In alternative embodiments, these injectable oil-in-water emulsions of the invention comprise a paraffin oil, a sorbitan monooleate, an ethoxylated sorbitan monooleate and/or an ethoxylated sorbitan trioleate.

The pharmaceutical compounds can also be administered by intranasal, intracranial, intrathecal, intraocular and intravaginal routes including implantable pumps (e.g., CEDs), suppositories, insufflation, powders and aerosol formulations (for examples of steroid inhalants, see e.g., Rohatagi (1995) J. Clin. Pharmacol. 35:1187-1193; Tjwa (1995) Ann Allergy Asthma Immunol. 75:107-111). Suppositories formulations can be prepared by mixing the drug with a suitable non-irritating excipient which is solid at ordinary temperatures but liquid at body temperatures and will therefore melt in the body to release the drug. Such materials are cocoa butter and polyethylene glycols.

In some embodiments, the pharmaceutical compounds can be delivered transdermally, by a topical route, formulated as applicator sticks, solutions, suspensions, emulsions, gels, creams, ointments, pastes, jellies, paints, powders, and aerosols.

In some embodiments, the pharmaceutical compounds can also be delivered as microspheres for slow release in the body. For example, microspheres can be administered via intradermal injection of drug which slowly release subcutaneously; see Rao (1995) J. Biomater. Sci. Polym. Ed. 7:623-645; as biodegradable and injectable gel formulations, see, e.g., Gao (1995) Pharm. Res. 12:857-863 (1995); or, as microspheres for oral administration, see, e.g., Eyles (1997) J. Pharm. Pharmacol. 49:669-674.

In some embodiments, the pharmaceutical compounds can be parenterally administered, such as by intravenous (IV) administration or administration into a body cavity or lumen of an organ, or by intracoronary administration. These formulations can comprise a solution of active agent dissolved in a pharmaceutically acceptable carrier. Acceptable vehicles and solvents that can be employed are water and Ringer's solution, an isotonic sodium chloride. In addition, sterile fixed oils can be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of active agent in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated using those suitable dispersing or wetting agents and suspending agents. The sterile injectable preparation can also be a suspension in a nontoxic parenterally-acceptable diluent or solvent, such as a solution of 1,3-butanediol. The administration can be by bolus or continuous infusion (e.g., substantially uninterrupted introduction into a blood vessel for a specified period of time).

In some embodiments, the pharmaceutical compounds and formulations can be lyophilized. Stable lyophilized formulations comprising an inhibitory nucleic acid can be made by lyophilizing a solution comprising a pharmaceutical of the invention and a bulking agent, e.g., mannitol, trehalose, raffinose, and sucrose or mixtures thereof. A process for preparing a stable lyophilized formulation can include lyophilizing a solution about 2.5 mg/mL protein, about 15 mg/mL sucrose, about 19 mg/mL NaCl, and a sodium citrate buffer having a pH greater than 5.5 but less than 6.5. See, e.g., U.S. 20040028670.

The compositions and formulations can be delivered by the use of liposomes. By using liposomes, particularly where the liposome surface carries ligands specific for target cells, or are otherwise preferentially directed to a specific organ, one can focus the delivery of the active agent into target cells in vivo. See, e.g., U.S. Pat. Nos. 6,063,400; 6,007,839; Al-Muhammed (1996) J. Microencapsul. 13:293-306; Chonn (1995) Curr. Opin. Biotechnol. 6:698-708; Ostro (1989) Am. J. Hosp. Pharm. 46:1576-1587. As used in the present invention, the term "liposome" means a vesicle composed of amphiphilic lipids arranged in a bilayer or bilayers. Liposomes are unilamellar or multilamellar vesicles that have a membrane formed from a lipophilic material and an aqueous interior that contains the composition to be delivered. Cationic liposomes are positively charged liposomes that are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes can also include "sterically stabilized" liposomes, i.e., liposomes comprising one or more specialized lipids. When incorporated into liposomes, these specialized lipids result in liposomes with enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860.

The formulations of the invention can be administered for prophylactic and/or therapeutic treatments. In some embodiments, for therapeutic applications, compositions are administered to a subject who is need of reduced triglyceride levels, or who is at risk of or has a disorder described herein, in an amount sufficient to cure, alleviate or partially arrest the clinical manifestations of the disorder or its complications; this can be called a therapeutically effective amount. For example, in some embodiments, pharmaceutical compositions of the invention are administered in an amount sufficient to decrease serum levels of triglycerides in the subject.

The amount of pharmaceutical composition adequate to accomplish this is a therapeutically effective dose. The dosage schedule and amounts effective for this use, i.e., the dosing regimen, will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the active agents' rate of absorption, bioavailability, metabolism, clearance, and the like (see, e.g., Hidalgo-Aragones (1996) J. Steroid Biochem. Mol. Biol. 58:611-617; Groning (1996) Pharmazie 51:337-341; Fotherby (1996) Contraception 54:59-69; Johnson (1995) J. Pharm. Sci. 84:1144-1146; Rohatagi (1995) Pharmazie 50:610-613; Brophy (1983) Eur. J. Clin. Pharmacol. 24:103-108; *Remington: The Science and Practice of Pharmacy,* 21st ed., 2005). The state of the art allows the clinician to determine the dosage regimen for each individual patient, active agent and disease or condition treated. Guidelines provided for similar compositions used as pharmaceuticals can be used as guidance to determine the dosage regiment, i.e., dose schedule and dosage levels, administered practicing the methods of the invention are correct and appropriate.

Single or multiple administrations of formulations can be given depending on for example: the dosage and frequency as required and tolerated by the patient, the degree and amount of therapeutic effect generated after each administration (e.g., effect on tumor size or growth), and the like. The formulations should provide a sufficient quantity of active agent to effectively treat, prevent or ameliorate conditions, diseases or symptoms.

In alternative embodiments, pharmaceutical formulations for oral administration are in a daily amount of between about 1 to 100 or more mg per kilogram of body weight per day. Lower dosages can be used, in contrast to administration orally, into the blood stream, into a body cavity or into a lumen of an organ. Substantially higher dosages can be used in topical or oral administration or administering by powders, spray or inhalation. Actual methods for preparing parenterally or non-parenterally administrable formulations will be known or apparent to those skilled in the art and are described in more detail in such publications as *Remington: The Science and Practice of Pharmacy,* 21st ed., 2005.

Various studies have reported successful mammalian dosing using complementary nucleic acid sequences. For example, Esau C., et al., (2006) Cell Metabolism, 3(2):87-98 reported dosing of normal mice with intraperitoneal doses of miR-122 antisense oligonucleotide ranging from 12.5 to 75 mg/kg twice weekly for 4 weeks. The mice appeared healthy and normal at the end of treatment, with no loss of body weight or reduced food intake. Plasma transaminase levels were in the normal range (AST ¾ 45, ALT ¾ 35) for all doses with the exception of the 75 mg/kg dose of miR-122 ASO, which showed a very mild increase in ALT and AST levels. They concluded that 50 mg/kg was an effective, non-toxic dose. Another study by Krützfeldt J., et al., (2005) Nature 438, 685-689, injected antagomiRs to silence miR-122 in mice using a total dose of 80, 160 or 240 mg per kg body weight. The highest dose resulted in a complete loss of miR-122 signal. In yet another study, locked nucleic acids ("LNAs") were successfully applied in primates to silence miR-122. Elmen J., et al., (2008) Nature 452, 896-899, report that efficient silencing of miR-122 was achieved in primates by three doses of 10 mg kg-1 LNA-anti-miR, leading to a long-lasting and reversible decrease in total plasma cholesterol without any evidence for LNA-associated toxicities or histopathological changes in the study animals.

In some embodiments, the methods described herein can include co-administration or co-formulation with other drugs or pharmaceuticals, e.g., compositions for treating a neurodegenerative disorder. For example, the inhibitory nucleic acids can be co-administered with drugs for treating or reducing risk of Alzheimer's disease, e.g., donepezil, galantamine, memantine, rivastigmine, or tacrine. Cholinesterase inhibitors (Aricept, Exelon, Razadyne, Cognex) and memantine (Namenda) can be used, e.g., to treat the cognitive symptoms (memory loss, confusion, and problems with thinking and reasoning) of the neurodegenerative disorder, e.g., Alzheimer's disease. In addition, one or more treatments for behavioral changes associated with the neurodegenerative disorder, e.g., Alzheimer's disease, can be administered, including one or more antidepressants for low mood and irritability (e.g., citalopram (Celexa); fluoxetine (Prozac); paroxeine (Paxil); sertraline (Zoloft); or trazodone (Desyrel); anxiolytics for anxiety, verbally disruptive behavior, restlessness, and resistance (e.g., lorazepam (Ativan) or oxazepam (Serax)); antipsychotic medications to treat symptoms including aggression, hallucinations, delusions, agitation, hostility and uncooperativeness (e.g., aripiprazole (Abilify); clozapine (Clozaril); haloperidol (Haldol), olanzapine (Zyprexa); quetiapine (Seroquel); risperidone (Risperdal); or ziprasidone (Geodon)).

EXAMPLES

The invention is further described in the following examples, which do not limit the scope of the invention described in the claims.

Example 1

MiR-26b, Up-Regulated in Alzheimer's Disease, Activates Cell Cycle Entry, Tau-Phosphorylation and Apoptosis in Post-Mitotic Neurons The following example describes experiments identifying miR-26, e.g., miR-26b, as having an important role in AD pathogenesis.

Experimental Procedures

The following materials and methods were used in the Examples.

Materials.

Frozen human postmortem brain specimens were obtained from Harvard Brain Tissue Resource Center and used in accordance with the policies of Brigham and Women's Hospital institutional review board.

Cell Cultures and Transfections.

Primary cortical neurons were prepared from E18 Sprague Dawley rat embryos of either sex, and cultured in Neurobasal medium (Invitrogen) supplemented with 1×B27 (Invitrogen) as described previously (Krichevsky and Kosik, 2001).

Transfections of young neurons at day 2 in vitro (DIV2) with Rb1 siRNA (RB1RSS351663 or RB1RSS351662; Invitrogen), siRNA-E2F1 (sc-61861; Santa Cruz Biotechnology), pre-miR negative control 2 (AM17111; Ambion), pre-miR-26b (AM17100; Ambion) (50 nm), anti-miR-26b, or anti-miR-scramble (Dharmacon; 10 nm) were performed with Lipofectamine 2000 (Invitrogen) according to the manufacturer's instructions. Transfections of mature (14-21 DIV) neurons were performed using NeuroMag (Oz Biosciences) according to manufacturer's instructions. The efficiency of transfections was ~90-95% for both young and mature neurons as we previously demonstrated (Wong et al., 2013).

RNA Isolation and Analysis.

Total RNA was extracted from frozen biopsy samples or cells using TRIZOL (Invitrogen) according to the manufacturer's instructions. Equal portions of white and gray matter from the temporal lobe were dissected and homogenized.

For miRNA analysis, TaqMan microRNA Reverse Transcription reagents and Universal PCR Master Mix with microRNA real-time PCR primers (Applied Biosystems) were used for qRT-PCR. For mRNA expression analysis, 1 μg of total RNA was reverse-transcribed with TaqMan Reverse Transcription Reagents (Applied Biosystems N808-0234) and gene expression quantified using SYBR green (Applied Biosystems SYBR Green PCR master mix). The sequences of primers used for qRT-PCR analyses are available upon request.

Western Blot.

Western blot analysis was performed according to standard protocol as described previously (Gabriely et al., 2008). The following primary antibodies have been used in this study: against cleaved caspase 3 (9661S), Histone H3 (9175), Hsp90 (4874), p15 (4822), p27 (2552), pRb (S780) (9307), pRb (S807/811) (9308), Tau (S404) (44758G) Tau (S396) (44752G), and γH2A.X (9718) were obtained from Cell Signaling Technology. Antibodies against β-actin (ab8229), bromodeoxyuridine (BrdU) (ab6326), Ki67 (ab16667), and PCNA (ab29) were from Abcam. Antibodies against CCNA2 (sc-239), CCNE1 (sc-754), CDK5 (sc-6247 and sc-173), p35/25 (sc-820), pRb (sc-50), and E2F1 (sc-193) were from Santa Cruz Biotechnology. Antibody against Tau (5202)/(T205) (44738G) was from Invitrogen, and Tuj1 (MMS-435P) was from Covance.

Human Cortical Neuron Culture.

Human fatal cortical tissues (gestational age 16 weeks), provided by Advanced Bioscience Resources were washed with DMEM. Meninges were removed and tissues cut into size of mouse/rat cortices (~3 mm$^3$) with forceps. Tissue was trypsinized in 0.25% trypsin and incubated at 37° C. for 20 min with occasional swirling. Trypsin was removed and the tissue washed twice with 10 ml of PR medium (DMEM with 10% fetal bovine serum, 2 mml-glutamine, 1 mm sodium pyruvate, and antibiotics). Tissue was triturated 5× with a 10 ml plastic disposable pipette. Cell suspension was filtered through a 70 μm followed by a 40 μm cell strainer. Cells were spun at 1600 rpm for 5 min. Supernatant was removed and 1 ml of PR medium was added to resuspend the cell pellet. PR medium was added and cells counted. Cells were plated in PR medium. Medium was replaced the next day (1 DIV) with PR and with Neurobasal at 5 DIV.

Validation of miR-26b Target.

miR-26b targets were validated using psiCHECK2 constructs (Promega C8021). Nucleotides 494-1156 of human Rb1 3' UTR were cloned into psiCHECK2 using XhoI and NotI. Mutations were introduced into the wild-type constructs using QuikChange Multi Site-Directed Mutagenesis Kit (Stratagene 200514). For assessing miR-26b activity, psiCHECK2 luciferase reporter vector containing a single perfect miR-26b binding site downstream of luciferase open reading frame has been used. Luciferase luminescence was revealed with Dual-Glo Luciferase Assay System (Promega E2920) and detected with Infinite F200 plate reader (Tecan).

Terminal Deoxynucleotidyl Transferase-Mediated Biotinylated UTP Nick End Labeling Assay.

In Situ Cell Death Detection Kit, TMR red (Roche 12 156 792 910) was used to reveal apoptotic cells. Cells were fixed in 4% paraformaldehyde (PFA) for 10 min at room temperature (RT) and permeabilized with 0.1% Triton X-100 in 0.1% sodium citrate for 2' on ice. Cells were then incubated with terminal deoxynucleotidyl transferase-mediated biotinylated UTP nick end labeling (TUNEL) reaction mixture for 1 h at 37° C., immunostained with anti-Tuj1 (MMS-435P; Covance) and analyzed by fluorescence microscopy.

Cell Viability Assay.

Luciferase/ATP-based assay (CellTiter-Glo Luminescent Cell Viability Assay; Promega G7571) was used according to the manufacturer's instructions. Cells were incubated with CellTiter-Glo reagent for 10 min at RT and luciferase signals were measured with the Infinite F200 (Tecan) plate reader. To measure cell viability of hydrogen peroxide-treated primary neurons, WST-1 assay (Roche 11644807001) was used according to manufacturer's instructions. Briefly, cells were incubated with WST-1 reagent at 1:10 dilution at 37° C. for 1 h, and absorbance was then measured at 440 nm with the Infinite F200 (Tecan) plate reader.

Immunocytochemistry.

Cells were fixed in 4% PFA in PBS at RT for 10 min, permeabilized with 0.25% Triton X-100 for 5 min, and washed (2×) with PBS. Cells were then blocked with 1% normal goat serum (NGS)-PBS for and incubated for 1 h at RT with primary antibody in 0.1% NGS-PBS. Cells were washed (3×) with PBS and incubated with fluorescence-conjugated secondary antibodies at RT for 45 min. Cells were washed (3×) with PBS and mounted in Vectashield (Vector Laboratories) supplemented with DAPI and analyzed by fluorescent microscopy.

Cytoplasmic and Nuclear Fractionation.

The procedure was performed according to (Bernocco et al., 2008). Cells were harvested in Buffer D (10 mm PIPES, pH 6.8, 100 mm NaCl, 300 mm sucrose, 3 mm MgCl$_2$, 5 mm EDTA, and 0.015% digitonin) with protease inhibitors (Complete Mini) and shaken for 15 min at 4° C. After centrifugation at 5000×g for 10 min at 4° C., the supernatant was collected and represented the cytosolic soluble protein fraction. The pellets were resuspended with Buffer T (10 mm PIPES, pH 7.4, 100 mm NaCl, 300 mm sucrose, 3 mm MgCl$_2$, 3 mm EDTA, and 0.5% Triton X-100) with protease inhibitors and shaken for 30 min at 4° C. After centrifugation at 5000×g for 10 min at 4° C., the pellet contained the nuclei that were washed twice with Buffer T and then lysed in Buffer C (10 mm PIPES, pH 7.4, 10 mm NaCl, 1 mm $MgCl_2$, 1% Tween 40, 0.5% DOC, and 1 U/µl benzonase) with protease inhibitors and shaken for 30 min at 4° C. Centrifugation at 6800×g at 4° C. for 30 min allowed the recovery of the supernatant as the nuclear fraction.

Immunoprecipitation.

Cells were harvested 7 d after transfection in NP-40 lysis buffer (50 mm Tris-HCl, pH 7.4, 150 mm NaCl, 1 mm EDTA, 0.1% NP-40) with protease inhibitors, and cell lysates prepared as described above. Cell lysates (800 µg) were incubated with 1 µg immunoprecipitating antibody for 1 h at 4° C. and then incubated overnight at 4° C. with 20 µl anti-rabbit-IgG beads (eBioscience). Immunoprecipitated complexes were washed (4×) with lysis buffer (centrifugation at 1000×g at 4° C. for 5 min), recovered in 40 µl 2× Laemmle buffer with 50 mm fresh dithiothreitol and boiled for 5 min; samples were loaded onto SDS-PAGE gels and analyzed by immunoblotting.

In Vitro Kinase Assays.

Immunoprecipitated complexes were washed (2×) in NP-40 lysis buffer and in HEPES buffer (40 mm HEPES, pH 7.2, 8 mm $MgCl_2$) and then used to phosphorylate 1 µg Histone H1 (Millipore 14-155), Rb1 (769) (Santa Cruz Biotechnology sc-4112), or Tau 441 (151-421; SignalChem) peptides in 30 µl kinase buffer (40 mm HEPES, pH 7, 8 mm $MgCl_2$, 125 nm okadaic acid, protease inhibitors, and 10 mm ATP). After incubation for 1 h at 37° C., the reactions were stopped by adding 2× Laemmle buffer and boiling for 5 min, and the analysis was performed by Western blotting for phospho-Rb (780) (9307; Cell Signaling Technology), phospho-Histone H1 (T146) (ab3596; Abcam), and phospho-Tau (S404) (44758G; Cell Signaling Technology).

Results miR-26b is Up-Regulated in Human MCI and AD

Figure 1C:
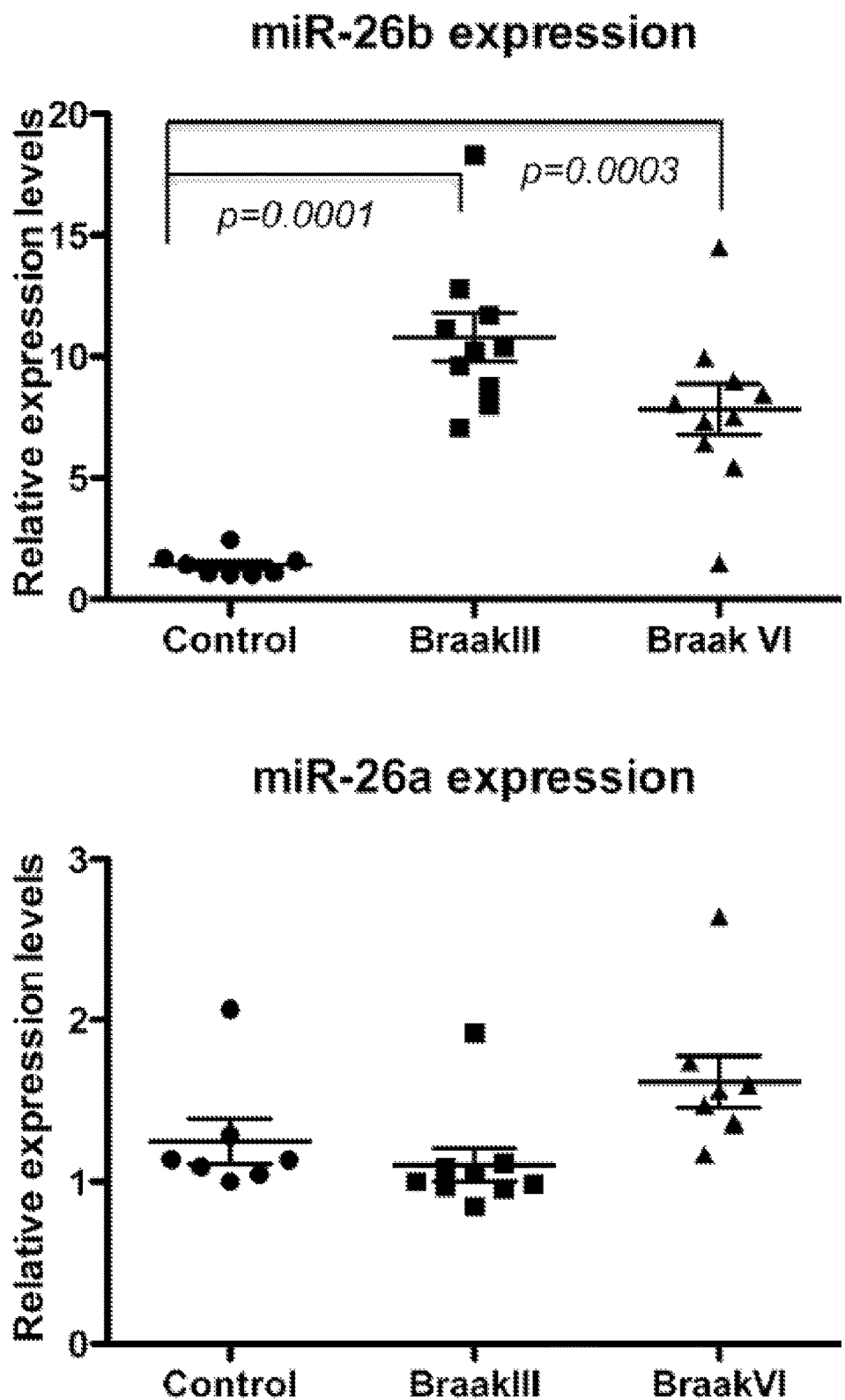

Using multiplex real-time qRT-PCR, we profiled miRNA expression in defined pathological areas of human MCI and AD brains along with similar regions of aged-matched healthy brains. RNA was isolated from frozen temporal cortex, a region susceptible to AD, of individuals with MCI (Braak III), severe AD (Braak VI), and non-pathological brains (n=8-10 per group) (FIG. 1A). Expression analysis was performed for a set of 21 selected miRNAs, highly abundant in brain regions susceptible to AD. This analysis suggested several miRNAs as significantly dysregulated in Braak III cases compared with the control group (FIG. 1B). The analysis of Braak III tissues was not skewed by the differential representation of neurons vs. glia since there is no yet significant neural loss at Braak III stage of the disease. More specific singleplex qRT-PCR miRNA expression analyses confirmed the most significant increase in the expression of miR-26b (but not of its paralog miR-26a) in both Braak stages III and VI (FIG. 1C). A previous report by Cogswell et al. suggested up-regulation of both miR-26a and miR-26b in hippocampi of Braak III/IV patients (Cogswell et al. 2008). The data we present here, using more specific singleplex qRT-PCR, has validated that only one member of the miR-26 family, miR-26b is elevated significantly in MCI and AD. This is in contrast to the other reported screens of miRNA dysregulation in AD, which have not detected up-regulation of miR-26b (Wang et al. 2011, Satoh 2012). This discrepancy is likely due to the less specific character of the platforms used in other studies and to cross-hybridization between the probes for miR-26a (not altered) and miR-26b. Since other dysregulated miRNAs identified in our screen (e.g. let-7i and miR-29c) belong to larger miRNA families that include multiple members, and thus assessing their specific functions will be more challenging, and our pilot experiments suggested most interesting and consistent phenotype for miR-26b, we focused in this study on miR-26b functions and its potential role in the AD neuropathology.

miR-26b Overexpression Induces Cell Cycle in Post-Mitotic Neurons

Several studies reported that miR-26 regulated cell cycle in dividing cells (Huse et al. 2009, Kota et al. 2009, Kim et al. 2010, Lu et al. 2011, Dill et al. 2012). Since reactivation of cell division and failure in cell cycle regulatory mechanisms are some of the earliest neuronal abnormalities in the AD brains, we hypothesized that this might be due to the increased miR-26b expression. To study the effects of miR-26b up-regulation on neuronal cells, we used a gain-of-function approach and transfected E18 postmitotic cortical cultures with synthetic miR-26b mimic molecules (pre-miR-26b). When transfected at 50 nM, pre-miR-26b led to increased miR-26b levels and elevated its endogenous activity in neurons 3-4-fold, as indicated by the activity of miR-26b luciferase reporter (FIG. 5B).

Figure 2A:
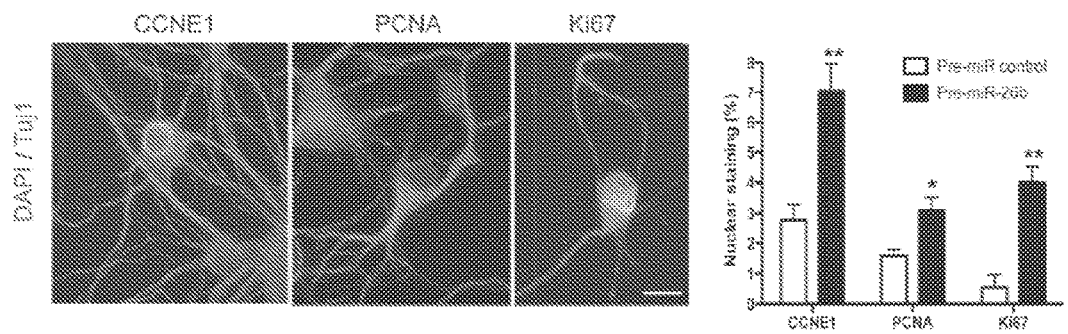
FIGS. 2A-C. MiR-26b overexpression induces cell cycle in primary post-mitotic neurons. (A) miR-26b overexpression in cortical neurons induces expression of CCNE1, PCNA and Ki67 compared to neurons transfected with pre-miR control. Typical immunostainings are demonstrated. Histograms depict the number of Tuj1-positive neurons co-stained with the indicated nuclear markers five days post-transfection. (Student's t-test, two-tailed *p<0.05 and p<0.001, scale bar-10 µm, n=300 neurons/condition). (B) Representative western blot analysis and quantification of four independent experiments demonstrate effects of miR-26b overexpression on positive (CCNE1 and ppRb1-Ser780), and negative (p27 and p15) regulators of cell cycle (Student's t-test, two-tailed p<0.001 and, *p<0.0001, five days post-transfection). (C) Analysis of BrdU incorporation in neurons by immunostaining for Tuj1 and BrdU demonstrates that overexpression of miR-26b induces DNA replication in post-mitotic cortical neurons. Representative immunostainings are shown. Histograms depict the percentage of BrdU positive neurons (Student's t-test, two-tailed p<0.001, n=300, scale bar 50 µm).
Figure 2B:
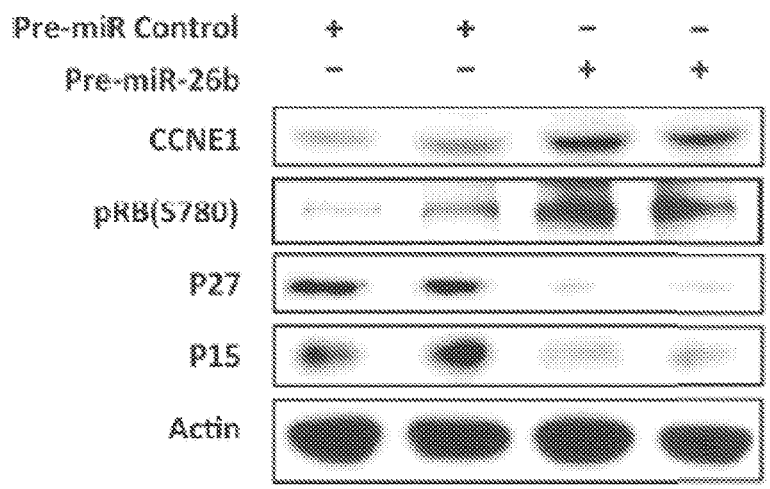
Figure 2B:
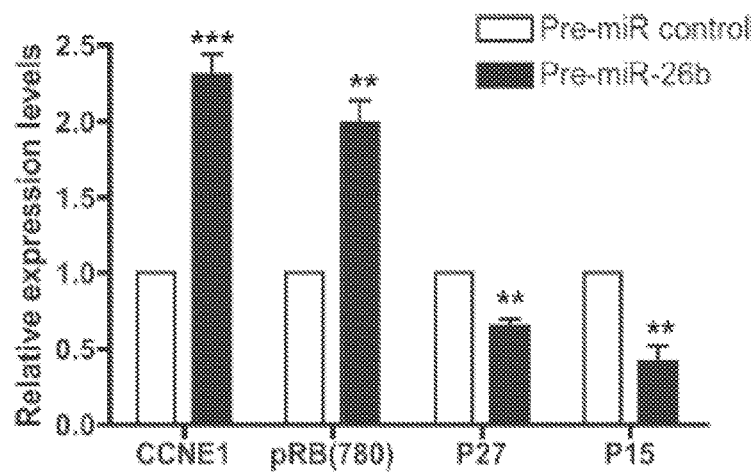
Figure 2C:
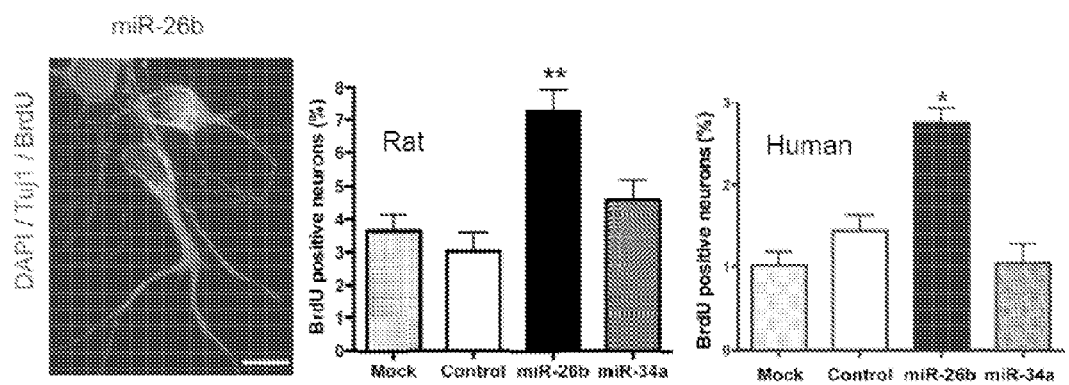

To test the effects of miR-26b on neurons, the cells transfected with pre-miR-26b or a scrambled pre-miR-control, were harvested 5 days after transfection and subjected to immunostaining for various cell cycle and proliferation markers. MiR-26b overexpression significantly increased the nuclear staining of cyclin E1 (CCNE1), PCNA (DNA polymerase processivity factor), and Ki67 in post-mitotic (Tuji+) neurons (FIG. 2A). Ki67, a marker of proliferative cells was nearly undetectable in neurons treated with the control oligo, and detected in 4% Tuj1$^+$ neurons in the miR-26b transfected cultures. The characteristic pattern of Ki67 staining suggested that neurons were in G1 and S phases but never proceeded to G2/M. These results indicate that elevated expression of miR-26b, also observed in MCI and AD cases, can induce CCE in post-mitotic neurons. To confirm this, we transfected primary rat cortical neurons with pre-miR-26b or a scrambled pre-miR control and performed western blot analysis for several regulators of cell cycle such as CCNE1 and phosphorylated pRb (ppRB), often observed in AD neurons (Jordan-Sciutto et al. 2002, de las Cuevas et al. 2003). Overexpression of miR-26b led to a significant increase in the expression of CCNE1, and ppRb, and decrease in the cell cycle inhibitors p27 and p15 (FIG. 2B). To further confirm that miR-26b was inducing CCE in post-mitotic neurons we performed a BrdU incorporation assay. Our results demonstrate that overexpression of miR-26b significantly increases BrdU incorporation in both rodent and human Tuji$^+$ neurons (FIG. 2C). This effect was specific for miR-26b, as neither a control miRNA, nor miR-34a (another miRNA abundant in the brain, and involved in both neurodegeneration and regulation of cell cycle in proliferative cells-Bommer 2007, refs) had an effect on CCE in neurons. Glial GFAP$^+$ cells that typically constitute <5% of our rodent primary cultures and ~40-50% of human primary cultures were not affected by miR-26b overexpression (data not shown).

miR-26b Overexpression Induces Cdk5 Re-Shuttling and Tau Phosphorylation

Figure 3A:
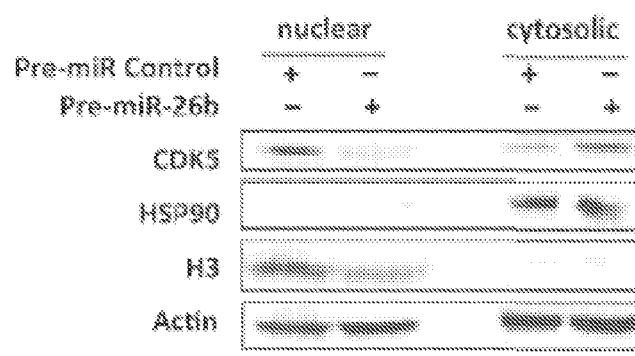
FIGS. 3A-B. MiR-26b overexpression leads to Cdk5 nuclear export and increased tau phosphorylation in primary neurons. (A) Western blot analysis shows Cdk5 re-shuttling from the nuclear to the cytosolic fraction in miR-26b-overexpressing cortical neurons. Histone H3 and Hsp90 were used as markers of nuclear and cytosolic fractions, respectively, and actin as a loading control. (B) Western blot analysis shows that miR-26b overexpression increases tau phosphorylation at 4 different epitopes as compared to pre-miR control transfected neurons. Quantification depicts the densitometric analysis of 2 experiments (Student's t-test, two-tailed *p<0.05).

Inhibition of cell cycle in post-mitotic neurons is exerted by a nuclear complex consisting of p27 and cyclin dependent kinase 5 (Cdk5). Cdk5 is an atypical kinase that, when localized to nucleus, plays a central role in this process (Zhang et al. 2008, Zhang and Herrup 2008). Cdk5 does not have an intrinsic nuclear localization signal and its nuclear localization relies on its binding to the cyclin-dependent kinase inhibitor p27. In the absence of p27, Cdk5 is exported to cytoplasm, where it can no longer suppress the cell cycle (Zhang et al. 2010). Cytosolic Cdk5 is also well characterized as a major tau kinase (Lee and Tsai 2003, Mazanetz and Fischer 2007). Since miR-26b transfections significantly reduced the levels of p27 in neurons, we tested how they affected Cdk5 intracellular localization. MiR-26b or pre-miR control were transfected into primary neurons followed by cytoplasmic/nuclear fractionation. Western blot analysis revealed that overexpression of miR-26b caused the export of Cdk5 from the nucleus to the cytoplasm (FIG. 3A).

Figure 3B:
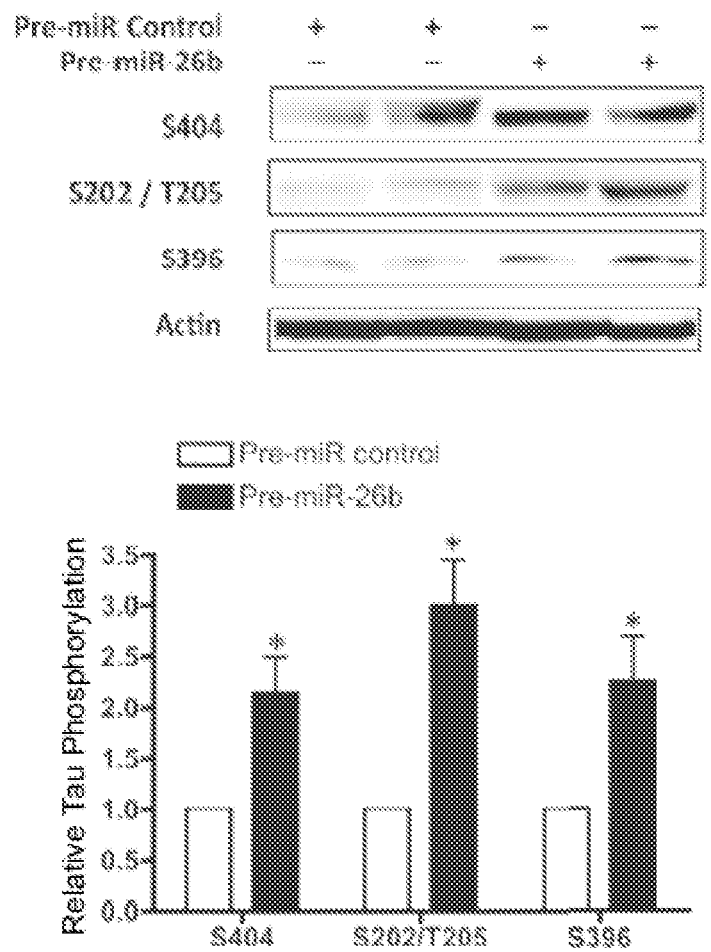
Figure 4A:
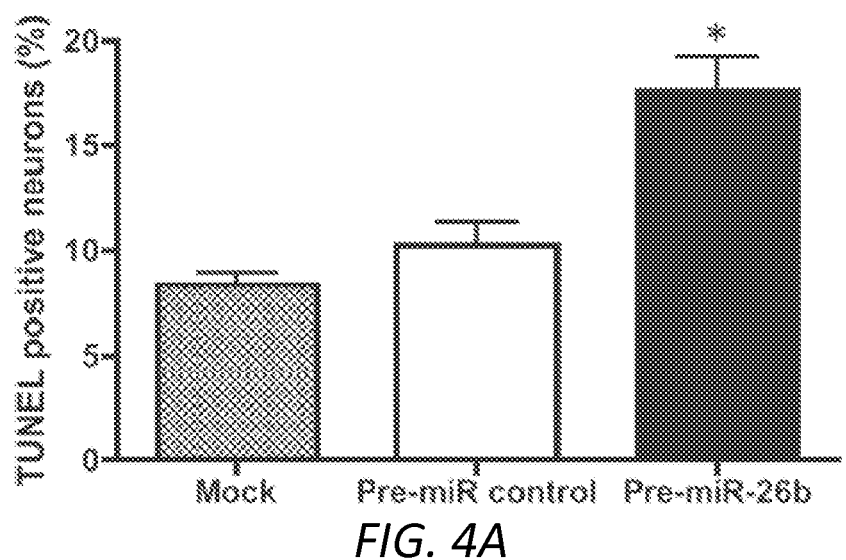
FIGS. 4A-E. Post-mitotic neurons overexpressing miR-26b show evidence of apoptosis and reduced cell viability. (A) Histograms depict the percentage of TUNEL positive neurons 5 days post-transfection (Student's t-test, two-tailed *p<0.05, n=3, 300 neurons/condition). (B) Western blot analysis and quantification showing that overexpression of pre-miR-26b leads to an increase in caspase 3 cleavage in post-mitotic neurons (Student's t-test, two-tailed *p<0.01, n=3). (C) Cell viability of neurons analyzed by ATP-based assay 5 days post-transfections of pre-miR-26b, pre-miR-30a or pre-miR control (Student's t-test, two-tailed p<0.001, n=3). (D) Representative images of neurons transfected with pre-miR-26b or pre-miR control and stained for Tuj1, seven days post-transfection (scale bar 50 µm). (E) miR-26b inhibition protects primary neurons against hydrogen peroxide-mediated cytotoxicity. Cell viability of neurons was measured using WST-1 reagent 5 d post-transfection of anti-miR-26b or anti-miR-scramble and 14-16 h post H2O2 treatment (Student's t test, two-tailed p<0.005, *p<0.05, n=4 with quadruplicate in each experiment).
Figure 4B:
Figure 4C:
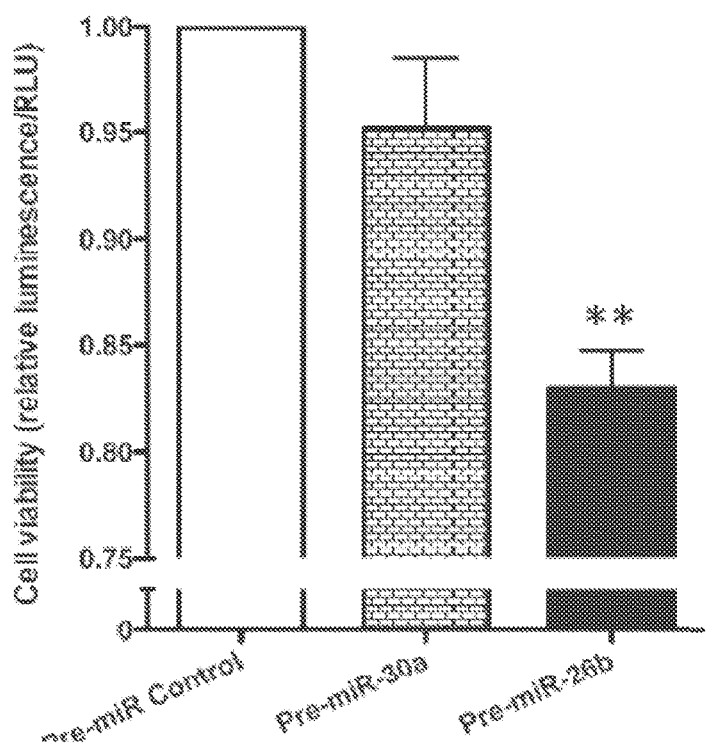
Figure 4D:
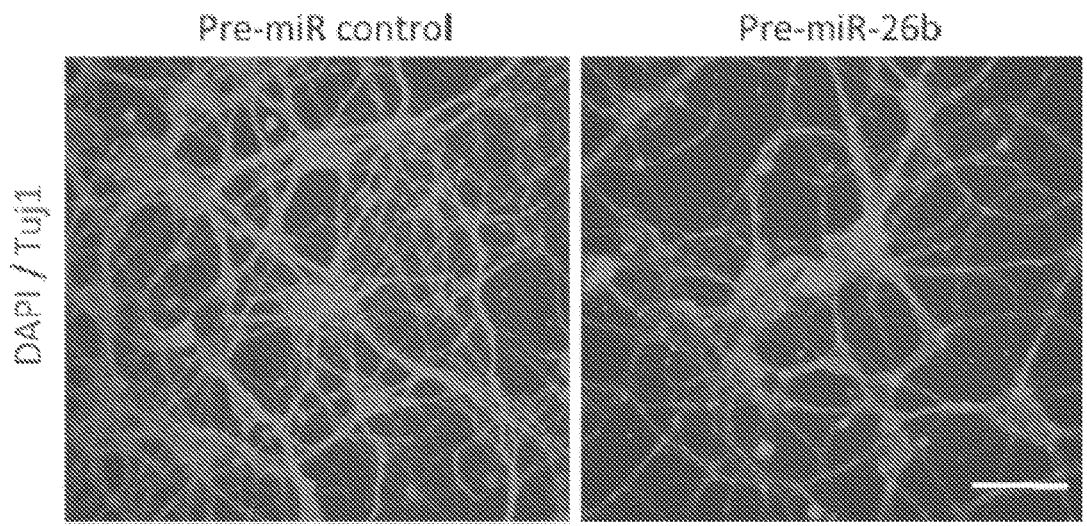
Figure 4E:
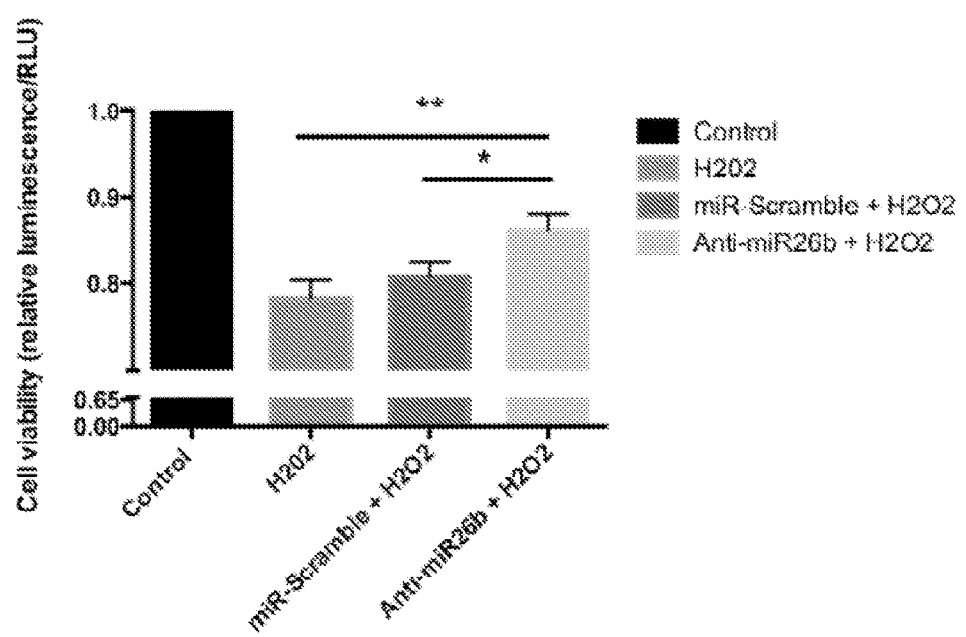

Interestingly, the vast majority of neurons with neurofibrillary tangles (NFT) in AD brains are also positive for cell cycle markers (Busser et al. 1998), suggesting a common regulation or a link between CCE and tau aggregation. Since miR-26b affects cellular localization of Cdk5, a major tau kinase, we tested how overexpression of miR-26b affects tau phosphorylation in post-mitotic neurons. Western blot analyses revealed a statistically significant increase in tau phosphorylation at several sites, including pS202/T205 (AT8) and pS396/S404 (PHF-1), Cdk5 phosphorylation sites typical for early and late neurofibrillary tangles, respectively, in AD (FIG. 3B).

miR-26b Overexpression Leads to Apoptotic Cell Death of Primary Neuronal Cultures Induction of cell cycle in neurons, and also Cdk5 re-shuttling often lead to (and may even cause) neuronal death (Byrnes et al. 2007, Fu et al. 2012). Importantly, the observed CCE and tau hyper-phosphorylation in miR-26b overexpressing neurons were followed by apoptotic cell death as indicated by immunostaining and TUNEL experiments (FIGS. 4A and D). This effect was sequence-specific as neurons transfected with pre-miR control and other miRNA mimics did not cause an increase in apoptosis above the background levels observed in mock-transfected cultures. Furthermore, the levels of activated (cleaved) caspase 3, the major effector of neuronal apoptosis associated with AD, were significantly increased in neurons transfected with pre-miR-26b (FIG. 4B). Overexpression of miR-26b led to a significant sequence-dependent decrease in neuronal cell viability, as assessed by an ATP based metabolic activity assay (FIG. 4C). Finally, we investigated if miR-26b knockdown could have a neuroprotective effect following an AD-relevant apoptotic stimulus. We used hydrogen peroxide treatment, an established experimental system for studying oxidative stress-induced neurodegenerative response, which also activates CCE in postmitotic neurons (Schwartz et al., 2007). Primary cortical neurons were transfected with sequence-specific miR-26b inhibitor (anti-miR-26b) or an anti-miR-scramble control molecule, and then exposed to 15 µM H2O2 overnight. As shown in FIG. 4E, miR-26b inhibition led to a significant increase in cell viability of hydrogen peroxide-treated primary neurons. Since the miR-26b's paralog miR-26a could potentially compensate for the reduced miR-26b activity, more potent inhibition of both miR-26a and -26b might be used to further enhance the neuroprotection.

miR-26b Directly Regulates Expression of Retinoblastoma Protein in Neurons and Affects Rb1/E2F Transcriptional Targets To identify principal targets that mediate miR-26b effects in neurons, we utilized several target prediction algorithms, and found two putative highly conserved binding sites within the Retinoblastoma (Rb) 3' UTR (FIG. 5B). Retinoblastoma is a potent tumour suppressor that controls cell cycle at the G1-to-S phase checkpoint, primarily by inhibiting E2F transcription factors and thereby hampering the transcription of genes required for transition to S phase (Sellers et al. 1995, Smith et al. 2000). In neuronal cells, Rb protein likely plays a crucial role in cell survival and its phosphorylation is tightly correlated with neuronal death (Galderisi et al. 2003, Greene et al. 2004, Andrusiak et al. 2012). In addition, Rb/E2f signalling has been implicated in the regulation of gene expression in AD (Ranganathan et al. 2001, Munoz et al. 2005). Western blot analysis demonstrated that miR-26b overexpression in primary neurons led to substantial reduction of Rb levels (FIG. 5A).

To confirm that Rb mRNA was a direct target of miR-26b, we constructed luciferase reporter plasmids that contained either the wildtype 3'UTR sequence of Rb mRNA or one in which the miRNA-binding sites have been mutated (FIG. 5B). Using these reporters, we validated that miR-26b directly binds to the 3'UTR of Rb mRNA and represses its expression in primary neurons (FIG. 5B). This repression was abolished by mutations in one of two predicted miR-26b binding sites within Rb 3'UTR. These results indicate that miR-26b directly regulates expression of Rb.

E2F family of transcription factors is a key downstream effector of the Rb activity; reduced levels of Rb lead to the de-repression of E2F-driven transcription and thus up-regulation of E2F transcriptional targets, including both cell cycle and pro-apoptotic genes. To investigate if overexpression of miR-26b regulates E2F targets, we transfected either pre-miR-26b or a pre-miR control into primary neurons and performed qRT-PCR analysis of known E2F transcriptional target genes, such as cell cycle regulators CCNE1, CCNE2, and PCNA and the regulators of apoptosis APAF1, MAP3K5, Caspase 8, and Caspase 3. Remarkably, overexpression of miR-26b in neurons led to a significant up-regulation of the majority of investigated E2F targets, including both S-phase and pro-apoptotic genes (FIG. 5C). Of note, Bim, an important mediator of apoptosis, transcriptionally regulated by several factors including E2F1, was not affected by miR-26b overexpression.

To further confirm that miR-26b regulation is mediated through the E2F1 transcription machinery, we simultaneously overexpressed miR-26b and downregulated E2F1 by the cognate siRNA. We observed that E2F1 silencing abolished miR-26b-induced elevation of CCNE1, downregulation of p27, and most importantly it rescued neurons from apoptosis, as suggested by the levels of cleaved caspase 3 (FIG. 5D).

Since there are many important E2F1 targets regulated by miR-26b, it may not be practical to attribute observed cell death to a specific gene(s) involved in apoptosis versus cell cycle pathway. Nevertheless, we argue that miR-26b-induced CCE is unlikely to be merely a coincident event for the following reasons: (1) it is established by numerous publications that induction of CCE in postmitotic neurons is tightly linked and can lead to cell death in various systems, even in the absence of transcriptional induction of apoptotic genes (Park et al., 2007; Andrusiak et al., 2012); (2) in our system, induction of proliferative markers Ki67 and PCNA was an early event observed 3 d post miR-26b transfection; and (3) one of the most pronounced effects of miR-26b overexpression was strong downregulation of the cell cycle inhibitor p27kip1, the event sufficient to induce death of cortical neurons in vitro and in vivo (Akashiba et al., 2006; Ye and Blain, 2010).

Down-Regulation of Rb Mimics the Effects of miR-26b on Cell Cycle and Apoptosis in Neurons To assess whether Rb is the major miR-26b target that mediates miR-26b phenotype observed in primary neurons, we investigated if down-regulation of Rb by RNAi mimics the effects of miR-26b overexpression on cell cycle and apoptosis in neurons. Importantly, the siRNAs deployed in this study reduced target Rb mRNA levels by a magnitude comparable to that previously observed to be elicited by ectopic miR-26b expression in these same cells (~2-fold at 48-72 hr post-transfection, FIG. 6A, left panel); thus, RNAi approach allowed to reasonably approximate the consequences of miR-26b's action on this effector molecule. Cortical neurons were transfected with either different siRNAs cognate to Rb mRNA or a control siRNA. Five days after transfection the cells were subjected to immunostaining for the cell cycle markers PCNA and Ki67. As expected, down-regulation of Rb by siRNAs increased the nuclear staining of both PCNA and Ki67, indicating CCE similar to that observed in miR-26b overexpressing cells (FIG. 6A). In parallel, Western blot analyses of cells transfected with Rb siRNA revealed an increase in CCNE1 and phosphorylated Rb, and a decrease in p27 (FIG. 6B, 120 hr post-transfection), similar to those observed in miR-26b overexpression conditions. Of note, since direct down-regulation of Rb expression by either cognate siRNA or miR-26b overexpression (observed at protein level 72 hours post-transfection) leads to the increased phosphorylation of the remaining Rb protein at a later time point (120 hr), this suggests that increased phosphorylation of Rb in the miR-26b-overexpressing cells (FIG. 2B) is a secondary effect, caused by miR-26b targeting and repression of Rb.

Figure 6C:
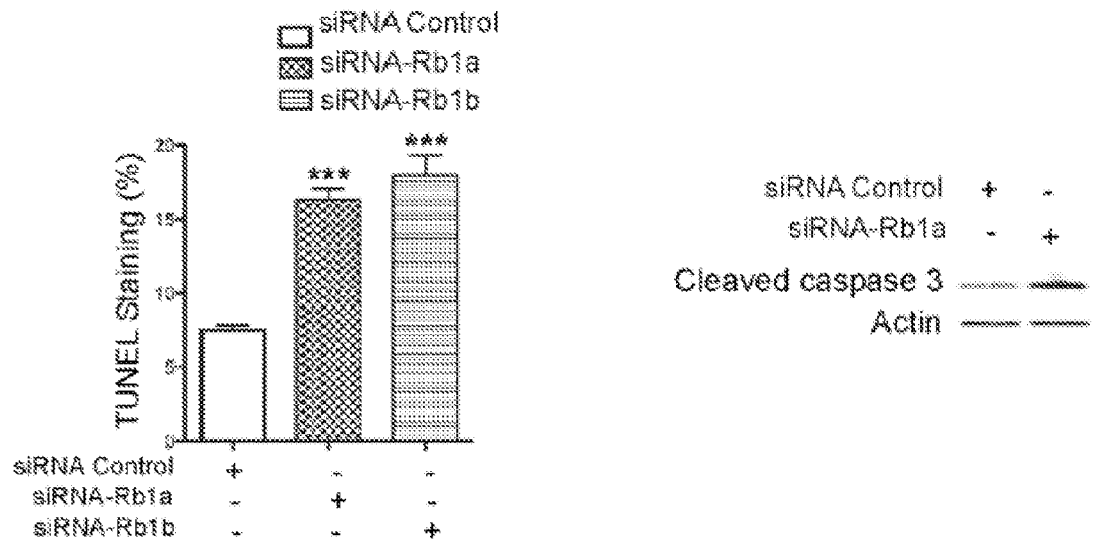
Figure 6D:
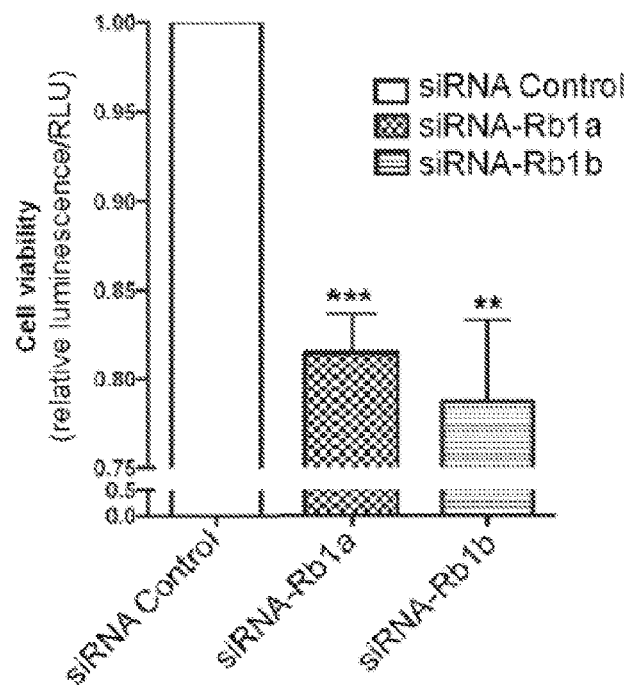
Figure 6E:
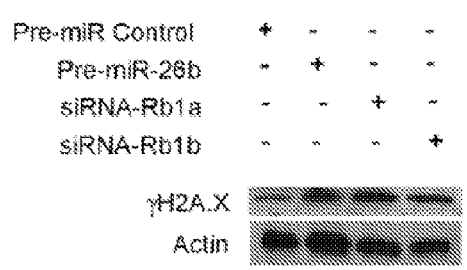
Figure 6E:
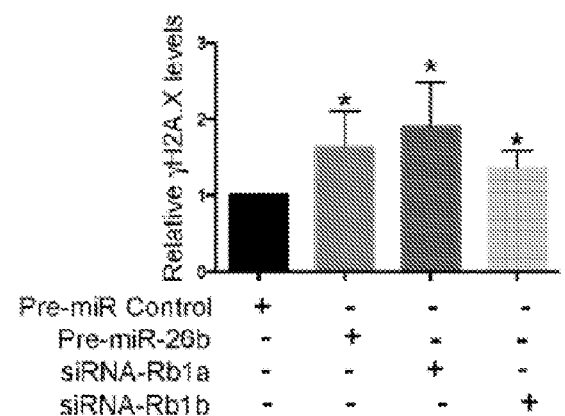

Furthermore, down-regulation of Rb by siRNAs caused an increase in cleaved caspase 3 and led to a significant increase in the number of TUNEL positive apoptotic neurons (FIG. 6C). Finally, analysis of cell viability by a luciferase/ATP based assay 7 days after transfection with siRNA-Rb, or a control RNA duplexes demonstrated that, similarly to overexpression of miR-26b, knockdown of Rb leads to a significant decrease in neuronal cell viability (FIG. 6D).

Figure 7A:
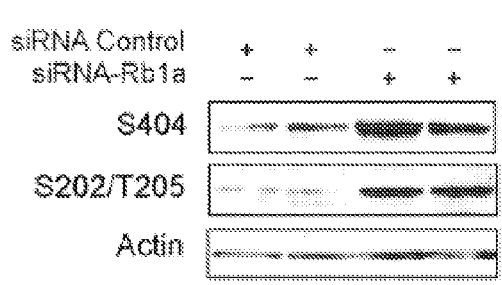
FIGS. 7A-C: Retinoblastoma down-regulation by miR-26b or cognate siRNA leads to an increase in tau phosphorylation and Cdk5 activity in post-mitotic neurons. (A)
Figure 7A:
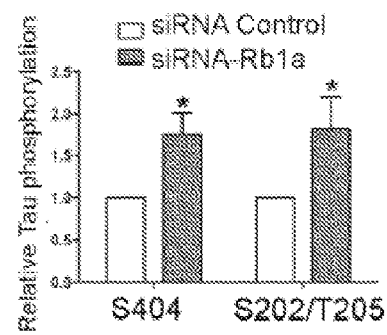
Figure 7B:
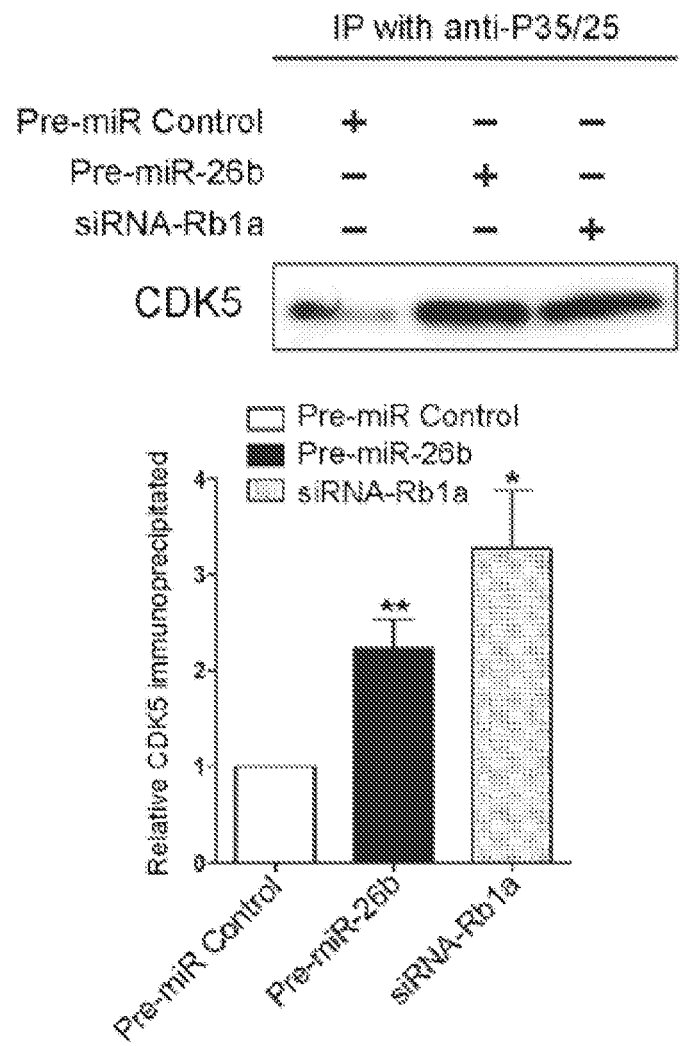

Reports have shown that cell cycle induced by Rb1 deficiency leaves cells more susceptible to DNA damage (Manning and Dyson, 2011). To evaluate miR-26b-overexpressing or Rb1-deficient neurons for the presence of DNA damage, we assessed them for γH2AX, a histone H2AX phosphorylation at serine 139 and marker for DNA damage induced by double-strand breaks (Rogakou et al., 1998). Transfections with pre-miR-26b, as well as siRNAs-Rb1, all led to an increase in the levels of γH2AX (FIG. 6E), suggesting that Rb1 inhibition and the downstream CCE may activate the DNA damage pathway.

miR-26b Overexpression and Rb Repression Lead to Tau Phosphorylation and an Increase in Cdk5 Activity We next sought to determine if, like miR-26b overexpression, down-regulation of Rb by RNAi could also lead to an increase in tau phosphorylation. Primary cortical neurons were transfected with siRNA-Rb or control RNA duplex and subjected to western blot analysis 5 days post-transfection. SiRNA-mediated knockdown of Rb led to a statistically significant increase in tau phosphorylation at S202/T205 (AT8) and S404 (PHF-1), Cdk5 phosphorylation sites typical for early and late neurofibrillary tangles, respectively, in AD (FIG. 7A).

It has been demonstrated that nuclear Cdk5 blocks cell cycle re-entry in activity-independent way (Zhang and Herrup 2008, Zhang et al. 2010). Our data suggest a role for Cdk5 re-localization in the miR-26b-induced CCE. For miR-26b/siRNA-Rb-induced tau-hyperphosphorylation, however, Cdk5 kinase activity might be required. To investigate whether miR-26b overexpression and Rb down-regulation activate Cdk5 kinase, we transfected primary cortical neurons with miR-26b or siRNA-Rb and immunoprecipitated the active Cdk5 complex using antibodies to its activator subunit p35/p25. Western blot analysis for the immunoprecipitated complexes revealed a significant increase in active, p35/p25-bound Cdk5 after either miR-26b overexpression or down-regulation of Rb by RNAi (FIG. 7B).

Figure 7C:
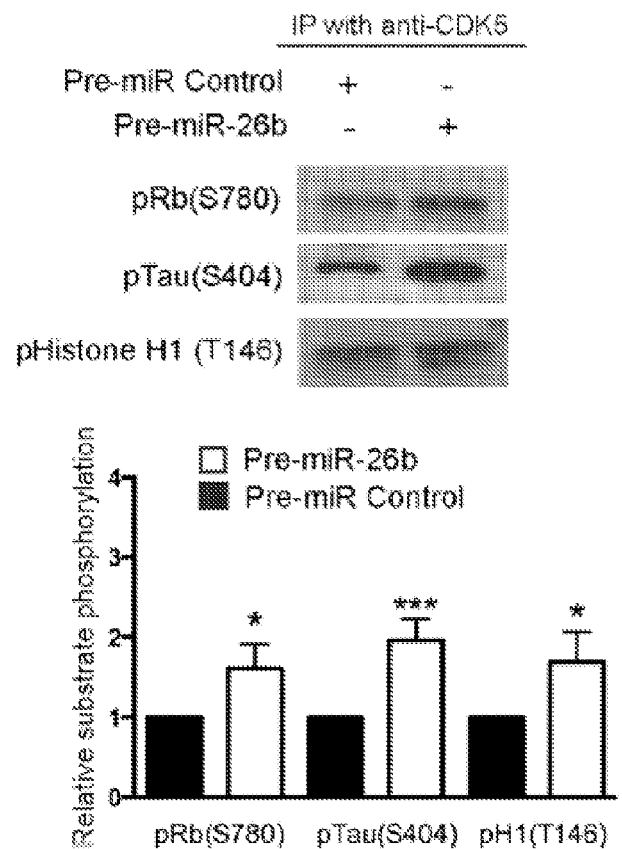

To directly assess miR-26b effect on the Cdk5 activity we performed in vitro kinase assays on primary cortical neurons. Five days after transfection with either pre-miR-26b or pre-miR control, the neurons were lysed, immunoprecipitated for active Cdk5, and enzymatic activity assays were performed using validated substrate peptides. Of relevance, Rb1 is a validated substrate of Cdk5 in neuronal cells (Hamdane et al., 2005; Futatsugi et al., 2012); we therefore assessed Cdk5 kinase activity on Rb1, Tau, and also its classical substrate Histone H1. These analyses demonstrated that miR-26b overexpression increases Cdk5 activity in the phosphorylation of all three tested substrates (FIG. 7C). Therefore, miR-26b overexpression leads to aberrant CCE and, in parallel, increases tau phosphorylation in neurons, through reduction of Rb and Cdk5 nuclear export and activation, which appear to be central in the induction of these phenotypes.

Mature Neurons Exhibit the Same Effects after Treatment with miR-26b and siRNA-Rb Since for technical reasons most of our experiments have been performed on primary neurons transfected at DIV 2, we finally investigated whether miR-26b overexpression has similar effects on mature synaptically active neurons, as they would represent a better cellular model of neurons in AD. To this end, we cultured primary cortical neurons for two weeks prior to transfecting them via magnetofection with either pre-miR-26b or pre-miR control and analyzing 3-5 days post-transfection. Similar to young neurons, miR-26b overexpression down-regulated Rb expression and subsequently led to a significant increase in the levels of CCNE1, phosphorylated Rb, and phosphorylated tau, and to a decrease in p27 levels (FIG. 8A). Furthermore, miR-26b overexpression induced apoptosis in these cells, as indicated by increase in cleaved caspase 3 levels 120 hours after transfection (FIG. 8B). Finally, direct knockdown of Rb in mature neurons via siRNA-Rb mimicked principal effects of miR-26b overexpression. Specifically, it increased the relative expression of CCNE1, phosphorylated Rb and phosphorylated tau, and decreased the levels of p27 (FIG. 8C). Similar to miR-26b overexpression, it also led to caspase 3 cleavage in mature neurons (FIG. 8C).

Example 2

MiR-26b is Neuroprotective in Primary Cortical and Hippocampal Neurons

A number of neuronal miRNAs might play critical roles in the pathogenesis of human neurologic disorders. As described above, miR-26b, a miRNA that is significantly dysregulated in MCI and AD, controls key signaling pathways in neurons and thereby modulates neuron viability in a sequence-specific manner. As described in this Example, a high-throughput screen as outlined below also identified this miRNA as a top hit modulator of neuroprotection for primary cortical and hippocampal neurons.

A high-content screen was performed on mouse primary cortical, and further validated on hippocampal neurons, to unbiasedly identify miRNA modulators of neuronal viability and sensitivity to pathogenic stress. MiRNAs are largely conserved between rodents and humans. Out of the >600 miRNAs expressed in neocortex, 90 most abundant account for >95% of neuronal miRNA repertoire in both mouse and human cells, based on the analysis of multiple studies, and therefore account for the majority of miRNA regulation in neurons. To focus our screen on key physiological regulators, we preselected 70 conserved miRNAs that are most abundant in mammalian neurons. Among them only a few have been implicated in neuronal functions and viability thus far. This design enabled the high-content screen in a convenient 96-well format. Since our goal was the identification of endogenous miRNA modulators of neuronal viability, the screen utilized sequence-specific miRNA inhibitors (antagomiRs) that are chemically modified antisense oligonucleotides (ASOs). A commercial library of validated locked-nucleic-acid (LNA) inhibitors was utilized; such molecules applied at 100 nM provided potent inhibition of even most highly expressed miRNAs, with no nonspecific toxicity observed.

Glutamate Toxicity Paradigm.

Glutamate, the major excitatory neurotransmitter in the CNS, plays important physiological roles in neural functions and plasticity; it is, however, also one of the major neurotoxins. Excitotoxicity, the neuronal damage caused by excessive stimulation of excitatory receptors and overload of intracellular calcium, considered as a fundamental mechanism underlying several chronic disorders, including AD, Parkinson's disease, Huntington's disease, ALS, and FTD as well. In AD, for example, impaired expression of neuronal ionotropic Glu receptors, removal of glutamate from synaptic cleft by glia, and ultimately disrupted glutamate uptake are thought to cause exitotoxicity and lead to progressive degeneration of cortical and hippocampal brain regions. Neurons carrying a common ALS/FTD mutation are more susceptible to glutamate excitotoxicity than normal neurons. Therefore, the neurotoxicity observed in cultured cortical neurons under chronic glutamate exposure is an excellent model relevant to a broad range of neurodegenerative processes, and we utilized it in our high-throughput screen of antagomiRs.

Neurons were transfected with individual antagomiRs at DIV7 in triplicates as described above and treated with 100 µM glutamate 48 hours post-transfection. Cell viability and metabolic integrity were assessed 24 hours post-treatment using WST-1 colorimetric assay. This protocol provided 1) nearly 100% efficiency of lipophilic transfection of primary neurons, 2) negligible unspecific toxicity, 3) sufficient timing to induce miRNA-mediated signaling prior to the glutamate treatment, and 4) reliable and highly accurate detection of both positive and negative effects of antagomiRs on neuronal viability (or in other words, both neuroprotective and neurotoxic antagomiRs). At 100 µM, glutamate reduced the viability of cortical and hippocampal neurons in 30%, and this effect was modulated by several individual antagomiRs. In parallel, a similar screen of antagomiR-transfected but untreated (unstressed) sister cultures has been performed, and utilized for normalization of the glutamate dataset.

An independent screen was performed on mature neurons (at DIV19) using a toxic Aβ oligomers species, implicated in the pathogenesis of Alzheimer's disease.

These screens resulted in the identification of several miRNAs that either exacerbated or ameliorated glutamate and/or Aβ toxicity. Since ASOs may have unspecific off-target effects, the most significant hits were further validated 1) in rodent (both mouse and rat) neurons, using miRNA inhibitors of different 2'-O-MOE chemistry (see FIG. 9), 2) with miRNA mimics (gain-of-function which should cause opposite phenotypes), 3) in human primary cortical neurons. The most consistent neuroprotective effects were observed in neurons treated with anti-miR-26b. Conversely, overexpression of miR-26 led to enhanced neuronal apoptosis, as previously reported. As noted above, inhibition of miR-26 also proved neuroprotective against peroxide-induced oxidative stress.

REFERENCES

Ackerley, S., A. J. Grierson, J. Brownlees, P. Thornhill, B. H. Anderton, P. N. Leigh, C. E. Shaw and C. C. Miller (2000). "Glutamate slows axonal transport of neurofilaments in transfected neurons." J Cell Biol 150(1): 165-176.

Akashiba H, Matsuki N, Nishiyama N. p27 small interfering RNA induces cell death through elevating cell cycle activity in cultured cortical neurons: a proof-of-concept study. Cell Mol Life Sci. 2006; 63:2397-2404. doi: 10.1007/s00018-006-6194-4.

Andorfer, C., C. M. Acker, Y. Kress, P. R. Hof, K. Duff and P. Davies (2005). "Cell-cycle reentry and cell death in transgenic mice expressing nonmutant human tau isoforms." J Neurosci 25(22): 5446-5454.

Andrusiak, M. G., R. Vandenbosch, D. S. Park and R. S. Slack (2012). "The retinoblastoma protein is essential for survival of postmitotic neurons." J Neurosci 32(42): 14809-14814.

Arendt, T., M. K. Bruckner, H. J. Gertz and L. Marcova (1998). "Cortical distribution of neurofibrillary tangles in Alzheimer's disease matches the pattern of neurons that retain their capacity of plastic remodelling in the adult brain." Neuroscience 83(4): 991-1002.

Bernocco, S., C. Fondelli, S. Matteoni, L. Magnoni, S. Gotta, G. C. Terstappen and R. Raggiaschi (2008). "Sequential detergent fractionation of primary neurons for proteomics studies." Proteomics 8(5): 930-938.

Bommer G T, Gerin I, Feng Y, Kaczorowski A J, Kuick R, Love R E, Zhai Y, Giordano T J, Qin Z S, Moore B B, MacDougald O A, Cho K R, Fearon E R. p53-mediated activation of miRNA34 candidate tumor-suppressor genes. Curr Biol. 2007; 17:1298-1307.

Bonda, D. J., T. A. Evans, C. Santocanale, J. C. Llosa, J. Vina, V. Bajic, R. J. Castellani, S. L. Siedlak, G. Perry, M. A. Smith and H. G. Lee (2009). "Evidence for the progression through S-phase in the ectopic cell cycle re-entry of neurons in Alzheimer disease." Aging (Albany N.Y.) 1(4): 382-388.

Bonda, D. J., H. P. Lee, W. Kudo, X. Zhu, M. A. Smith and H. G. Lee (2010). "Pathological implications of cell cycle re-entry in Alzheimer disease." Expert Rev Mol Med 12: e19.

Busser, J., D. S. Geldmacher and K. Herrup (1998). "Ectopic cell cycle proteins predict the sites of neuronal cell death in Alzheimer's disease brain." J Neurosci 18(8): 2801-2807.

Byrnes, K. R., B. A. Stoica, S. Fricke, S. Di Giovanni and A. I. Faden (2007). "Cell cycle activation contributes to post-mitotic cell death and secondary damage after spinal cord injury." Brain 130(Pt 11): 2977-2992.

Cogswell, J. P., J. Ward, I. A. Taylor, M. Waters, Y. Shi, B. Cannon, K. Kelnar, J. Kemppainen, D. Brown, C. Chen, R. K. Prinjha, J. C. Richardson, A. M. Saunders, A. D. Roses and C. A. Richards (2008). "Identification of miRNA changes in Alzheimer's disease brain and CSF yields putative biomarkers and insights into disease pathways." J Alzheimers Dis 14(1): 27-41.

de las Cuevas, N., E. Urcelay, O. G. Hermida, R. A. Saiz-Diaz, F. Bermejo, M. S. Ayuso and A. Martin-Requero (2003). "Ca2+/calmodulin-dependent modulation of cell cycle elements pRb and p27kip1 involved in the enhanced proliferation of lymphoblasts from patients with Alzheimer dementia." Neurobiol Dis 13(3): 254-263.

Dill, H., B. Linder, A. Fehr and U. Fischer (2012). "Intronic miR-26b controls neuronal differentiation by repressing its host transcript, ctdsp2." Genes Dev 26(1): 25-30.

Fu, A. K., K. W. Hung, H. H. Wong, W. Y. Fu and N. Y. Ip (2012). "Cdk5 Phosphorylates a Component of the HDAC Complex and Regulates Histone Acetylation during Neuronal Cell Death." Neurosignals.

Futatsugi, A., E. Utreras, P. Rudrabhatla, H. Jaffe, H. C. Pant and A. B. Kulkarni (2012). "Cyclin-dependent kinase 5 regulates E2F transcription factor through phosphorylation of Rb protein in neurons." Cell Cycle 11(8): 1603-1610.

Gabriely, G., T. Wurdinger, S. Kesari, C. C. Esau, J. Burchard, P. S. Linsley and A. M. Krichevsky (2008). "MicroRNA 21 promotes glioma invasion by targeting matrix metalloproteinase regulators." Mol Cell Biol 28(17): 5369-5380.

Galderisi, U., F. P. Joni and A. Giordano (2003). "Cell cycle regulation and neural differentiation." Oncogene 22(33): 5208-5219.

Giovanni, A., E. Keramaris, E. J. Morris, S. T. Hou, M. O'Hare, N. Dyson, G. S. Robertson, R. S. Slack and D. S. Park (2000). "E2F1 mediates death of B-amyloid-treated cortical neurons in a manner independent of p53 and dependent on Bax and caspase 3." J Biol Chem 275(16): 11553-11560.

Gomez Ravetti, M., O. A. Rosso, R. Berretta and P. Moscato (2010). "Uncovering molecular biomarkers that correlate cognitive decline with the changes of hippocampus' gene expression profiles in Alzheimer's disease." PLoS One 5(4): e10153.

Greene, L. A., S. C. Biswas and D. X. Liu (2004). "Cell cycle molecules and vertebrate neuron death: E2F at the hub." Cell Death Differ 11(1): 49-60.

Hamdane, M., A. Bretteville, A. V. Sambo, K. Schindowski, S. Begard, A. Delacourte, P. Bertrand and L. Buee (2005). "p25/Cdk5-mediated retinoblastoma phosphorylation is an early event in neuronal cell death." J Cell Sci 118(Pt 6): 1291-1298.

Hammond, S. M. (2006). "microRNA detection comes of age." Nat Methods 3(1): 12-13.

Hebert, S. S., K. Hone, L. Nicolai, B. Bergmans, A. S. Papadopoulou, A. Delacourte and B. De Strooper (2009). "MicroRNA regulation of Alzheimer's Amyloid precursor protein expression." Neurobiol Dis 33(3): 422-428.

Hebert, S. S., K. Hone, L. Nicolai, A. S. Papadopoulou, W. Mandemakers, A. N. Silahtaroglu, S. Kauppinen, A. Delacourte and B. De Strooper (2008). "Loss of microRNA cluster miR-29a/b-1 in sporadic Alzheimer's disease correlates with increased BACE1/beta-secretase expression." Proc Natl Acad Sci USA 105(17): 6415-6420.

Hoglinger, G. U., J. J. Breunig, C. Depboylu, C. Rouaux, P. P. Michel, D. Alvarez-Fischer, A. L. Boutillier, J. Degregori, W. H. Oertel, P. Rakic, E. C. Hirsch and S. Hunot (2007). "The pRb/E2F cell-cycle pathway mediates cell death in Parkinson's disease." Proc Natl Acad Sci USA 104(9): 3585-3590.

Hoozemans, J. J., E. S. van Haastert, R. Veerhuis, T. Arendt, W. Scheper, P. Eikelenboom and A. J. Rozemuller (2005). "Maximal COX-2 and ppRb expression in neurons occurs during early Braak stages prior to the maximal activation of astrocytes and microglia in Alzheimer's disease." J Neuroinflammation 2: 27.

Hou, S. T., D. Callaghan, M. C. Fournier, I. Hill, L. Kang, B. Massie, P. Morley, C. Murray, I. Rasquinha, R. Slack and J. P. MacManus (2000). "The transcription factor E2F1 modulates apoptosis of neurons." J Neurochem 75(1): 91-100.

Huse, J. T., C. Brennan, D. Hambardzumyan, B. Wee, J. Pena, S. H. Rouhanifard, C. Sohn-Lee, C. le Sage, R. Agami, T. Tuschl and E. C. Holland (2009). "The PTEN-regulating microRNA miR-26a is amplified in high-grade glioma and facilitates gliomagenesis in vivo." Genes Dev 23(11): 1327-1337.

Hwang, H. W. and J. T. Mendell (2006). "MicroRNAs in cell proliferation, cell death, and tumorigenesis." Br J Cancer 94(6): 776-780.

Illenberger, S., Q. Zheng-Fischhofer, U. Preuss, K. Stamer, K. Baumann, B. Trinczek, J. Biernat, R. Godemann, E. M. Mandelkow and E. Mandelkow (1998). "The endogenous and cell cycle-dependent phosphorylation of tau protein in living cells: implications for Alzheimer's disease." Mol Biol Cell 9(6): 1495-1512.

Janicki, S. M. and M. J. Monteiro (1999). "Presenilin overexpression arrests cells in the G1 phase of the cell cycle. Arrest potentiated by the Alzheimer's disease PS2 (N141I)mutant." Am J Pathol 155(1): 135-144.

Jaworski, T., I. Dewachter, B. Lechat, S. Croes, A. Termont, D. Demedts, P. Borghgraef, H. Devijver, R. K. Filipkowski, L. Kaczmarek, S. Kugler and F. Van Leuven (2009). "AAV-tau mediates pyramidal neurodegeneration by cell-cycle re-entry without neurofibrillary tangle formation in wild-type mice." PLoS One 4(10): e7280.

Jordan-Sciutto, K. L., R. Dorsey, E. M. Chalovich, R. R. Hammond and C. L. Achim (2003). "Expression patterns of retinoblastoma protein in Parkinson disease." J Neuropathol Exp Neurol 62(1): 68-74.

Jordan-Sciutto, K. L., L. M. Malaiyandi and R. Bowser (2002). "Altered distribution of cell cycle transcriptional regulators during Alzheimer disease." J Neuropathol Exp Neurol 61(4): 358-367.

Keeney, J. T., A. M. Swomley, J. L. Harris, A. Fiorini, M. I. Mitov, M. Perluigi, R. Sultana and D. A. Butterfield (2012). "Cell cycle proteins in brain in mild cognitive impairment: insights into progression to Alzheimer disease." Neurotox Res 22(3): 220-230.

Kim, H., W. Huang, X. Jiang, B. Pennicooke, P. J. Park and M. D. Johnson (2010). "Integrative genome analysis reveals an oncomir/oncogene cluster regulating glioblastoma survivorship." Proc Natl Acad Sci USA 107(5): 2183-2188.

Kota, J., R. R. Chivukula, K. A. O'Donnell, E. A. Wentzel, C. L. Montgomery, H. W. Hwang, T. C. Chang, P. Vivekanandan, M. Torbenson, K. R. Clark, J. R. Mendell and J. T. Mendell (2009). "Therapeutic microRNA delivery suppresses tumorigenesis in a murine liver cancer model." Cell 137(6): 1005-1017.

Krichevsky A M, Kosik K S. Neuronal RNA granules: a link between RNA localization and stimulation-dependent translation. Neuron. 2001; 32:683-696.

Kulshreshtha, R., M. Ferracin, M. Negrini, G. A. Calin, R. V. Davuluri and M. Ivan (2007). "Regulation of microRNA expression: the hypoxic component." Cell Cycle 6(12): 1426-1431.

Lau, P. and B. de Strooper (2010). "Dysregulated microRNAs in neurodegenerative disorders." Semin Cell Dev Biol 21(7): 768-773.

Lee, M. S. and L. H. Tsai (2003). "Cdk5: one of the links between senile plaques and neurofibrillary tangles?" J Alzheimers Dis 5(2): 127-137.

Liu N, Landreh M, Cao K, Abe M, Hendriks G J, Kennerdell J R, Zhu Y, Wang L S, Bonini N M. The microRNA miR-34 modulates ageing and neurodegeneration in *Drosophila*. Nature. 2012; 482:519-523.

Lopes, J. P., M. Blurton-Jones, T. R. Yamasaki, P. Agostinho and F. M. LaFerla (2009). "Activation of cell cycle proteins in transgenic mice in response to neuronal loss but not amyloid-beta and tau pathology." J Alzheimers Dis 16(3): 541-549.

Lopes, J. P., C. R. Oliveira and P. Agostinho (2009). "Cdk5 acts as a mediator of neuronal cell cycle re-entry triggered by amyloid-beta and prion peptides." Cell Cycle 8(1): 97-104.

Lu, J., M. L. He, L. Wang, Y. Chen, X. Liu, Q. Dong, Y. C. Chen, Y. Peng, K. T. Yao, H. F. Kung and X. P. Li (2011). "MiR-26a inhibits cell growth and tumorigenesis of nasopharyngeal carcinoma through repression of EZH2." Cancer Res 71(1): 225-233.

Manning A L, Dyson N J. pRB, a tumor suppressor with a stabilizing presence. Trends Cell Biol. 2011; 21:433-441.

Mazanetz, M. P. and P. M. Fischer (2007). "Untangling tau hyperphosphorylation in drug design for neurodegenerative diseases." Nat Rev Drug Discov 6(6): 464-479.

McShea, A., H. G. Lee, R. B. Petersen, G. Casadesus, I. Vincent, N. J. Linford, J. O. Funk, R. A. Shapiro and M. A. Smith (2007). "Neuronal cell cycle re-entry mediates Alzheimer disease-type changes." Biochim Biophys Acta 1772(4): 467-472.

Moh, C., J. Z. Kubiak, V. P. Bajic, X. Zhu, M. A. Smith and H. G. Lee (2011). "Cell cycle deregulation in the neurons of Alzheimer's disease." Results Probl Cell Differ 53: 565-576.

Munoz, U., N. de Las Cuevas, F. Bartolome, O. G. Hermida, F. Bermejo and A. Martin-Requero (2005). "The cyclopentenone 15-deoxy-delta(12,14)-prostaglandin J2 inhibits G1/S transition and retinoblastoma protein phosphorylation in immortalized lymphocytes from Alzheimer's disease patients." Exp Neurol 195(2): 508-517.

Nagy, Z., M. M. Esiri, A. M. Cato and A. D. Smith (1997). "Cell cycle markers in the hippocampus in Alzheimer's disease." Acta Neuropathol 94(1): 6-15.

Neve, R. L. and D. L. McPhie (2006). "The cell cycle as a therapeutic target for Alzheimer's disease." Pharmacol Ther 111(1): 99-113.

Park, D. S., E. J. Morris, R. Bremner, E. Keramaris, J. Padmanabhan, M. Rosenbaum, M. L. Shelanski, H. M. Geller and L. A. Greene (2000). "Involvement of retinoblastoma family members and E2F/DP complexes in the death of neurons evoked by DNA damage." J Neurosci 20(9): 3104-3114.

Park, K. H., J. L. Hallows, P. Chakrabarty, P. Davies and I. Vincent (2007). "Conditional neuronal simian virus 40 T antigen expression induces Alzheimer-like tau and amyloid pathology in mice." J Neurosci 27(11): 2969-2978.

Preuss, U., F. Doring, S. Illenberger and E. M. Mandelkow (1995). "Cell cycle-dependent phosphorylation and microtubule binding of tau protein stably transfected into Chinese hamster ovary cells." Mol Biol Cell 6(10): 1397-1410.

Provost, P. (2010). "Interpretation and applicability of microRNA data to the context of Alzheimer's and age-related diseases." Aging (Albany N.Y.) 2(3): 166-169.

Ranganathan, S., S. Scudiere and R. Bowser (2001). "Hyperphosphorylation of the retinoblastoma gene product and altered subcellular distribution of E2F-1 during Alzheimer's disease and amyotrophic lateral sclerosis." J Alzheimers Dis 3(4): 377-385.

Rashidian, J., G. Iyirhiaro, H. Aleyasin, M. Rios, I. Vincent, S. Callaghan, R. J. Bland, R. S. Slack, M. J. During and D. S. Park (2005). "Multiple cyclin-dependent kinases signals are critical mediators of ischemia/hypoxic neuronal death in vitro and in vivo." Proc Natl Acad Sci USA 102(39): 14080-14085.

Rogakou E P, Pilch D R, On A H, Ivanova V S, Bonner W M. DNA double-stranded breaks induce histone H2AX phosphorylation on serine 139. J Biol Chem. 1998; 273: 5858-5868.

Satoh, J. (2012). "Molecular network of microRNA targets in Alzheimer's disease brains." Exp Neurol 235(2): 436-446.

Schindowski, K., K. Belarbi, A. Bretteville, K. Ando and L. Buee (2008). "Neurogenesis and cell cycle-reactivated neuronal death during pathogenic tau aggregation." Genes Brain Behav 7 Suppl 1: 92-100.

Schwartz E I, Smilenov L B, Price M A, Osredkar T, Baker R A, Ghosh S, Shi F D, Vollmer T L, Lencinas A, Stearns D M, Gorospe M, Kruman I I. Cell cycle activation in postmitotic neurons is essential for DNA repair. Cell Cycle. 2007; 6:318-329.

Sellers, W. R., J. W. Rodgers and W. G. Kaelin, Jr. (1995). "A potent transrepression domain in the retinoblastoma protein induces a cell cycle arrest when bound to E2F sites." Proc Natl Acad Sci USA 92(25): 11544-11548.

Seward, M. E., E. Swanson, A. Norambuena, A. Reimann, J. N. Cochran, R. Li, E. D. Roberson and G. S. Bloom (2013). "Amyloid-beta Signals Through Tau to Drive Ectopic Neuronal Cell Cycle Re-entry in Alzheimer's Disease." J Cell Sci.

Sheaff R J, Groudine M, Gordon M, Roberts J M, Clurman B E. Cyclin E-CDK2 is a regulator of p27Kip1. Genes Dev. 1997; 11:1464-1478.

Smith, D. S., G. Leone, J. DeGregori, M. N. Ahmed, M. B. Qumsiyeh and J. R. Nevins (2000). "Induction of DNA replication in adult rat neurons by deregulation of the retinoblastoma/E2F G1 cell cycle pathway." Cell Growth Differ 11(12): 625-633.

Smith, M. Z., Z. Nagy and M. M. Esiri (1999). "Cell cycle-related protein expression in vascular dementia and Alzheimer's disease." Neurosci Lett 271(1): 45-48.

Smith P Y, Delay C, Girard J, Papon M A, Planel E, Sergeant N, Buée L, Hébert S S. MicroRNA-132 loss is associated with tau exon 10 inclusion in progressive supranuclear palsy. Hum Mol Genet. 2011; 20:4016-4024.

Stone, J. G., S. L. Siedlak, M. Tabaton, A. Hirano, R. J. Castellani, C. Santocanale, G. Perry, M. A. Smith, X. Zhu and H. G. Lee (2011). "The cell cycle regulator phosphorylated retinoblastoma protein is associated with tau pathology in several tauopathies." J Neuropathol Exp Neurol 70(7): 578-587.

Swerdlow, R. H. (2012). "Alzheimer's disease pathologic cascades: who comes first, what drives what." Neurotox Res 22(3): 182-194.

Thakur, A., S. L. Siedlak, S. L. James, D. J. Bonda, A. Rao, K. M. Webber, A. Camins, M. Pallas, G. Casadesus, H. G. Lee, R. Bowser, A. K. Raina, G. Perry, M. A. Smith and X. Zhu (2008). "Retinoblastoma protein phosphorylation at multiple sites is associated with neurofibrillary pathology in Alzheimer disease." Int J Clin Exp Pathol 1(2): 134-146.

Vilardo, E., C. Barbato, M. Ciotti, C. Cogoni and F. Ruberti (2010). "MicroRNA-101 regulates amyloid precursor protein expression in hippocampal neurons." J Biol Chem 285(24): 18344-18351.

Vincent, I., G. Jicha, M. Rosado and D. W. Dickson (1997). "Aberrant expression of mitotic cdc2/cyclin B1 kinase in degenerating neurons of Alzheimer's disease brain." J Neurosci 17(10): 3588-3598.

Vlach J, Hennecke S, Amati B. Phosphorylation-dependent degradation of the cyclin-dependent kinase inhibitor p27. EMBO J. 1997; 16:5334-5344.

Wang, W. X., Q. Huang, Y. Hu, A. J. Stromberg and P. T. Nelson (2011). "Patterns of microRNA expression in normal and early Alzheimer's disease human temporal cortex: white matter versus gray matter." Acta Neuropathol 121(2): 193-205.

Wong H K, Veremeyko T, Patel N, Lemere C A, Walsh D M, Esau C, Vanderburg C, Krichevsky A M. De-repression of FOXO3a death axis by microRNA-132 and -212 causes neuronal apoptosis in Alzheimer's disease. Hum Mol Genet. 2013; 22:3077-3092. doi: 10.1093/hmg/ddt164. [PubMed] [Cross Ref]

Yang, Y., D. S. Geldmacher and K. Herrup (2001). "DNA replication precedes neuronal cell death in Alzheimer's disease." J Neurosci 21(8): 2661-2668.

Ye W, Blain S W. S phase entry causes homocysteine-induced death while ataxia telangiectasia and Rad3 related protein functions anti-apoptotically to protect neurons. Brain. 2010; 133:2295-2312. doi: 10.1093/brain/awq139.

Yoshida, A., N. Yoneda-Kato and J. Y. Kato (2013). "CSN5 specifically interacts with CDK2 and controls senescence in a cytoplasmic cyclin E-mediated manner." Sci Rep 3: 1054.

Yurov, Y. B., S. G. Vorsanova and I. Y. Iourov (2011). "The DNA replication stress hypothesis of Alzheimer's disease." ScientificWorldJournal 11: 2602-2612.

Zhang, J., S. A. Cicero, L. Wang, R. R. Romito-Digiacomo, Y. Yang and K. Herrup (2008). "Nuclear localization of Cdk5 is a key determinant in the postmitotic state of neurons." Proc Natl Acad Sci USA 105(25): 8772-8777.

Zhang, J. and K. Herrup (2008). "Cdk5 and the non-catalytic arrest of the neuronal cell cycle." Cell Cycle 7(22): 3487-3490.

Zhang, J., H. Li and K. Herrup (2010). "Cdk5 nuclear localization is p27-dependent in nerve cells: implications for cell cycle suppression and caspase-3 activation." J Biol Chem 285(18): 14052-14061.

Zhu, H. C., L. M. Wang, M. Wang, B. Song, S. Tan, J. F. Teng and D. X. Duan (2012). "MicroRNA-195 down-regulates Alzheimer's disease amyloid-beta production by targeting BACE1." Brain Res Bull 88(6): 596-601.

Zhu, Y., Y. Lu, Q. Zhang, J. J. Liu, T. J. Li, J. R. Yang, C. Zeng and S. M. Zhuang (2012). "MicroRNA-26a/b and their host genes cooperate to inhibit the G1/S transition by activating the pRb protein." Nucleic Acids Res 40(10): 4615-4625.

Zovoilis, A., H. Y. Agbemenyah, R. C. Agis-Balboa, R. M. Stilling, D. Edbauer, P. Rao, L. Farinelli, I. Delalle, A. Schmitt, P. Falkai, S. Bahari-Javan, S. Burkhardt, F. Sananbenesi and A. Fischer (2011). "microRNA-34c is a novel target to treat dementias." EMBO J 30(20): 4299-4308.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of decreasing tau phosphorylation in a mammalian neuron, the method comprising contacting the neuron with an effective amount of one or more inhibitory nucleic acids targeting microRNA-26b.

2. The method of claim 1, wherein the inhibitory nucleic acid comprises the sequence ACTTGA (SEQ ID NO:5).

3. The method of claim 1, wherein the inhibitory nucleic acid is an antagomiR.

4. The method of claim 1, wherein the inhibitory nucleic acid comprises one or more locked nucleotides.

5. The method of claim 1, wherein the inhibitory nucleic acid is a gapmer or mixmer.

6. The method of claim 1, wherein the inhibitory nucleic acid does not comprise three or more consecutive guanosine nucleotides.

7. The method of claim 1, wherein the inhibitory nucleic acid does not comprise four or more consecutive guanosine nucleotides.

8. The method of claim 1, wherein the inhibitory nucleic acid is 8 to 21 nucleotides in length.

9. The method of claim 1, wherein at least one nucleotide of the inhibitory nucleic acid is a nucleotide analogue.

10. The method of claim 1, wherein at least one nucleotide of the inhibitory nucleic acid comprises a 2' O-methyl.

11. The method of claim 1, wherein each nucleotide of the inhibitory nucleic acid comprises a 2' O-methyl.

12. The method of claim 1, wherein the inhibitory nucleic acid comprises at least one ribonucleotide, at least one deoxyribonucleotide, or at least one bridged nucleotide.

13. The method of claim 12, wherein the bridged nucleotide is a LNA nucleotide, a cEt nucleotide or a ENA modified nucleotide.

14. The method of claim 1, wherein each nucleotide of the oligonucleotide is a LNA nucleotide.

15. The method of claim 1, wherein one or more of the nucleotides of the inhibitory nucleic acid comprise 2'-fluoro-deoxyribonucleotides.

16. The method of claim 1, wherein one or more of the nucleotides of the inhibitory nucleic acid comprise 2'-O-methyl nucleotides.

17. The method of claim 1, wherein one or more of the nucleotides of the inhibitory nucleic acid comprise ENA nucleotide analogues.

18. The method of claim 1, wherein one or more of the nucleotides of the inhibitory nucleic acid comprise LNA nucleotides.

19. The method of claim 1, wherein the nucleotides of the inhibitory nucleic acid comprise phosphorothioate internucleotide linkages between at least two nucleotides.

20. The method of claim 1, wherein the nucleotides of the inhibitory nucleic acid comprise phosphorothioate internucleotide linkages between all nucleotides.

21. The method of claim 1, wherein the neuron is in a subject.

22. The method of claim 21, wherein the subject is human.

23. The method of claim 22, wherein the subject has Alzheimer's disease.

* * * * *